United States Patent
Takashino et al.

(10) Patent No.: US 7,935,114 B2
(45) Date of Patent: May 3, 2011

(54) CURATIVE TREATMENT SYSTEM, CURATIVE TREATMENT DEVICE, AND TREATMENT METHOD FOR LIVING TISSUE USING ENERGY

(75) Inventors: Tomoyuki Takashino, Hino (JP); Toru Nagase, Tachikawa (JP); Koji Iida, Sagamihara (JP); Mai Wakamatsu, Hino (JP)

(73) Assignee: Olympus Medical Systems Corp. (JP)

( * ) Notice: Subject to any disclaimer, the term of this patent is extended or adjusted under 35 U.S.C. 154(b) by 130 days.

(21) Appl. No.: 11/674,766

(22) Filed: Feb. 14, 2007

(65) Prior Publication Data

US 2008/0195091 A1    Aug. 14, 2008

(51) Int. Cl.
*A61B 18/14* (2006.01)

(52) U.S. Cl. .......................................... 606/51; 606/41

(58) Field of Classification Search ................ 606/41, 606/51–52
See application file for complete search history.

(56) References Cited

U.S. PATENT DOCUMENTS

| | | | |
|---|---|---|---|
| 2,002,594 A * | 5/1935 | Wappler et al. ................. | 606/46 |
| 5,531,744 A | 7/1996 | Nardella et al. | |
| 5,647,871 A | 7/1997 | Levine et al. | |
| 5,693,051 A | 12/1997 | Schulze et al. | |
| 5,951,546 A | 9/1999 | Lorentzen | |
| 6,074,389 A | 6/2000 | Levine et al. | |
| 6,113,598 A * | 9/2000 | Baker ............................. | 606/51 |
| 6,500,176 B1 | 12/2002 | Truckai et al. | |
| 6,626,901 B1 | 9/2003 | Treat et al. | |
| 6,776,780 B2 * | 8/2004 | Mulier et al. .................... | 606/51 |
| 6,953,461 B2 | 10/2005 | McClurken et al. | |
| 2002/0099374 A1* | 7/2002 | Pendekanti et al. ............. | 606/51 |
| 2002/0115997 A1* | 8/2002 | Truckai et al. ................... | 606/51 |
| 2003/0216733 A1* | 11/2003 | McClurken et al. ............. | 606/51 |
| 2005/0004568 A1 | 1/2005 | Lawes et al. | |
| 2005/0124987 A1* | 6/2005 | Goble .............................. | 606/50 |
| 2005/0203499 A1* | 9/2005 | Pendekanti et al. ............. | 606/27 |
| 2006/0052778 A1 | 3/2006 | Chapman et al. | |

FOREIGN PATENT DOCUMENTS

| | | |
|---|---|---|
| EP | 0 996 380 | 1/2005 |
| EP | 1 372 505 | 6/2006 |
| WO | WO 02/03874 | 1/2002 |
| WO | WO 02/058544 | 8/2002 |

OTHER PUBLICATIONS

International Search Report dated Nov. 6, 2007 issued in corresponding PCT Application No. PCT/JP2007/069510.

* cited by examiner

*Primary Examiner* — Michael Peffley
*Assistant Examiner* — Benjamin Lee
(74) *Attorney, Agent, or Firm* — Ostrolenk Faber LLP

(57) ABSTRACT

A treatment system includes an energy source, a pair of holding portions, an output portion and a first channel. At least one of the holding portions is configured to relatively move with respect to the other holding portion. The output portion is disposed on at least one of the pair of holding portions and connected with the energy source. The output portion is configured to generate a fluid including a gas and/or a liquid from the living tissue by the energy supplied from the energy source. The first channel is disposed at a position close to the output portion. The first channel is configured to pass the fluid generated from the living tissue.

19 Claims, 28 Drawing Sheets

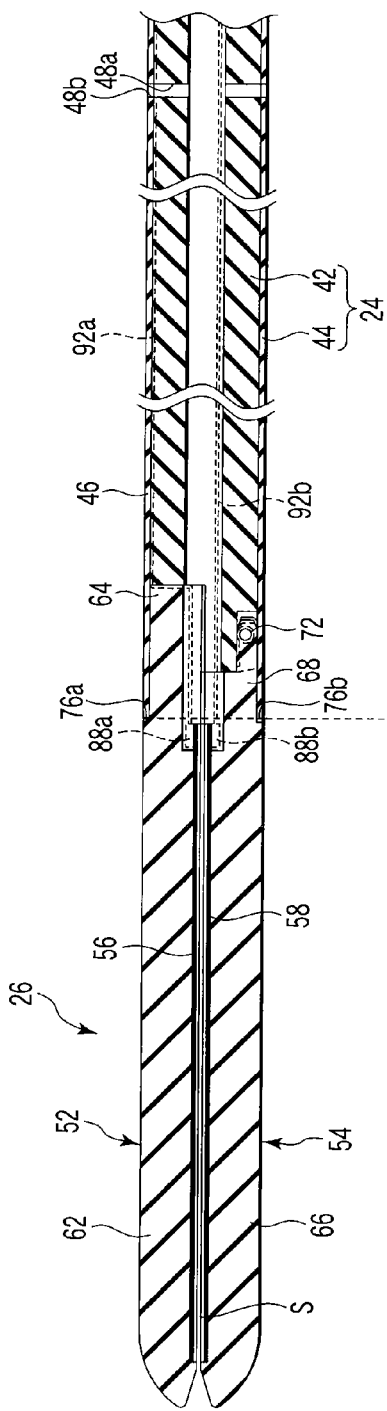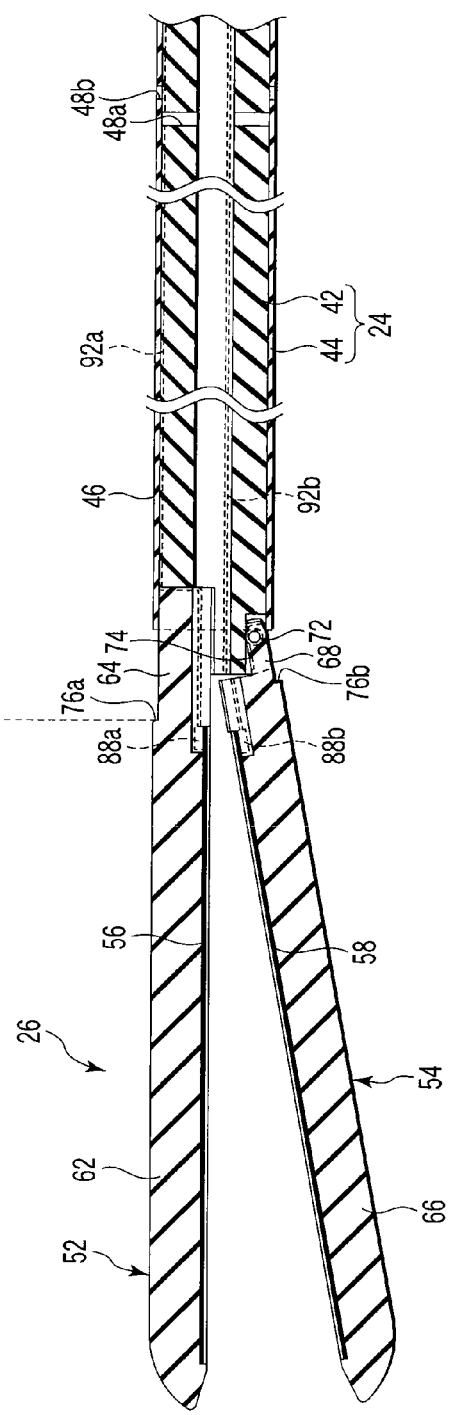
FIG. 2A
FIG. 2B

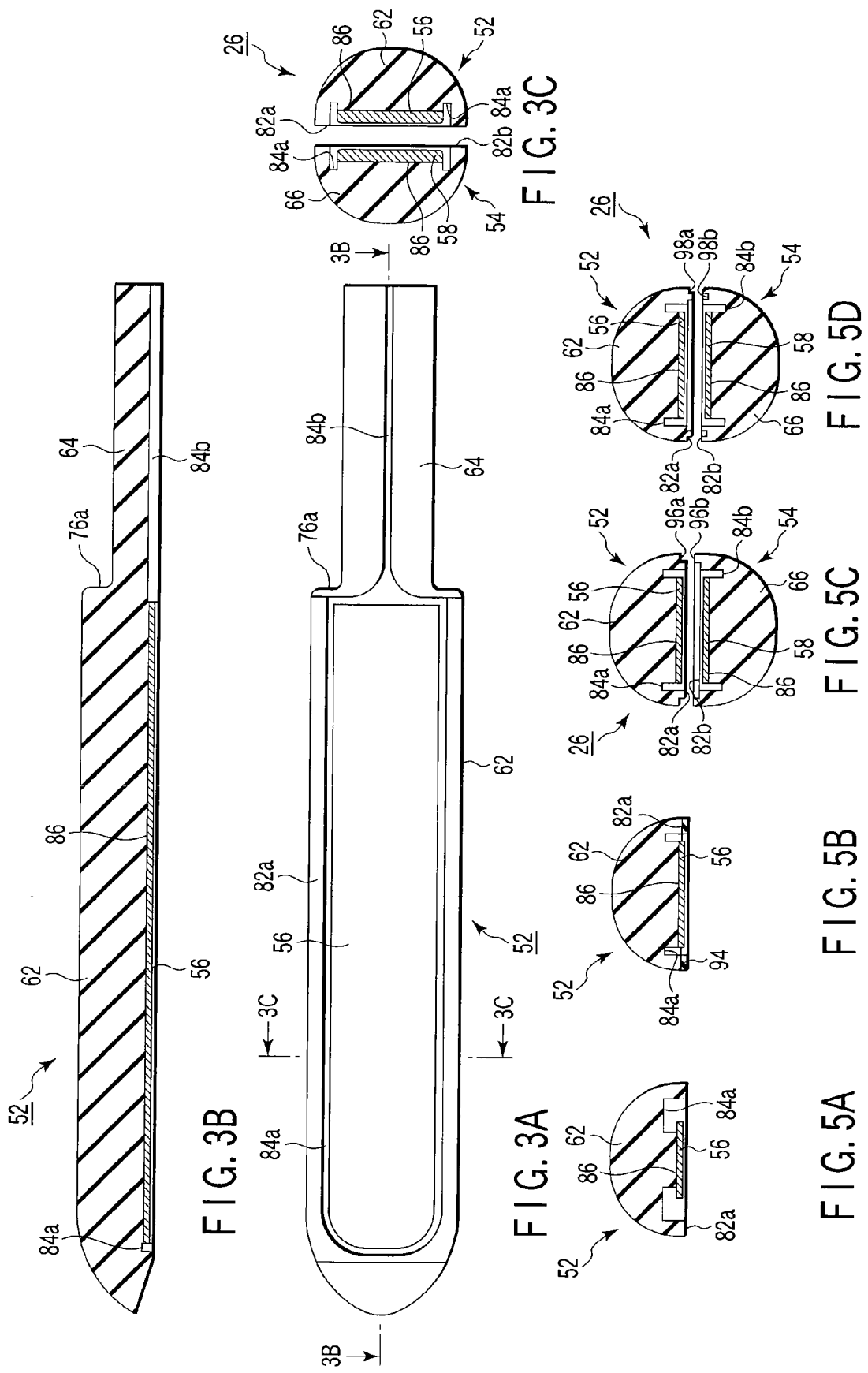

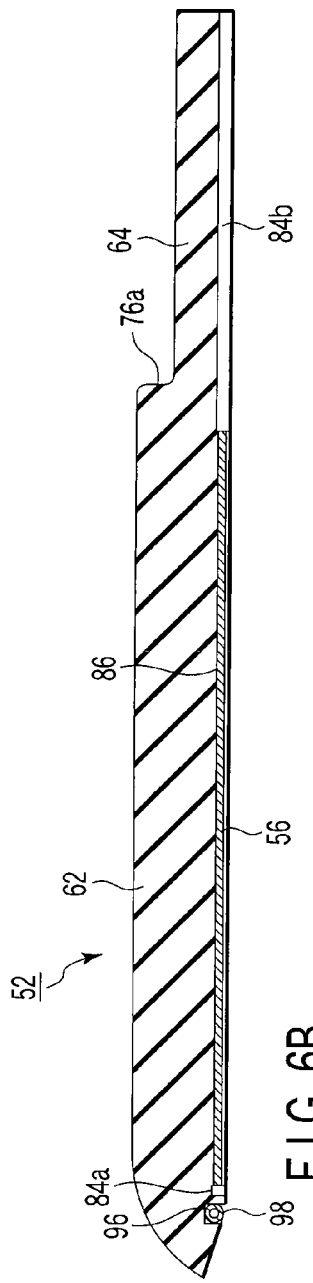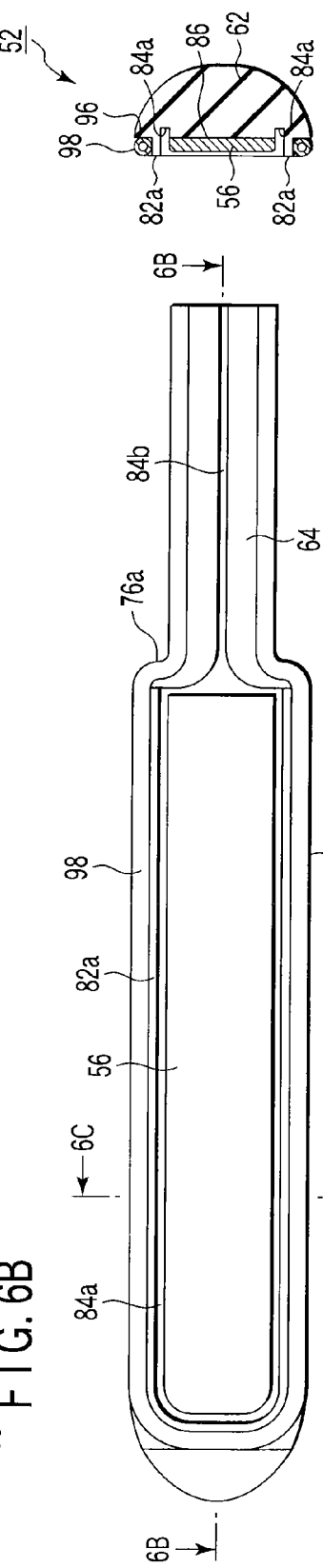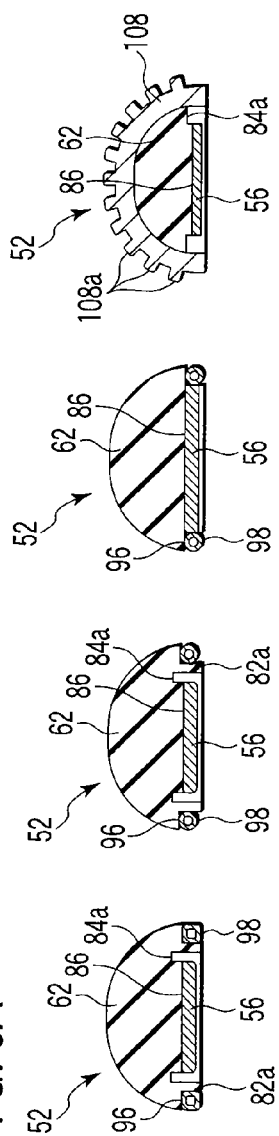

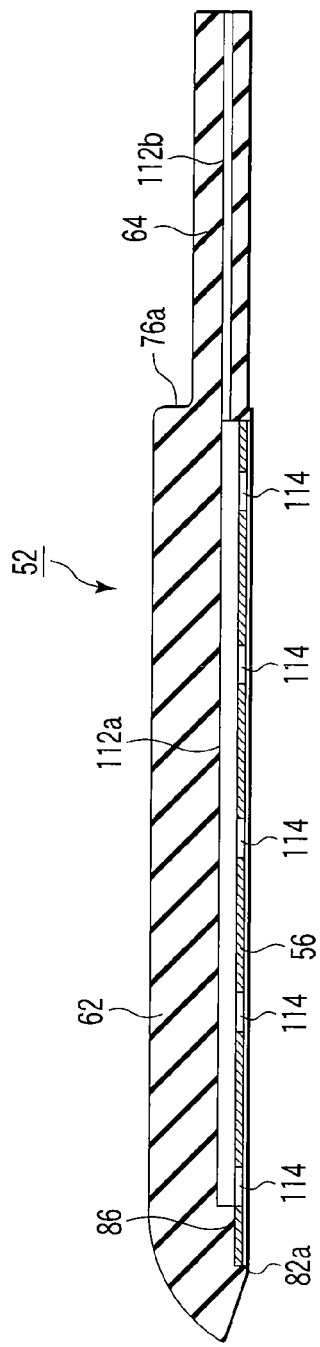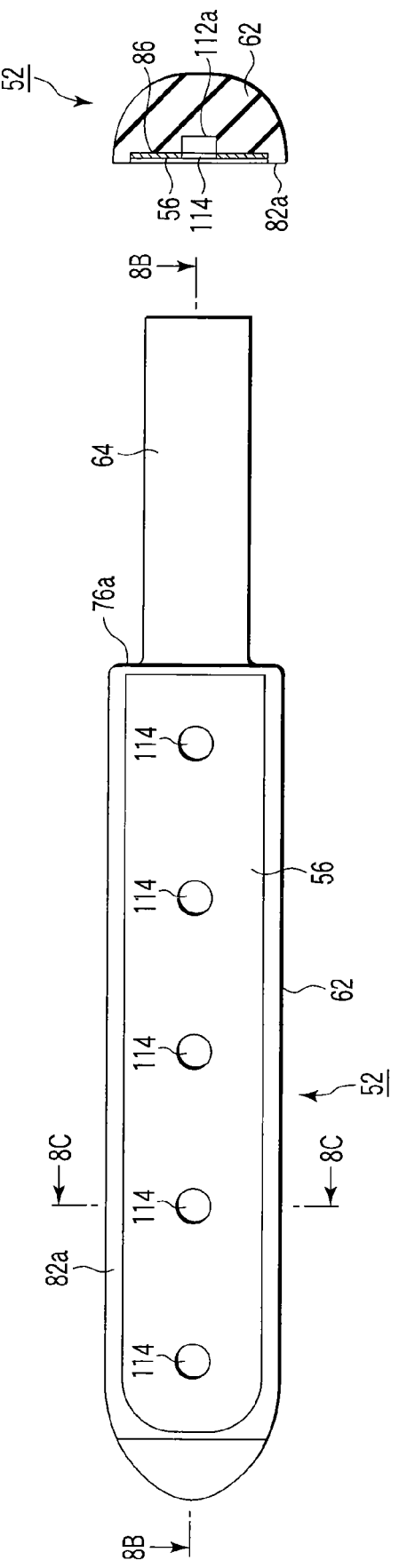

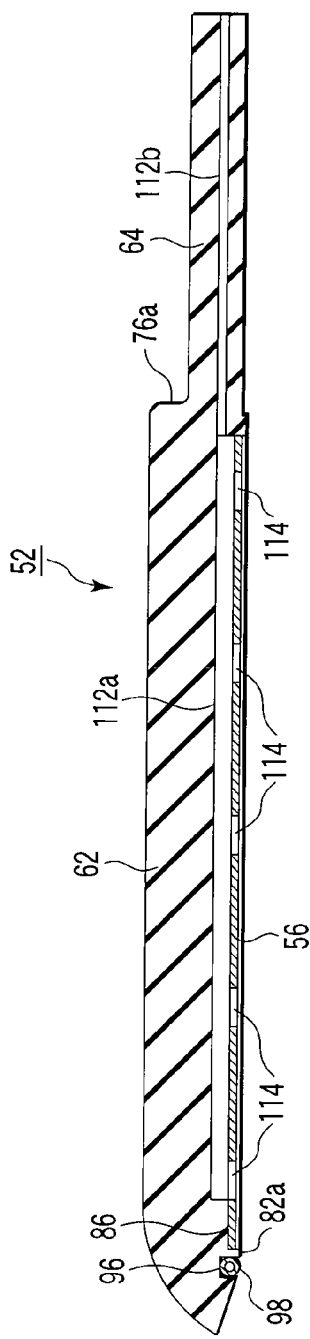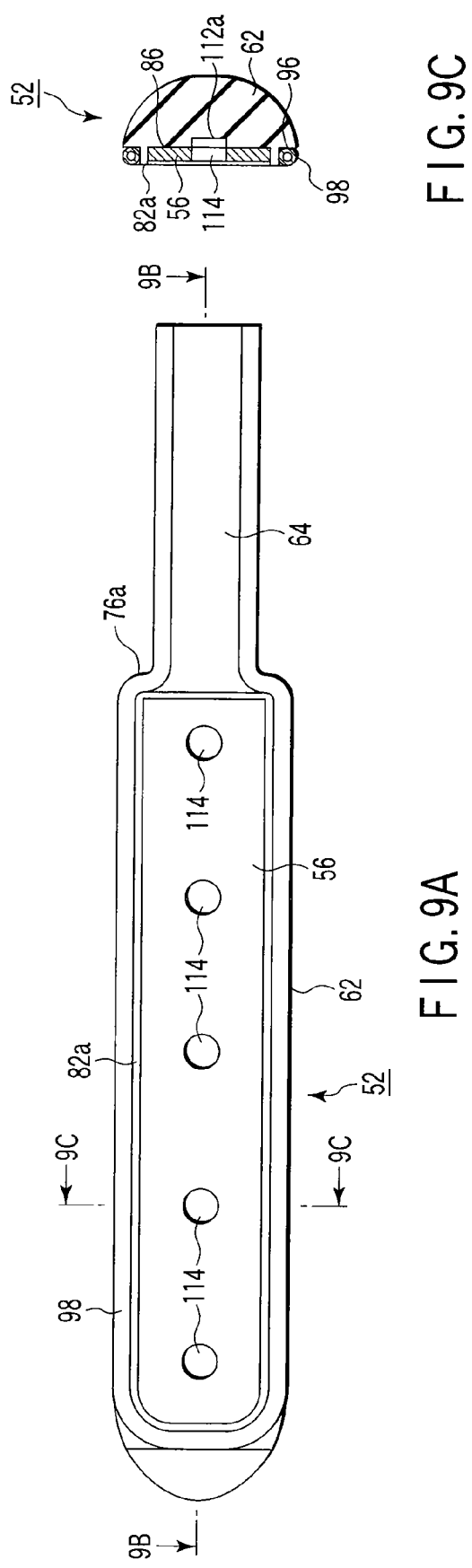

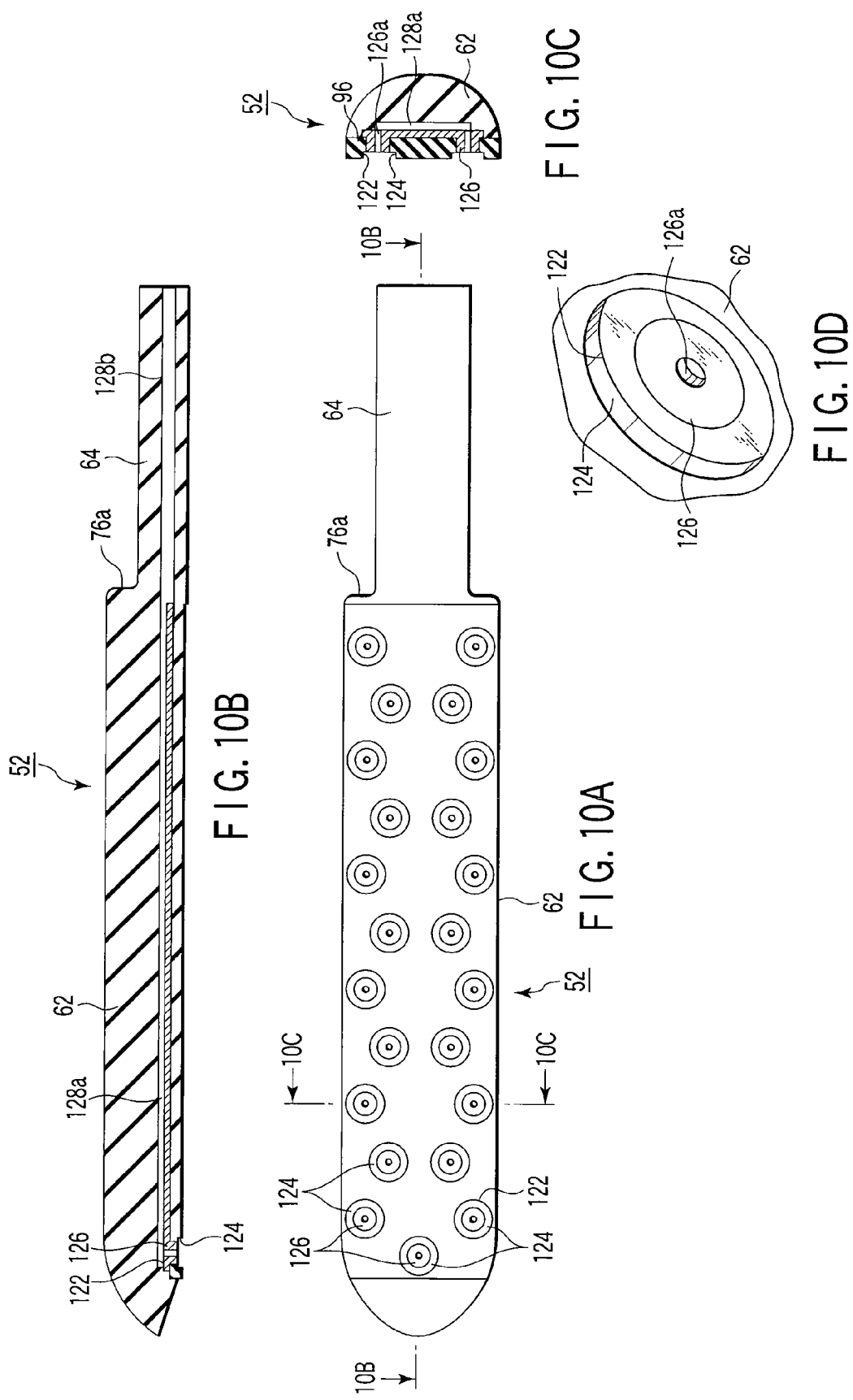

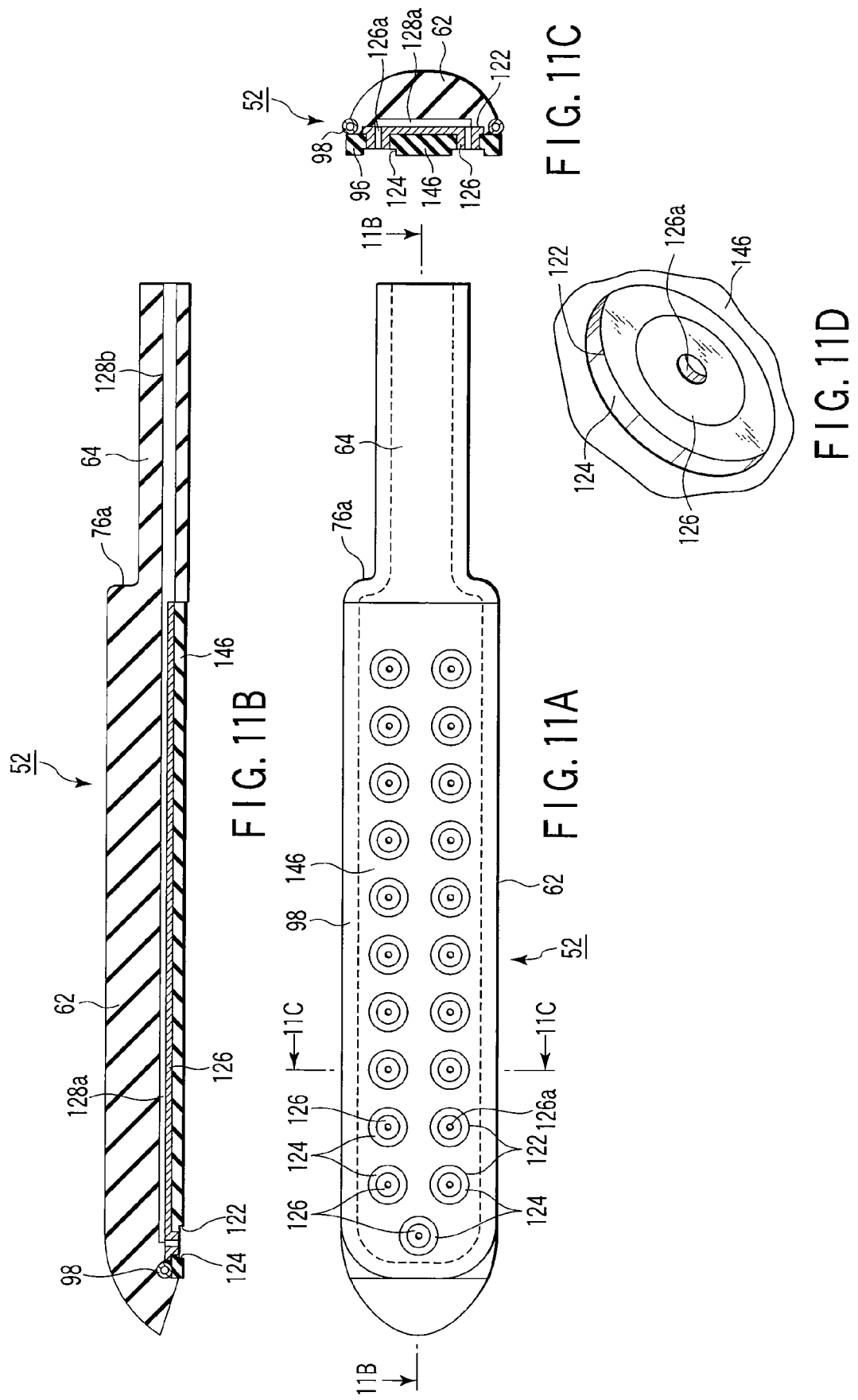

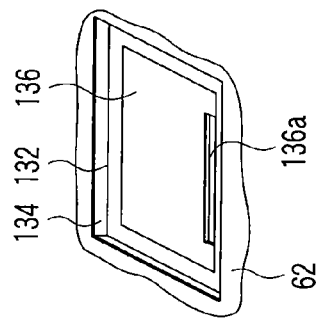
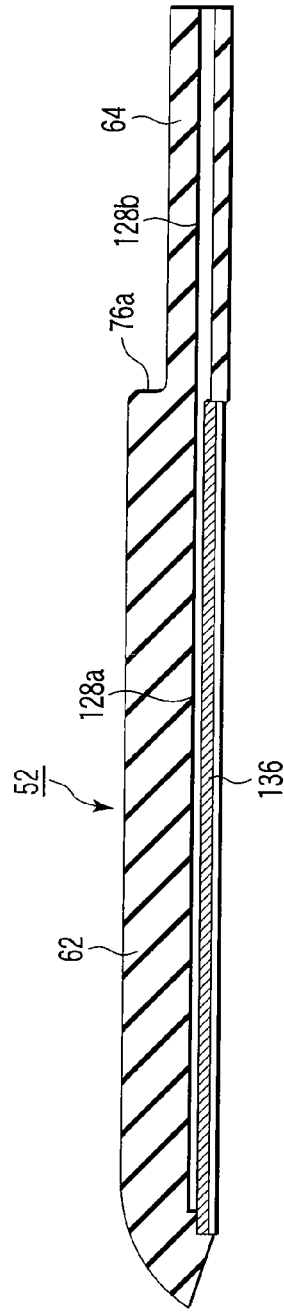
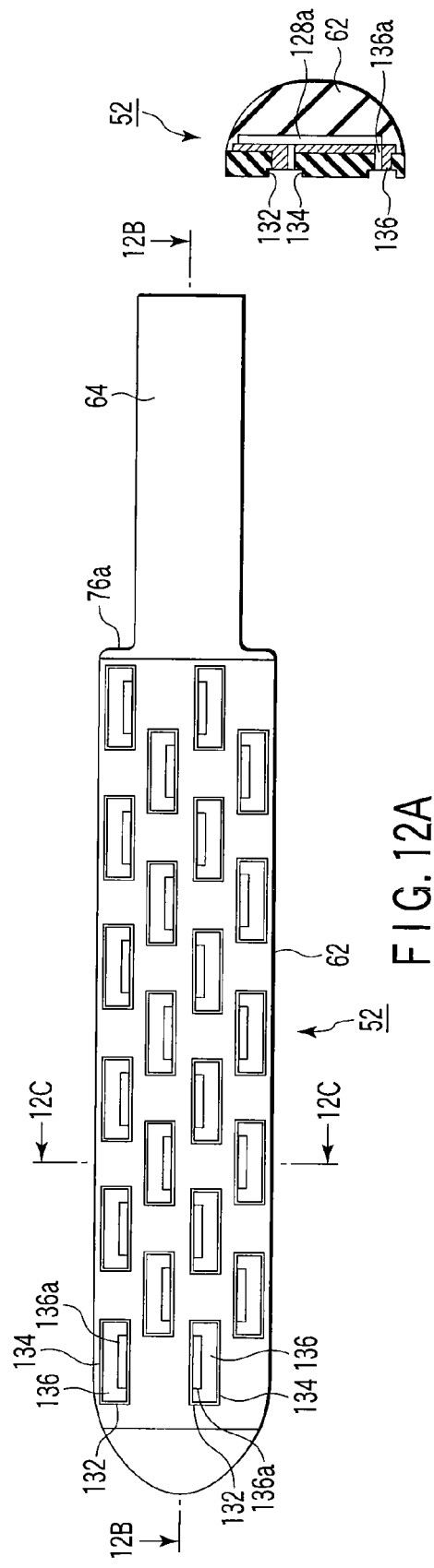

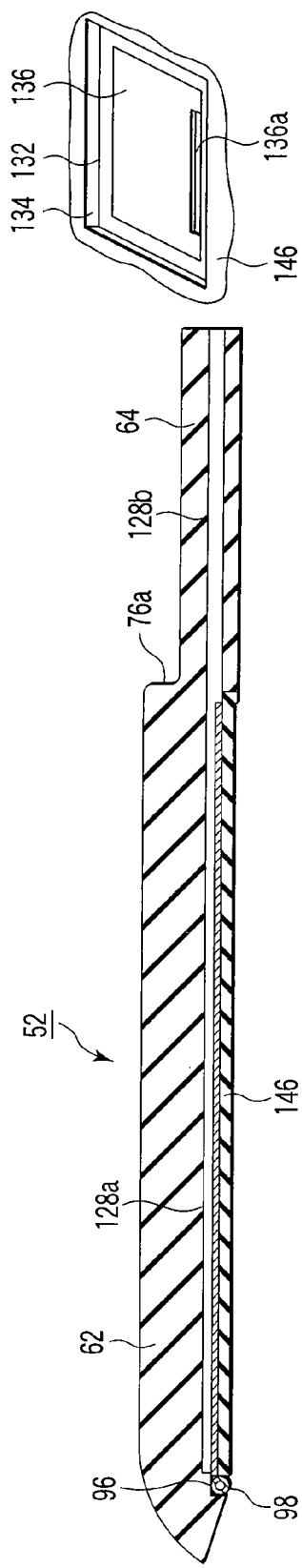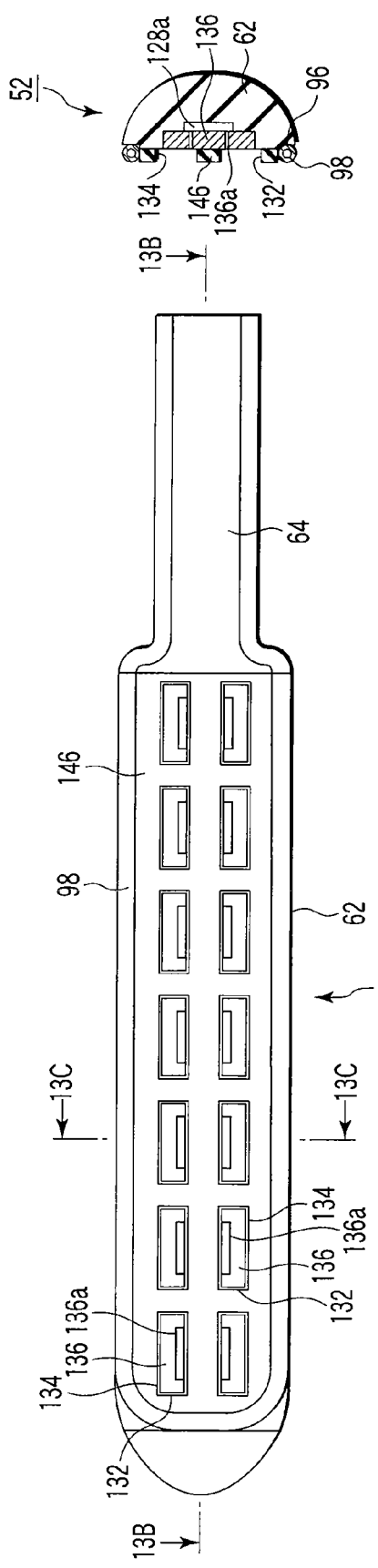

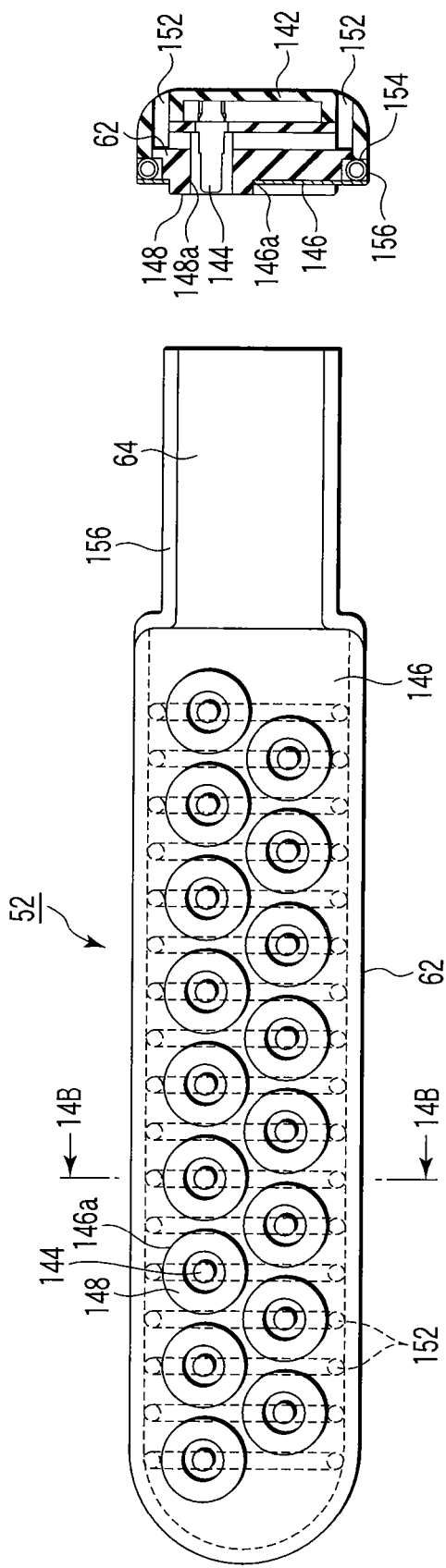
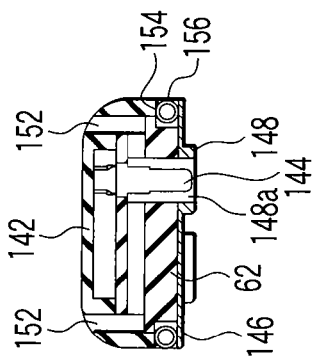
FIG. 14A
FIG. 14B
FIG. 14C

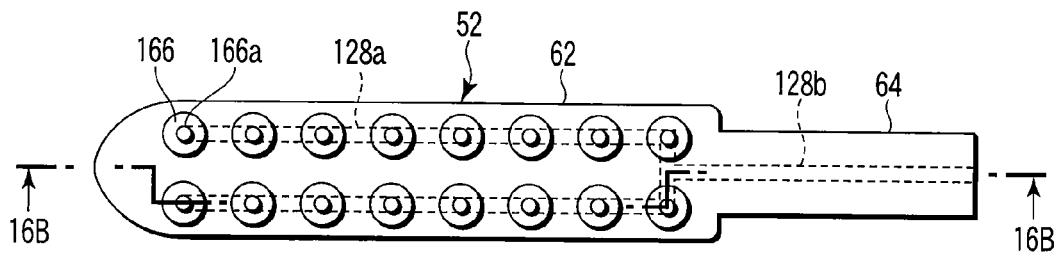
F I G. 16A
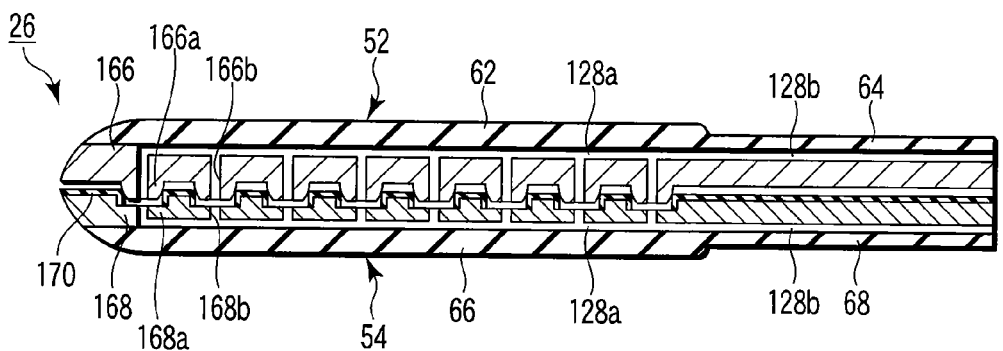
F I G. 16B
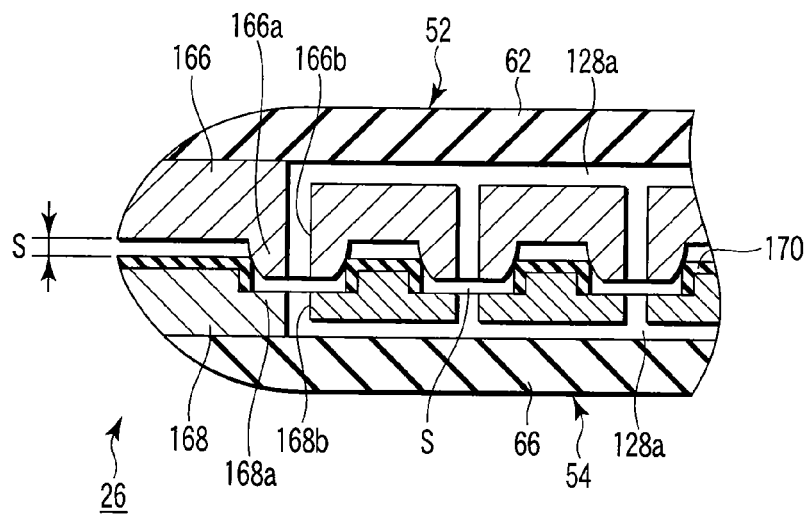
F I G. 16C

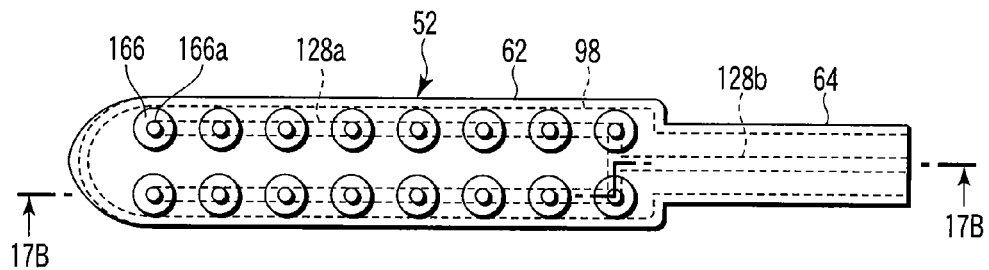
F I G. 17A
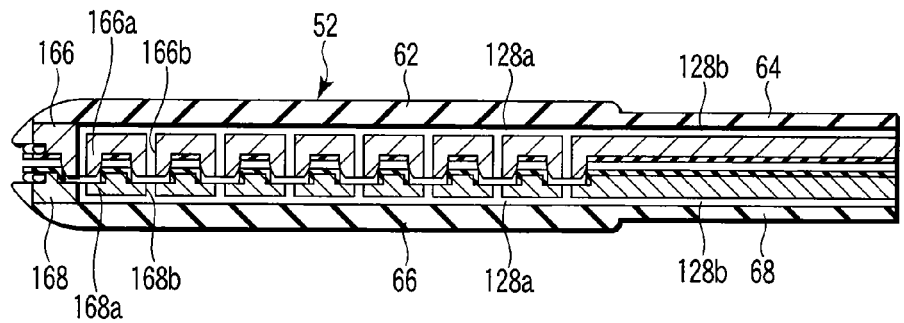
F I G. 17B
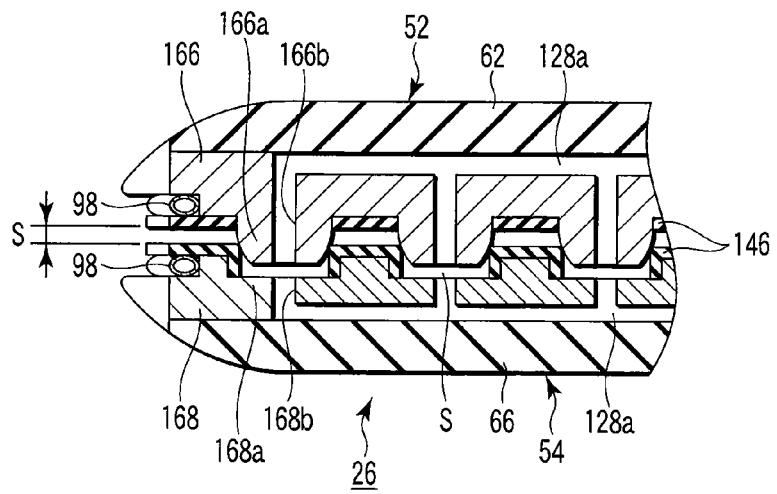
F I G. 17C

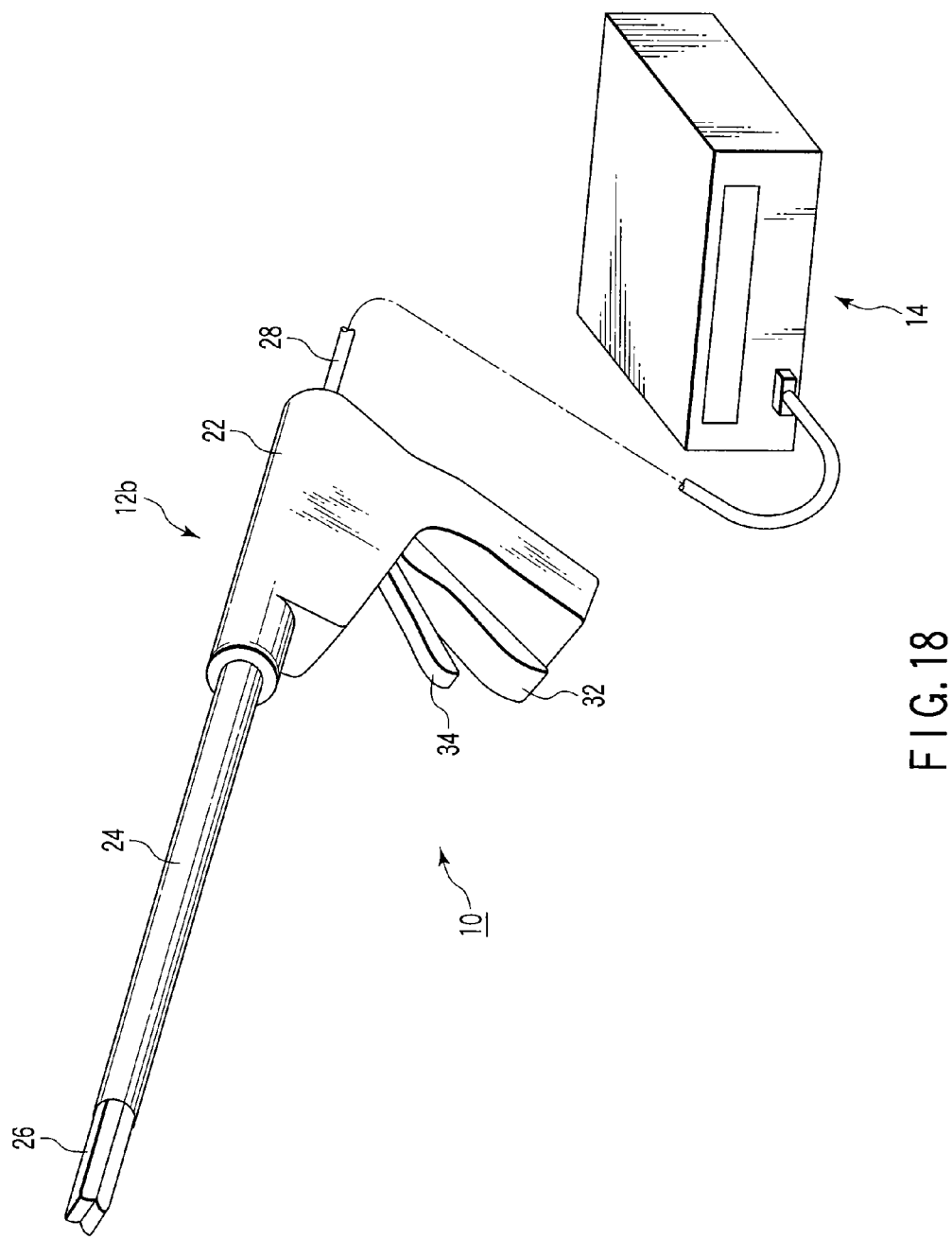
F I G. 18

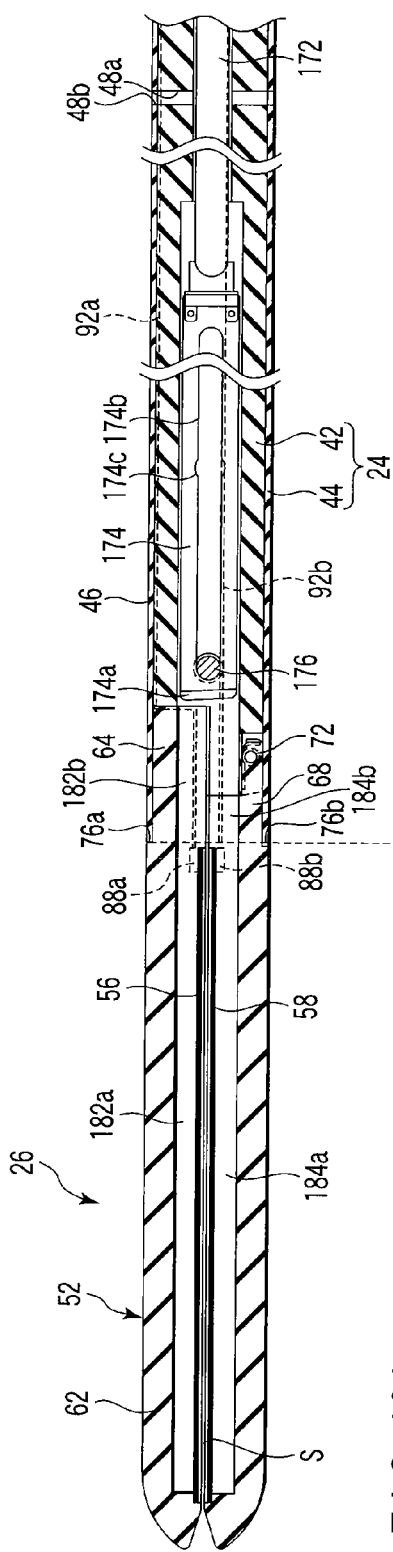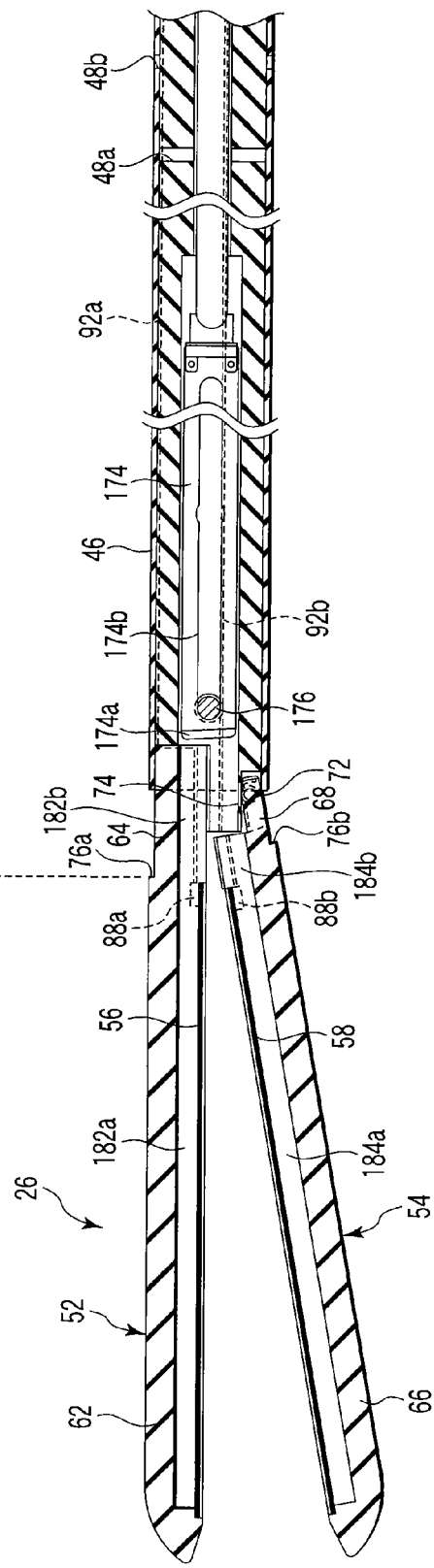
FIG. 19A
FIG. 19B

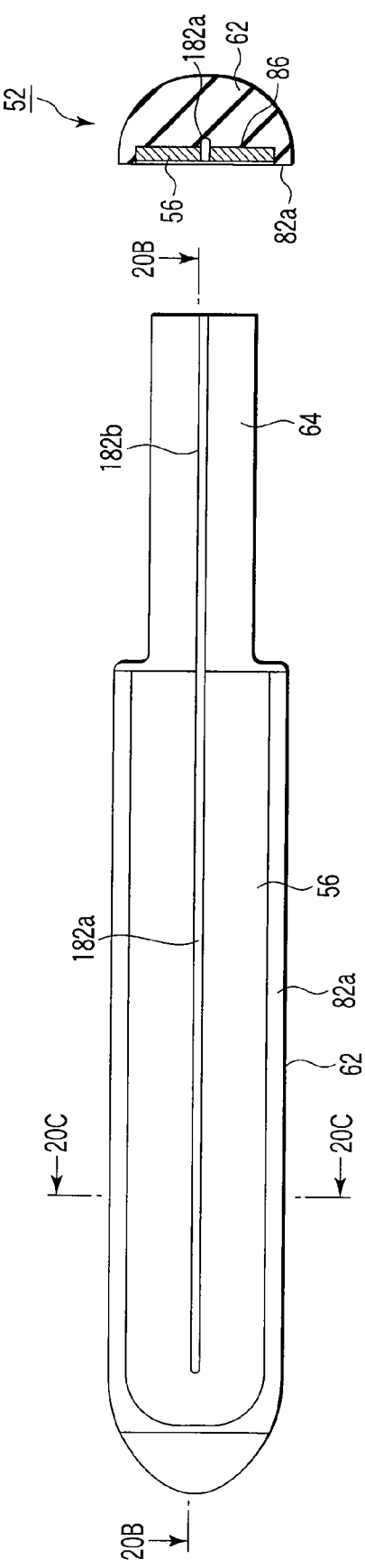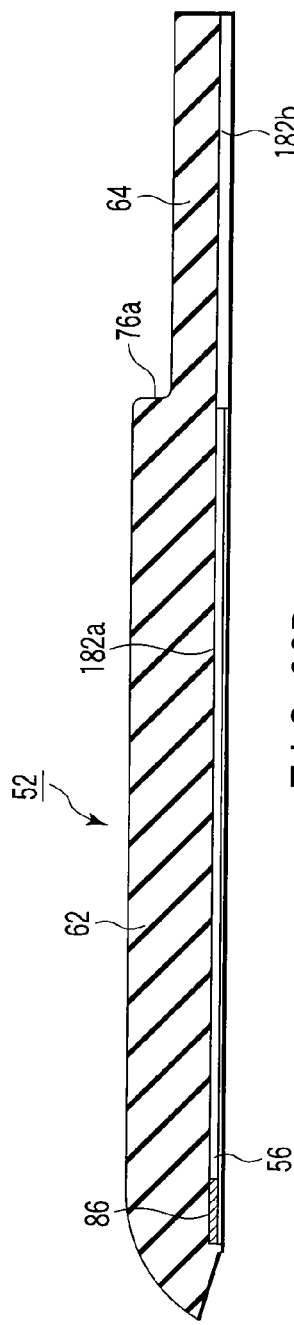
FIG. 20A  FIG. 20B  FIG. 20C

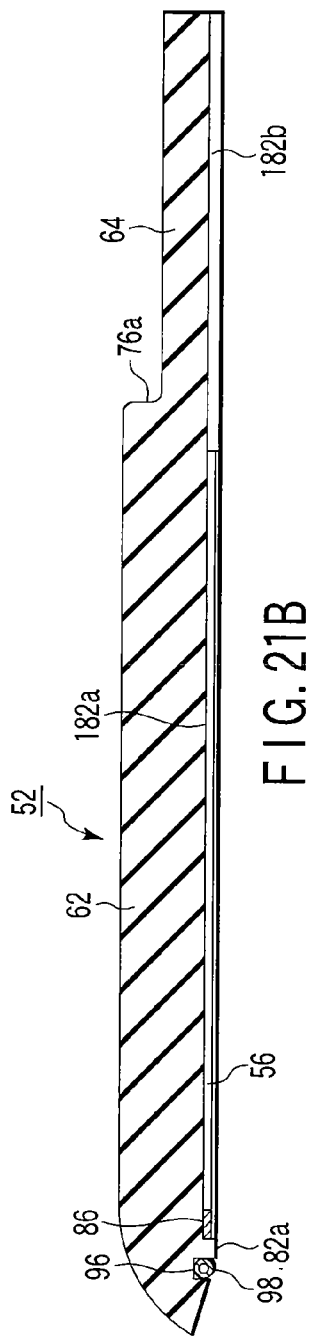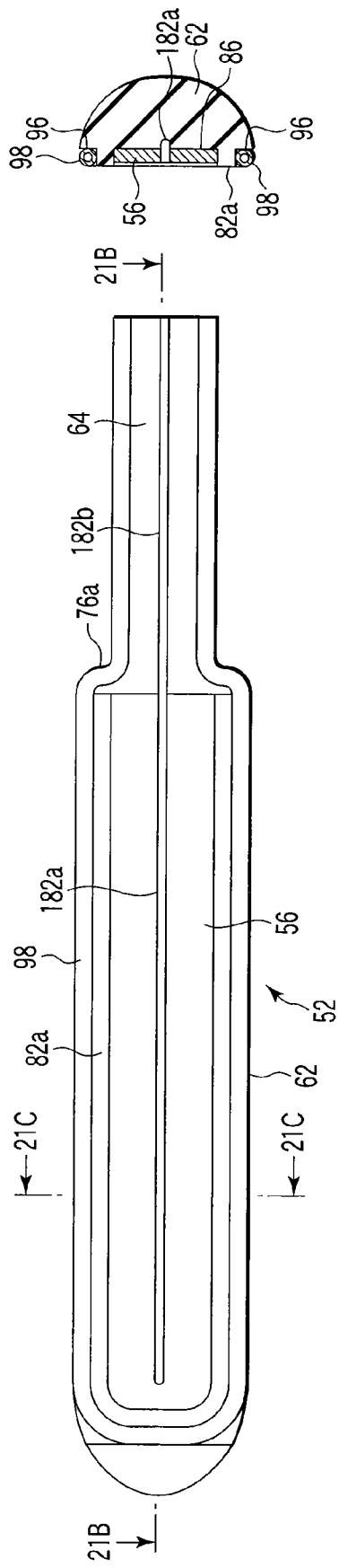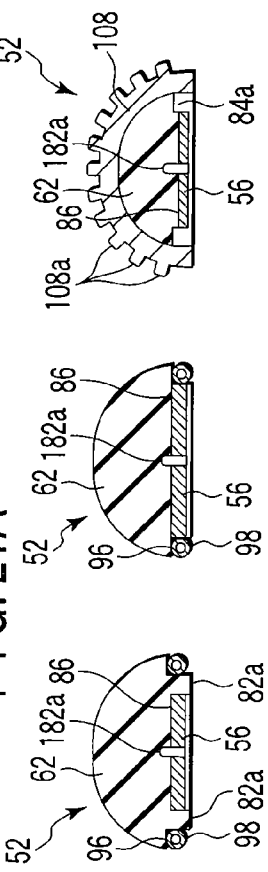

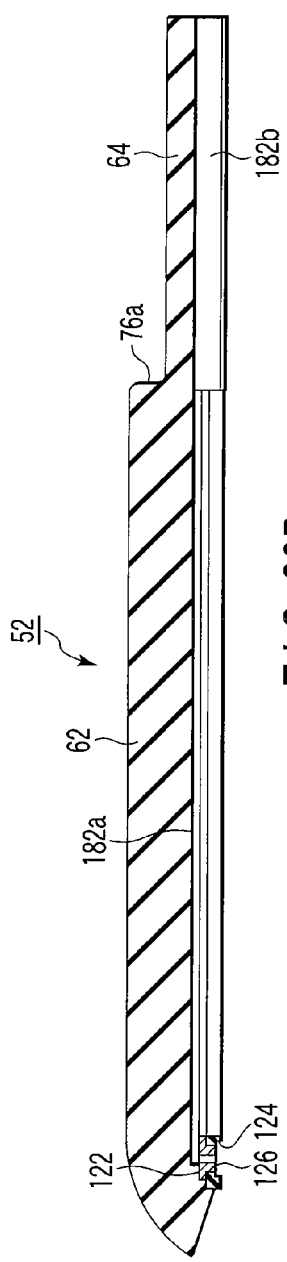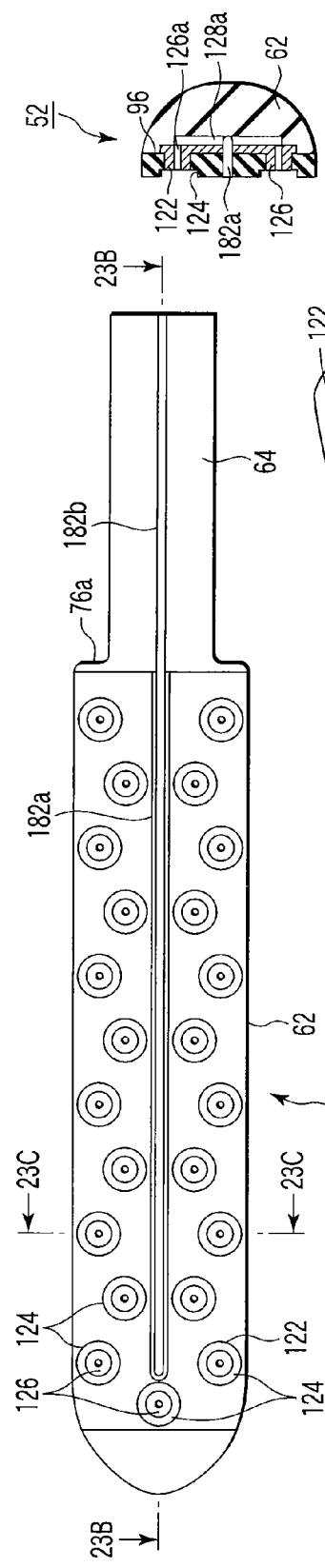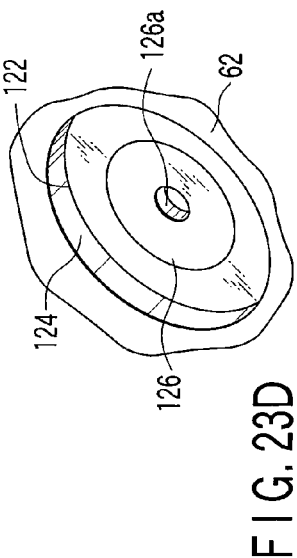

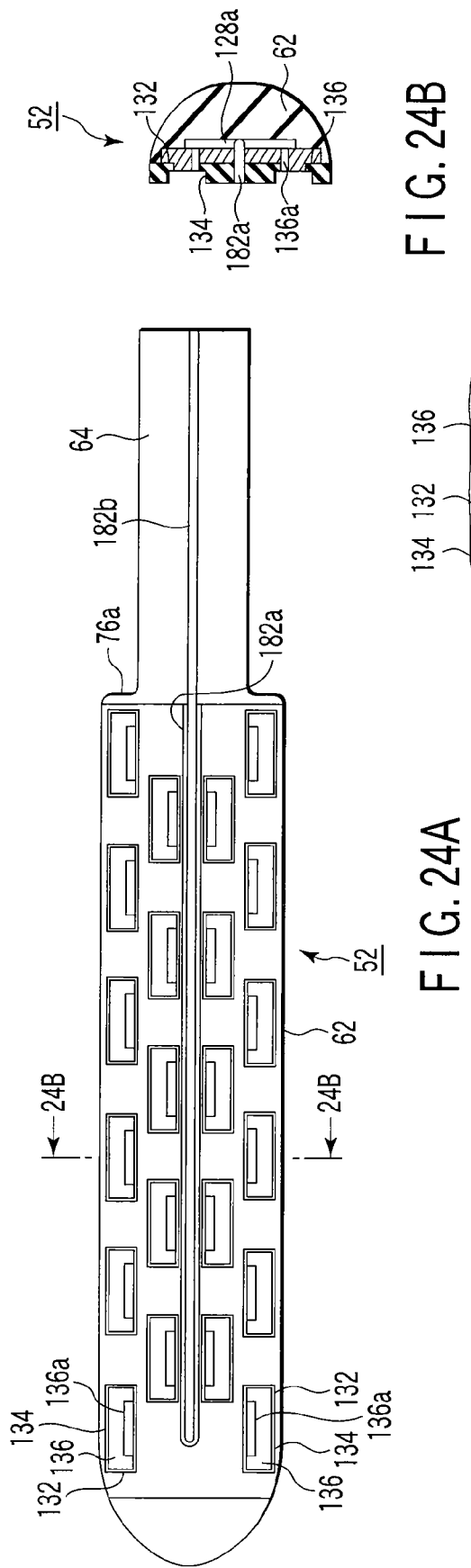
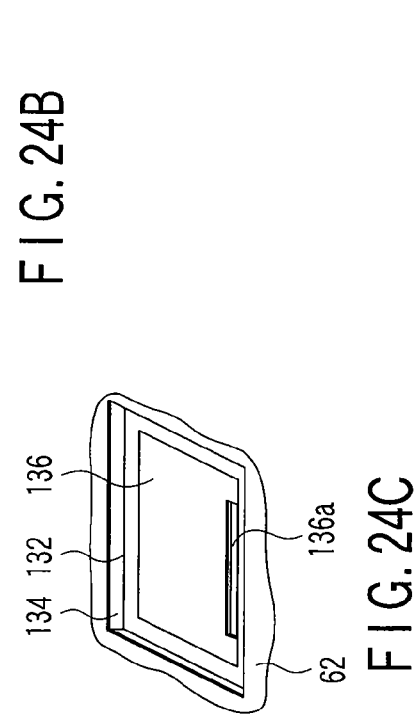
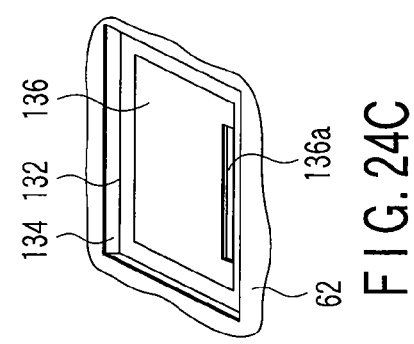
FIG. 24A
FIG. 24B
FIG. 24C

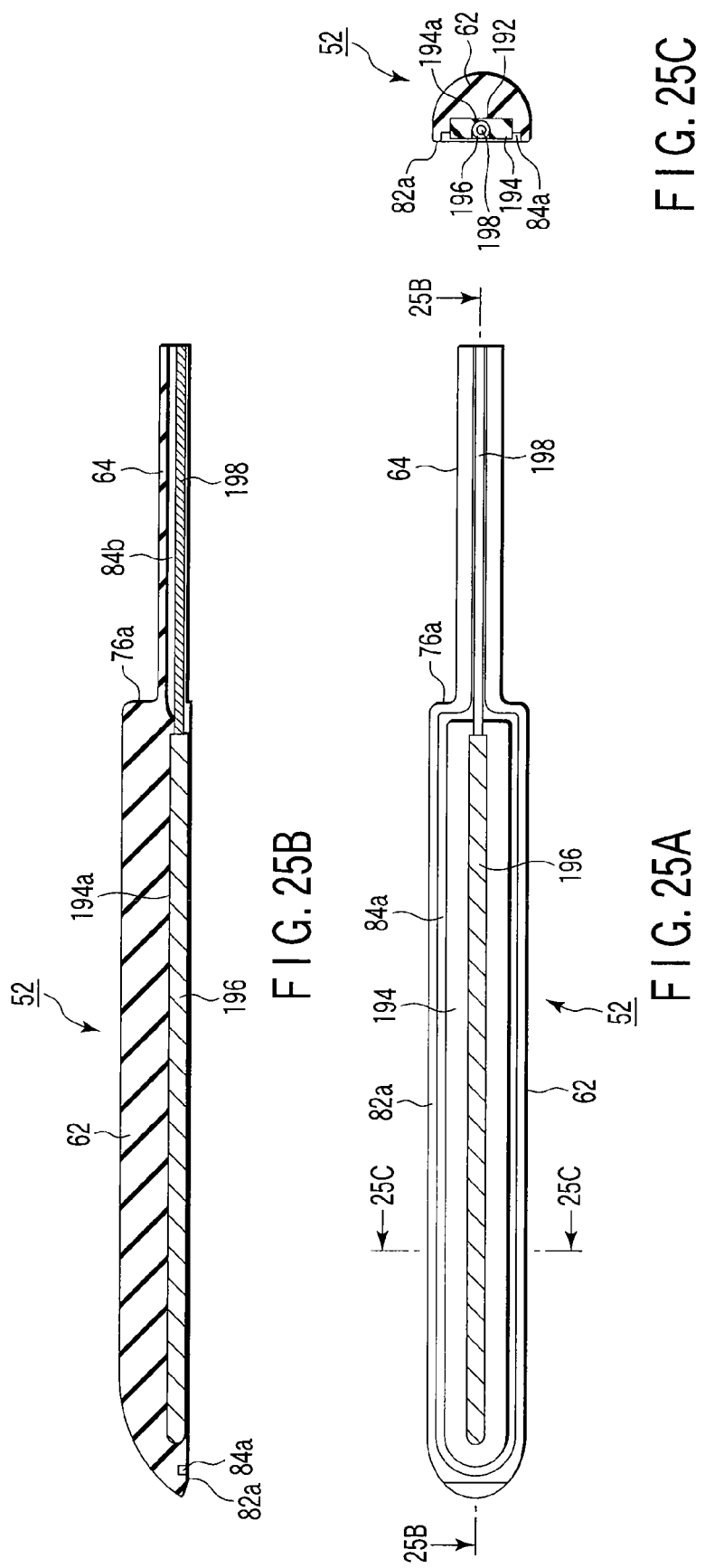

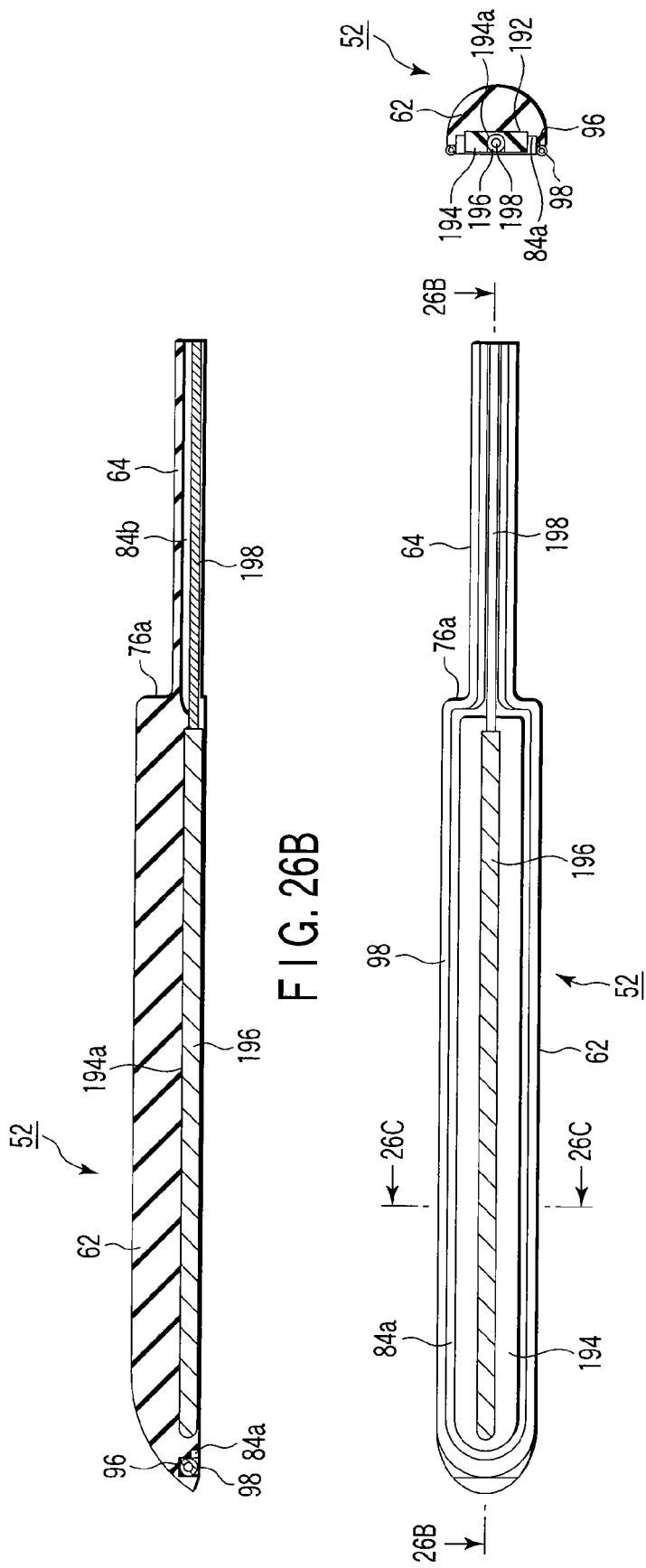

CURATIVE TREATMENT SYSTEM, CURATIVE TREATMENT DEVICE, AND TREATMENT METHOD FOR LIVING TISSUE USING ENERGY

BACKGROUND OF THE INVENTION

1. Field of the Invention

This invention relates to a treatment system which applies energy to a living tissue while the living tissue is held, a treatment device, and a treatment method for a living tissue by use of energy.

2. Description of the Related Art

There are known various treatment devices for use methods such as an open type which extracts a tissue and the like from one's body to perform a treatment outside the body and a laparoscopic type which is inserted into an abdominal cavity (the body) through an abdominal wall to perform a treatment.

For example, EP1 372 505 B1 discloses an electro-surgical instrument reducing thermal spread. A mechanical barrier made of a compliant material is disposed around electrodes of an end effecter of the electro-surgical instrument. The barrier inhibits radiation of heat and diffusion of vapor from the surfaces of the electrodes. Therefore, the electro-surgical instrument can reduce the thermal spread to a living tissue around a living tissue which is a treatment target.

BRIEF SUMMARY OF THE INVENTION

According to a first aspect of the present invention, there is provided a treatment system which applies energy to a living tissue to perform a treatment. The treatment system includes:

an energy source which supplies the energy;

a pair of holding portions which hold the living tissue, at least one of the holding portions being configured to relatively move with respect to the other holding portion;

an output portion disposed on at least one of the pair of holding portions and connected with the energy source, the output portion being configured to generate a fluid including a gas and/or a liquid from the living tissue by the energy supplied from the energy source; and at least one first channel disposed at a position close to the output portion, the first channel being configured to pass the fluid generated from the living tissue.

According to a second aspect of the present invention, there is provided a treatment device which applies energy to a living tissue. The treatment device includes:

a holding section which holds the living tissue, the holding section including:

first and second holding portions which relatively move with respect to each other;

an output portion disposed on at least one of the first holding portion and the second holding portion and connected with an energy source, the output portion being configured to generate a fluid including a gas and/or a liquid from the living tissue by the energy supplied from the energy source at a time when the living tissue is held between the first holding portion and the second holding portion; and a first channel disposed on the holding portion provided with the output portion in at least one of the first and second holding portions, the first channel being disposed at a position close to the output portion and being configured to allow the fluid generated from the living tissue to lead on the first channel.

According to a third aspect of the present invention, there is provided a treatment method for a living tissue by use of energy. The treatment method includes:

holding the living tissue;

supplying the energy to the held living tissue;

guiding, in a predetermined direction, a fluid including a gas and/or a liquid generated from the held living tissue in response to the energy supplied to the held living tissue; and discharging the generated fluid at a position away from the held living tissue.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a schematic longitudinal sectional view showing a shaft and a state where a first holding portion and a second holding portion of a holding section are closed in an electro-surgical device according to the first embodiment;

FIG. 2B is a schematic longitudinal sectional view showing the shaft and a state where the second holding portion of the holding section are opened with respect to the first holding portion in the electro-surgical device according to the first embodiment;

FIG. 3A is a schematic plan view showing the first holding portion on a side close to the second holding portion in the holding section of the electro-surgical device according to the first embodiment;

FIG. 3B is a schematic longitudinal sectional view cut along the 3B-3B line of FIG. 3A, showing the first holding portion of the holding section of the electro-surgical device according to the first embodiment;

FIG. 3C is a schematic cross sectional view cut along the 3C-3C line of FIG. 3A, showing the first holding portion and the second holding portion of the holding section of the electro-surgical device according to the first embodiment;

FIG. 5A is a schematic cross sectional view cut along the 3C-3C line of FIG. 3A, showing a modification of the first holding portion of the holding section of the electro-surgical device according to the first embodiment;

FIG. 5B is a schematic cross sectional view cut along the 3C-3C line of FIG. 3A, showing a modification of the first holding portion of the holding section of the electro-surgical device according to the first embodiment;

FIG. 5C is a schematic cross sectional view cut along the 3C-3C line of FIG. 3A, showing a modification of the first and second holding portions of the holding section of the electro-surgical device according to the first embodiment;

FIG. 5D is a schematic cross sectional view cut along the 3C-3C line of FIG. 3A, showing a modification of the first and second holding portions of the holding section of the electro-surgical device according to the first embodiment;

FIG. 6A is a schematic plan view showing a first holding portion on a side close to a second holding portion in a holding section of an electro-surgical device according to a second embodiment;

FIG. 6B is a schematic longitudinal sectional view cut along the 6B-6B line of FIG. 6A, showing the first holding portion of the holding section of the electro-surgical device according to the second embodiment;

FIG. 6C is a schematic cross sectional view cut along the 6C-6C line of FIG. 6A, showing the first holding portion of the holding section of the electro-surgical device according to the second embodiment;

FIG. 7A is a schematic cross sectional view cut along the 6C-6C line of FIG. 6A, showing a modification of the first holding portion of the holding section of the electro-surgical device according to the second embodiment;

FIG. 7B is a schematic cross sectional view cut along the 6C-6C line of FIG. 6A, showing a modification of the first holding portion of the holding section of the electro-surgical device according to the second embodiment;

FIG. 7C is a schematic cross sectional view cut along the 6C-6C line of FIG. 6A, showing a modification of the first holding portion of the holding section of the electro-surgical device according to the second embodiment;

FIG. 7D is a schematic cross sectional view cut along the 6C-6C line of FIG. 6A, showing a modification of the first holding portion of the holding section of the electro-surgical device according to the second embodiment;

FIG. 8A is a schematic plan view showing a first holding portion on a side close to a second holding portion in a holding section of an electro-surgical device according to a third embodiment;

FIG. 8B is a schematic longitudinal sectional view cut along the 8B-8B line of FIG. 8A, showing the first holding portion of the holding section of the electro-surgical device according to the third embodiment;

FIG. 8C is a schematic cross sectional view cut along the 8C-8C line of FIG. 8A, showing the first holding portion of the holding section of the electro-surgical device according to the third embodiment;

FIG. 9A is a schematic plan view showing a first holding portion on a side close to a second holding portion in a holding section of an electro-surgical device according to a fourth embodiment;

FIG. 9B is a schematic longitudinal sectional view cut along the 9B-9B line of FIG. 9A, showing the first holding portion of the holding section of the electro-surgical device according to the fourth embodiment;

FIG. 9C is a schematic cross sectional view cut along the 9C-9C line of FIG. 9A, showing the first holding portion of the holding section of the electro-surgical device according to the fourth embodiment;

FIG. 10A is a schematic plan view showing a first holding portion on a side close to a second holding portion in a holding section of an electro-surgical device according to a fifth embodiment;

FIG. 10B is a schematic longitudinal sectional view cut along the 10B-10B line of FIG. 10A, showing the first holding portion of the holding section of the electro-surgical device according to the fifth embodiment;

FIG. 10C is a schematic cross sectional view cut along the 10C-10C line of FIG. 10A, showing the first holding portion of the holding section of the electro-surgical device according to the fifth embodiment;

FIG. 10D is a schematic perspective view showing a barrier portion and a high-frequency electrode arranged at an electrode arrangement portion of the first holding portion in the holding section of the electro-surgical device according to the fifth embodiment;

FIG. 11A is a schematic plan view showing a first holding portion on a side close to a second holding portion in a holding section of an electro-surgical device according to a sixth embodiment;

FIG. 11B is a schematic longitudinal sectional view cut along the 11B-11B line of FIG. 11A, showing the first holding portion of the holding section of the electro-surgical device according to the sixth embodiment;

FIG. 11C is a schematic cross sectional view cut along the 11C-11C line of FIG. 11A, showing the first holding portion of the holding section of the electro-surgical device according to the sixth embodiment;

FIG. 11D is a schematic perspective view showing a barrier portion and a high-frequency electrode arranged at an electrode arrangement portion of the first holding portion in the holding section of the electro-surgical device according to the sixth embodiment;

FIG. 12A is a schematic plan view showing a first holding portion on a side close to a second holding portion in a holding section of an electro-surgical device according to a seventh embodiment;

FIG. 12B is a schematic longitudinal sectional view cut along the 12B-12B line of FIG. 12A, showing the first holding portion of the holding section of the electro-surgical device according to the seventh embodiment;

FIG. 12C is a schematic cross sectional view cut along the 12C-12C line of FIG. 12A, showing the first holding portion of the holding section of the electro-surgical device according to the seventh embodiment;

FIG. 12D is a schematic perspective view showing a barrier portion and a high-frequency electrode arranged at an electrode arrangement portion of the first holding portion in the holding section of the electro-surgical device according to the seventh embodiment;

FIG. 13A is a schematic plan view showing a first holding portion on a side close to a second holding portion in a holding section of an electro-surgical device according to an eighth embodiment;

FIG. 13B is a schematic longitudinal sectional view cut along the 13B-13B line of FIG. 13A, showing the first holding portion of the holding section of the electro-surgical device according to the eighth embodiment;

FIG. 13C is a schematic cross sectional view cut along the 13C-13C line of FIG. 13A, showing the first holding portion of the holding section of the electro-surgical device according to the eighth embodiment;

FIG. 13D is a schematic perspective view showing a barrier portion and a high-frequency electrode arranged at an electrode arrangement portion of the first holding portion in the holding section of the electro-surgical device according to the eighth embodiment;

FIG. 14A is a schematic plan view showing a first holding portion on a side close to a second holding portion in a holding section of an electro-surgical device according to a ninth embodiment;

FIG. 14B is a schematic longitudinal sectional view cut along the 14B-14B line of FIG. 14A, showing the first holding portion of the holding section of the electro-surgical device according to the ninth embodiment;

FIG. 14C is a schematic cross sectional view cut along the 14B-14B line of FIG. 14A, showing a modification of the first holding portion of the holding section of the electro-surgical device according to the ninth embodiment;

FIG. 16A is a schematic plan view showing a first holding portion on a side close to a second holding portion in a holding section of an electro-surgical device according to an eleventh embodiment;

FIG. 16B is a schematic longitudinal sectional view cut along the 16B-16B line of FIG. 16A, showing the first and second holding portions of the holding section of the electro-surgical device according to the eleventh embodiment;

FIG. 16C is a schematic longitudinal sectional view cut along the 16B-16B line of FIG. 16A, showing distal ends of main bodies of the first and second holding portions in the holding section of the electro-surgical device according to the eleventh embodiment;

FIG. 17A is a schematic plan view showing a first holding portion on a side close to a second holding portion in a holding section of an electro-surgical device according to a twelfth embodiment;

FIG. 17B is a schematic longitudinal sectional view cut along the 17B-17B line of FIG. 17A, showing the first and second holding portions of the holding section of the electro-surgical device according to the twelfth embodiment;

FIG. 17C is a schematic longitudinal sectional view cut along the 17B-17B line of FIG. 17A, showing distal ends of main bodies of the first and second holding portions in the holding section of the electro-surgical device according to the twelfth embodiment;

FIG. 18 is a schematic diagram showing a treatment system according to a thirteenth embodiment of the present invention;

FIG. 19A is a schematic longitudinal sectional view showing a shaft and a state where a first holding portion and a second holding portion of a holding section are closed in an electro-surgical device according to the thirteenth embodiment;

FIG. 19B is a schematic longitudinal sectional view showing the shaft and a state where the second holding portion of the holding section are opened with respect to the first holding portion in the electro-surgical device according to the thirteenth embodiment;

FIG. 20A is a schematic plan view showing a first holding portion on a side close to the second holding portion in the holding section of the electro-surgical device according to the thirteenth embodiment;

FIG. 20B is a schematic longitudinal sectional view cut along the 20B-20B line of FIG. 20A, showing the first holding portion of the holding section of the electro-surgical device according to the thirteenth embodiment;

FIG. 20C is a schematic cross sectional view cut along the 20C-20C line of FIG. 20A, showing the first holding portion of the holding section of the electro-surgical device according to the thirteenth embodiment;

FIG. 21A is a schematic plan view showing a first holding portion on a side close to the second holding portion in the holding section of the electro-surgical device according to the fourteenth embodiment;

FIG. 21B is a schematic longitudinal sectional view cut along the 21B-21B line of FIG. 21A, showing the first holding portion of the holding section of the electro-surgical device according to the fourteenth embodiment;

FIG. 21C is a schematic cross sectional view cut along the 21C-21C line of FIG. 21A, showing the first holding portion of the holding section of the electro-surgical device according to the fourteenth embodiment;

FIG. 22A is a schematic cross sectional view cut along the 21C-21C line of FIG. 21A, showing a modification of the first holding portion of the holding section of the electro-surgical device according to the fourteenth embodiment;

FIG. 22B is a schematic cross sectional view cut along the 21C-21C line of FIG. 21A, showing a modification of the first holding portion of the holding section of the electro-surgical device according to the fourteenth embodiment;

FIG. 22C is a schematic cross sectional view cut along the 21C-21C line of FIG. 21A, showing a modification of the first holding portion of the holding section of the electro-surgical device according to the fourteenth embodiment;

FIG. 22D is a schematic cross sectional view cut along the 21C-21C line of FIG. 21A, showing a modification of the first holding portion of the holding section of the electro-surgical device according to the fourteenth embodiment;

FIG. 23A is a schematic plan view showing a first holding portion on a side close to a second holding portion in a holding section of an electro-surgical device according to a fifteenth embodiment;

FIG. 23B is a schematic longitudinal sectional view cut along the 23B-23B line of FIG. 23A, showing the first holding portion of the holding section of the electro-surgical device according to the fifteenth embodiment;

FIG. 23C is a schematic cross sectional view cut along the 23C-23C line of FIG. 23A, showing the first holding portion of the holding section of the electro-surgical device according to the fifteenth embodiment;

FIG. 23D is a schematic perspective view showing a barrier portion and a high-frequency electrode arranged at an electrode arrangement portion of the first holding portion in the holding section of the electro-surgical device according to the fifteenth embodiment;

FIG. 24A is a schematic plan view showing a first holding portion on a side close to a second holding portion in a holding section of an electro-surgical device according to a sixteenth embodiment;

FIG. 24B is a schematic longitudinal sectional view cut along the 24B-24B line of FIG. 24A, showing the first holding portion of the holding section of the electro-surgical device according to the sixteenth embodiment;

FIG. 24C is a schematic perspective view showing a barrier portion and a high-frequency electrode disposed at an electrode arrangement portion of the first holding portion of the holding section of the electro-surgical device according to the sixteenth embodiment;

FIG. 25A is a schematic plan view showing a first holding portion on a side close to a second holding portion of a holding section of a laser treatment device according to a seventeenth embodiment;

FIG. 25B is a schematic longitudinal sectional view cut along the 25B-25B line of FIG. 25A, showing the first holding portion of the holding section of the laser treatment device according to the seventeenth embodiment;

FIG. 25C is a schematic cross sectional view cut along the 25C-25C line of FIG. 25A, showing the first holding portion of the holding section of the laser treatment device according to the seventeenth embodiment;

FIG. 26A is a schematic plan view showing a first holding portion on a side close to a second holding portion of a holding section of a laser treatment device according to an eighteenth embodiment;

FIG. 26B is a schematic longitudinal sectional view cut along the 26B-26B line of FIG. 26A, showing the first holding portion of the holding section of the laser treatment device according to the eighteenth embodiment;

FIG. 26C is a schematic cross sectional view cut along the 26C-26C line of FIG. 26A, showing the first holding portion of the holding section of the laser treatment device according to the eighteenth embodiment;

DETAILED DESCRIPTION OF THE INVENTION

The best mode for carrying out this invention will hereinafter be described with reference to the drawings.

First Embodiment

A first embodiment will be described with reference to FIGS. 1 to 5D.

Here, as an example of an energy treatment device, a linear type bipolar electro-surgical device 12 which performs a treatment through, for example, an abdominal wall will be described.

Figure 1:
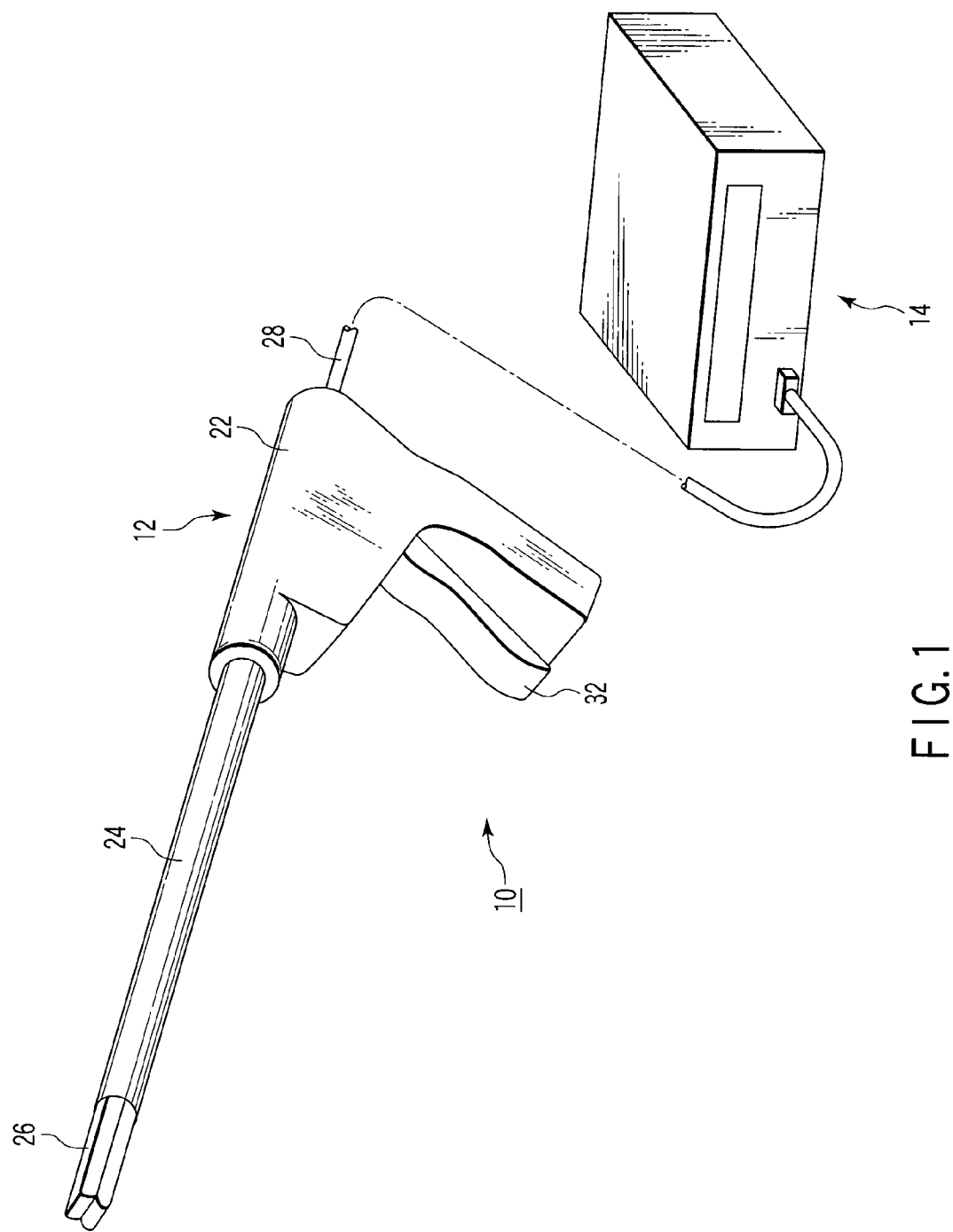
FIG. 1 is a schematic diagram showing a treatment system according to a first embodiment of the present invention.

As shown in FIG. 1, a treatment system 10 includes the electro-surgical device (a treatment device for curing) 12 and an energy source 14.

The electro-surgical device 12 includes a handle 22, a shaft 24 and an openable/closable holding section 26. The handle 22 is connected with the energy source 14 via a cable 28. The energy source 14 is connected to a foot switch and a handle switch (not shown). Therefore, these foot and hand switches are operated by an operator to switch ON/OFF of the supply of energy from the energy source 14 to the electro-surgical device 12.

The handle 22 is substantially formed into an L-shape. The shaft 24 is disposed on one end of the handle 22. The cable 28 is extended from a proximal side of the handle 22 disposed coaxially with the shaft 24.

On the other hand, the other end of the handle 22 is a grip held by the operator. The handle 22 includes a holding section opening/closing knob 32 arranged on the other end of the handle 22. The holding section opening/closing knob 32 is connected with a proximal end of a sheath 44 described later of the shaft 24 substantially at the center of the handle 22. When the holding section opening/closing knob 32 is allowed to come close to or come away from the other end of the handle 22, the sheath 44 moves along an axial direction of the shaft 24.

As shown in FIGS. 2A and 2B, the shaft 24 includes a cylindrical member 42 and the sheath 44 slidably disposed outside the cylindrical member 42. A proximal end of the cylindrical member 42 is fixed to the handle 22. The sheath 44 is slidable along an axial direction of the cylindrical member 42.

Outside the cylindrical member 42, concave portion 46 is formed along the axial direction of the cylindrical member 42. The concave portion 46 is provided with a first conducting line 92a connected to a first high-frequency electrode 56 described later. A second conducting line 92b connected to a second high-frequency electrode 58 described later is passed through the cylindrical member 42.

Furthermore, the cylindrical member 42 and the sheath 44 of the shaft 24 are provided with fluid discharge ports 48a, 48b from which a fluid such as a vapor (a gas) or a liquid (a tissue liquid) (described later) is discharged. The fluid discharge ports 48a, 48b are formed on a proximal end of the shaft 24.

Here, a connection mouthpiece (not shown) may be disposed at the fluid discharge port 48b of the sheath 44. At this time, the fluid discharged later is discharged through a first fluid discharge groove 84a, a second fluid discharge groove 84b and the connection mouthpiece. In this case, when a fluid such as the vapor or the liquid is sucked through the connection mouthpiece, the fluid can easily be discharged from the fluid discharge ports 48a, 48b.

It is to be noted that it is preferable that the fluid discharge ports 48a, 48b are arranged at the shaft 24, but it is preferable that the ports are arranged at the handle 22 instead of the shaft 24.

As shown in FIGS. 1 to 2B, the holding section 26 is disposed at a distal end of the shaft 24. As shown in FIGS. 2A and 2B, the holding section 26 includes a first holding portion 52, a second holding portion 54, the first high-frequency electrode 56 as an output portion or an energy emitting portion, and the second high-frequency electrode 58 as another output portion or another energy emitting portion.

It is preferable that the first holding portion 52 and the second holding portion 54 entirely have insulating properties, respectively. Especially, surrounding areas of an electrode arrangement portion 86 described later are formed so as to have the insulating properties.

The first holding portion 52 integrally includes a first holding portion main body (hereinafter referred to mainly as the main body) 62 provided with the first high-frequency electrode 56 and a base portion 64 disposed at a proximal end of the main body 62. The second holding portion 54 integrally includes a second holding portion main body 66 provided with the second high-frequency electrode 58 and a base portion 68 disposed at a proximal end of the main body 66.

The base portion 64 of the first holding portion 52 is fixed to a distal end of the cylindrical member 42 of the shaft 24. On the other hand, the base portion 68 of the second holding portion 54 is rotatably supported at the distal end of the cylindrical member 42 of the shaft 24 by a support pin 72 disposed in a direction crossing the axial direction of the shaft 24 at right angles. The second holding portion 54 can rotate around an axis of the support pin 72 to open or close with respect to the first holding portion 52. Moreover, the second holding portion 54 is urged so as to open with respect to the first holding portion 52 by an elastic member 74 such as a leaf spring.

As shown in FIGS. 3B and 3C, outer surfaces of the main bodies 62 and 66 of the first holding portion 52 and the second holding portion 54 are formed into smooth curved surfaces. Similarly, outer surfaces of the base portions 64 and 68 of the first holding portion 52 and the second holding portion 54 are also formed into smooth curved surfaces. While the second holding portion 54 is closed with respect to the first holding portion 52, sections of the main bodies 62, 66 of the holding portions 52, 54 are formed into substantially circular or elliptic shapes, respectively, as shown in FIG. 3C. When the second holding portion 54 is closed with respect to the first holding portion 52, the base portions 64, 68 are formed into cylindrical shapes. In this state, a diameter of each of the proximal ends of the main bodies 62, 66 of the first holding portion 52 and the second holding portion 54 is formed to be larger than a diameter of each of the base portions 64, 68. Moreover, stepped portions 76a, 76b are formed between the main bodies 62, 66 and the base portions 64, 68, respectively.

Here, in the first holding portion 52 and the second holding portion 54, while the second holding portion 54 is closed with respect to the first holding portion 52, a substantially circular or elliptic outer peripheral surface formed by combining the base portions 64, 68 of the holding portions 52, 54 is substantially the same plane as that of an outer peripheral surface of the distal end of the cylindrical member 42, or a diameter of the outer peripheral surface is formed to be slightly larger than that of the outer peripheral surface of the distal end of the cylindrical member 42. Therefore, the sheath 44 can be slid with respect to the cylindrical member 42 to cover the base portions 64, 68 of the first holding portion 52 and the second holding portion 54 with a distal end of the sheath 44. In this state, as shown in FIG. 2A, the first holding portion 52 and the second holding portion 54 close against an urging force of the elastic member 74. On the other hand, the sheath 44 is slid toward the proximal end of the cylindrical member 42 from the state in which the base portions 64, 68 of the first holding portion 52 and the second holding portion 54 are covered with the distal end of the sheath 44. In this case, as shown in FIG. 2B, the second holding portion 54 is opened with respect to the first holding portion 52 by the urging force of the elastic member 74.

As shown in FIGS. 3B and 3C, on a side of the main body 62 of the first holding portion 52 close to the main body 66 of the second holding portion 54, the surface (hereinafter referred to as a contact surface) of an edge portion (a barrier portion) 82a which comes into contact with a living tissue is formed into, for example, a flat shape. As shown in FIGS. 3A to 3C, the first fluid discharge groove (a first channel) 84a opened as a channel of a fluid such as a vapor or a high-temperature liquid is formed on an inner side of the edge portion 82a of the first holding portion 52. The first fluid discharge groove 84a is formed into an annular shape so as to have a concave section. Moreover, the base portion 64 of the first holding portion 52 is provided with the second fluid discharge groove 84b opened as a channel of a fluid such as a vapor or a liquid and formed so as to have a concave section. The second fluid discharge groove 84b is formed continuously from the first fluid discharge groove 84a along the axial direction of the shaft 24.

On an inner side of the first fluid discharge groove 84a formed in the main body 62, the electrode arrangement portion 86 is formed as a seat on which the first high-frequency electrode 56 is disposed. The electrode arrangement portion 86 is present at a position lower than that of the contact surface of the edge portion 82a of the main body 62. That is, the electrode arrangement portion 86 is formed into a recessed state with respect to the edge portion 82a of the main body 62.

A contact surface between the plate-like first high-frequency electrode 56 and the living tissue, which faces the second holding portion 54, is formed into a flat surface, and the first high-frequency electrode 56 is fixed to the electrode arrangement portion 86. For example, a proximal end of the first high-frequency electrode 56 on a side opposite to a side facing the second holding portion 54 is electrically connected with a first electrode connector 88a. The first electrode connector 88a is connected with the cable 28 extended from the handle 22 via the first conducting line 92a.

Moreover, in a state in which the first high-frequency electrode 56 is disposed at the electrode arrangement portion 86 of the main body 62 of the first holding portion 52, as shown in FIGS. 3B and 3C, the contact surface of the edge portion 82a of the first holding portion 52 is protruded from the surface of the first high-frequency electrode 56. That is, the contact surface of the edge portion 82a of the first holding portion 52 is present at a position higher than that of the surface of the first high-frequency electrode 56. A height difference between the contact surface and the surface is appropriately set to, for example, about 0.5 mm.

It is to be noted that, although not shown, the main body 66 and the second high-frequency electrode 58 of the second holding portion 54 are formed symmetrically with respect to the main body 62 and the first high-frequency electrode 56 of the first holding portion 52. Therefore, when the second holding portion 54 is closed with respect to the first holding portion 52, the edge portion 82a of the main body 62 of the first holding portion 52 and the edge portion 82b of the main body 66 of the second holding portion 54 abut on each other (see FIG. 3C), but a space S is formed between the first high-frequency electrode 56 and the second high-frequency electrode 58 as shown in FIG. 2A.

Next, a function of the treatment system 10 according to this embodiment will be described.

As shown in FIG. 2A, while the second holding portion 54 is closed with respect to the first holding portion 52, the holding section 26 and the shaft 24 of the electro-surgical device 12 are inserted into an abdominal cavity through the abdominal wall. The holding section 26 of the electro-surgical device 12 is opposed to the living tissue which is a treatment target.

When the living tissue as the treatment target is grasped between the first holding portion 52 and the second holding portion 54, the holding section opening/closing knob 32 of the handle 22 is operated. At this time, the sheath 44 is moved toward a proximal side of the shaft 24 on the cylindrical member 42. A cylindrical shape cannot be maintained between the base portions 64 and 68 owing to the urging force of the elastic member 74, and the second holding portion 54 opens from the first holding portion 52.

Moreover, the living tissue which is the treatment target is disposed between the first high-frequency electrode 56 of the first holding portion 52 and the second high-frequency electrode 58 of the second holding portion 54. In this state, the holding section opening/closing knob 32 of the handle 22 is operated. At this time, the sheath 44 is moved toward a distal side of the shaft 24 with respect to the cylindrical member 42. The base portions 64, 68 are closed by the sheath 44 against the urging force of the elastic member 74 to form the cylindrical shape between the base portions 64, 68. In consequence, the first holding portion main body 62 formed integrally with the base portion 64 and the second holding portion main body 66 formed integrally with the base portion 68 are closed. That is, the second holding portion 54 is closed with respect to the first holding portion 52. In consequence, the living tissue as the treatment target is held between the first holding portion 52 and the second holding portion 54.

At this time, the living tissue of the treatment target comes into contact with both of the first high-frequency electrode 56 disposed at the first holding portion 52 and the second high-frequency electrode 58 disposed at the second holding portion 54. A peripheral tissue of the living tissue of the treatment target comes into close contact with both of the contact surface of the edge portion 82a of the first holding portion 52 and a contact surface of the edge portion 82b of the second holding portion 54.

In this state, the foot switch and the hand switch are operated. The energy source 14 supplies energy to the first high-frequency electrode 56 and the second high-frequency electrode 58 via the cable 28, the first and second conducting lines 92a, 92b and the first and second conducting connectors 88a, 88b.

Between the first high-frequency electrode 56 and the second high-frequency electrode 58, a high-frequency current is conducted via the living tissue of the treatment target. In consequence, the living tissue grasped between the first high-frequency electrode 56 and the second high-frequency electrode 58 is heated.

At this time, since the heated portion of the living tissue includes a liquid component (a moisture), a fluid, for example, a high-temperature vapor or a liquid such as a body liquid (a tissue liquid) at normal temperature to high temperature is generated.

Here, when the first high-frequency electrode 56 is fixed to the electrode arrangement portion 86 of the main body 62 of the first holding portion 52, the surface of the first high-frequency electrode 56 exposed on a second holding portion 54 side is present at a position slightly lower than that of the contact surface of the edge portion 82a of the first holding portion 52. Similarly, when the second high-frequency electrode 58 is fixed to the electrode arrangement portion 86 of the main body 66 of the second holding portion 54, the surface of the second high-frequency electrode 58 exposed on a first holding portion 52 side is present at a position slightly lower than that of the contact surface of the edge portion 82b of the second holding portion 54. Therefore, a fluid such as the vapor or the liquid generated from the living tissue hits inner surfaces of the edge portion 82a of the first holding portion 52 and the edge portion 82b of the second holding portion 54. At this time, since the contact surfaces of the edge portions 82a, 82b come into close contact with the peripheral tissue of the living tissue of the treatment target, the inner surfaces of the edge portions 82a, 82b perform functions of the barrier portions (dams) in which a fluid such as the vapor or the liquid is prevented from leaking to the outside.

In this case, a fluid such as the vapor or the liquid generated from the living tissue hits the inner surfaces of the edge portions 82a, 82b of the main bodies 62, 66 of the first holding portion 52 and the second holding portion 54, and leads on the first fluid discharge groove 84a. Moreover, the fluid flows toward the second fluid discharge groove 84b of the base portions 64, 68 of the first holding portion 52 and the second holding portion 54, which communicates with the first fluid discharge groove 84a.

The fluid further leads on the cylindrical member 42 from the second fluid discharge groove 84b of the base portions 64, 68 of the first holding portion 52 and the second holding portion 54. Moreover, the fluid is derived from the shaft 24 through the fluid discharge port 48a of the cylindrical member 42 and the fluid discharge port 48b of the sheath 44.

To end the treatment, the operation of the foot switch or the hand switch is stopped. In this case, the supply of the energy from the energy source 14 to the first high-frequency electrode 56 and the second high-frequency electrode 58 stops.

As described above, according to this embodiment, the following effects are obtained.

When the electro-surgical device 12 applies the high-frequency current to the living tissue of the treatment target held by the holding section 26, the contact surface of the edge portion 82a of the first holding portion 52 and the contact surface of the edge portion 82b of the second holding portion 54 can be brought into close contact with the living tissue, respectively. Therefore, even if a fluid such as the vapor or the liquid generated from the living tissue of the treatment target flows toward the edge portion 82a of the first holding portion 52 and the edge portion 82b of the second holding portion 54, the fluid can be introduced into the first fluid discharge groove 84a on inner sides of these edge portions 82a, 82b.

That is, in a case where the first high-frequency electrode 56 does not come into contact with the second high-frequency electrode 58 and the living tissue is grasped between the first holding portion 52 and the second holding portion 54, when the edge portions 82a, 82b come into close contact with the living tissue, the edge portions 82a, 82b do not have to be arranged as the barrier portions. Even in this case, the fluid can be introduced into the first fluid discharge groove 84a.

In this case, the fluid generated from the living tissue of the treatment target can be discharged from the electro-surgical device 12 through the first fluid discharge grooves 84a formed between the first high-frequency electrode 56 and the edge portion 82a of the first holding portion 52 and between the second high-frequency electrode 58 and the edge portion 82b of the second holding portion 54, the second fluid discharge grooves 84b of the base portions 64, 68 of the holding section 26, the fluid discharge port 48a of the cylindrical member 42 of the shaft 24 and the fluid discharge port 48b of the sheath 44. Therefore, a fluid such as the vapor or the liquid can be prevented from leaking around the living tissue held by the holding section 26. In consequence, it can be prevented that the peripheral tissue other than the target tissue is influenced by the vapor generated from the portion to which the high-frequency current has been conducted during the treatment of the living tissue. That is, the position influenced during the treatment of the living tissue can be limited to the living tissue to which the high-frequency current has been conducted between the first high-frequency electrode 56 and the second high-frequency electrode 58.

Therefore, according to this embodiment, unlike EP1 372 505 B1 described above, when a fluid such as the vapor or the liquid (the high-temperature body liquid) generated from the living tissue is discharged, the living tissue around the living tissue of the treatment target can securely be prevented from being influenced by a fluid such as the vapor or the liquid (the body liquid).

As described above, it is important to guide a fluid such as the vapor or the liquid to a position where the fluid does not come into contact with the tissue, when inhibiting a thermal influence on the living tissue. It is possible to obtain an especially large effect that the thermal influence can be prevented from being exerted outside the holding section 26, in a case where the tissue is larger than the holding section 26 to such an extent that a surrounding area of the holding section 26 is covered. When an only small opening (space) is made in the holding section 26 but a fluid such as the vapor or the liquid leaks from the opening, the fluid is discharged from the opening, and the living tissue around the holding section 26 is thermally influenced.

Moreover, even when surrounding areas of the high-frequency electrodes (the energy emitting portions) 56, 58 are covered with the barrier portions 82a, 82b in order to eliminate such an opening, the opening is formed by a fluid pressure such as a generated vapor pressure, and the fluid might be discharged. Therefore, it is useful means to inhibit unnecessary discharge of the fluid due to a rise of the fluid pressure and dispose a channel (the first fluid discharge groove 84a) which guides and discharges the fluid in a predetermined direction.

Furthermore, as described above, the contact surfaces of the edge portions 82a, 82b are arranged as the barrier portions so that the contact surfaces are present at positions higher than the surfaces of the first and second high-frequency electrodes 56, 58, close contact properties between the living tissue and the edge portions 82a, 82b can be improved. Therefore, a fluid such as the vapor or the liquid can more securely be introduced into the first fluid discharge groove 84a.

It is to be noted that in this embodiment, it has been described that the surfaces of the high-frequency electrodes 56, 58 which come into close contact with the living tissue and the contact surfaces of the edge portions 82a, 82b are flat, but the surfaces may variously be changed to, for example, a corrugated surface, a curved surface or the like in accordance with a shape of the living tissue of the treatment target.

In this embodiment, the bipolar electro-surgical device 12 has been described in which the first holding portion 52 is provided with the first high-frequency electrode 56 and the second holding portion 54 is provided with the second high-frequency electrode 58. In addition, it is preferable that the present embodiment is similarly applied to a mono-polar electro-surgical device (not shown) in which the high-frequency electrode is disposed in, for example, the first holding portion 52 or the second holding portion 54 only or the holding portions 52, 54 are provided with electrodes of the same pole, respectively. That is, it is preferable that the first fluid discharge grooves 84a are similarly formed between the electrode as a holding surface and the edge portions 82a, 82b of the holding portions 52, 54.

In this embodiment, it has been described that the stepped portion 76a is disposed between the main body 62 and the base portion 64 of the first holding portion 52 and the stepped portion 76b is disposed between the main body 66 and the base portion 68 of the second holding portion 54. In addition, it is also preferable that, instead of arranging these stepped portions 76a, 76b, the main bodies 62, 66 and the base portions 64, 68 are formed into, for example, tapered shapes. In this case, needless to say, a proximal end of the sheath 44 is formed so as to have a diameter larger than that of the base portion 64 or 68. At this time, when the sheath 44 moves toward the distal end of the cylindrical member 42 and is engaged with the tapered portion, the holding section 26 closes. When the sheath 44 moves toward the proximal end of the cylindrical member 42 to come away from the tapered portion, the holding section 26 opens.

Figure 4:
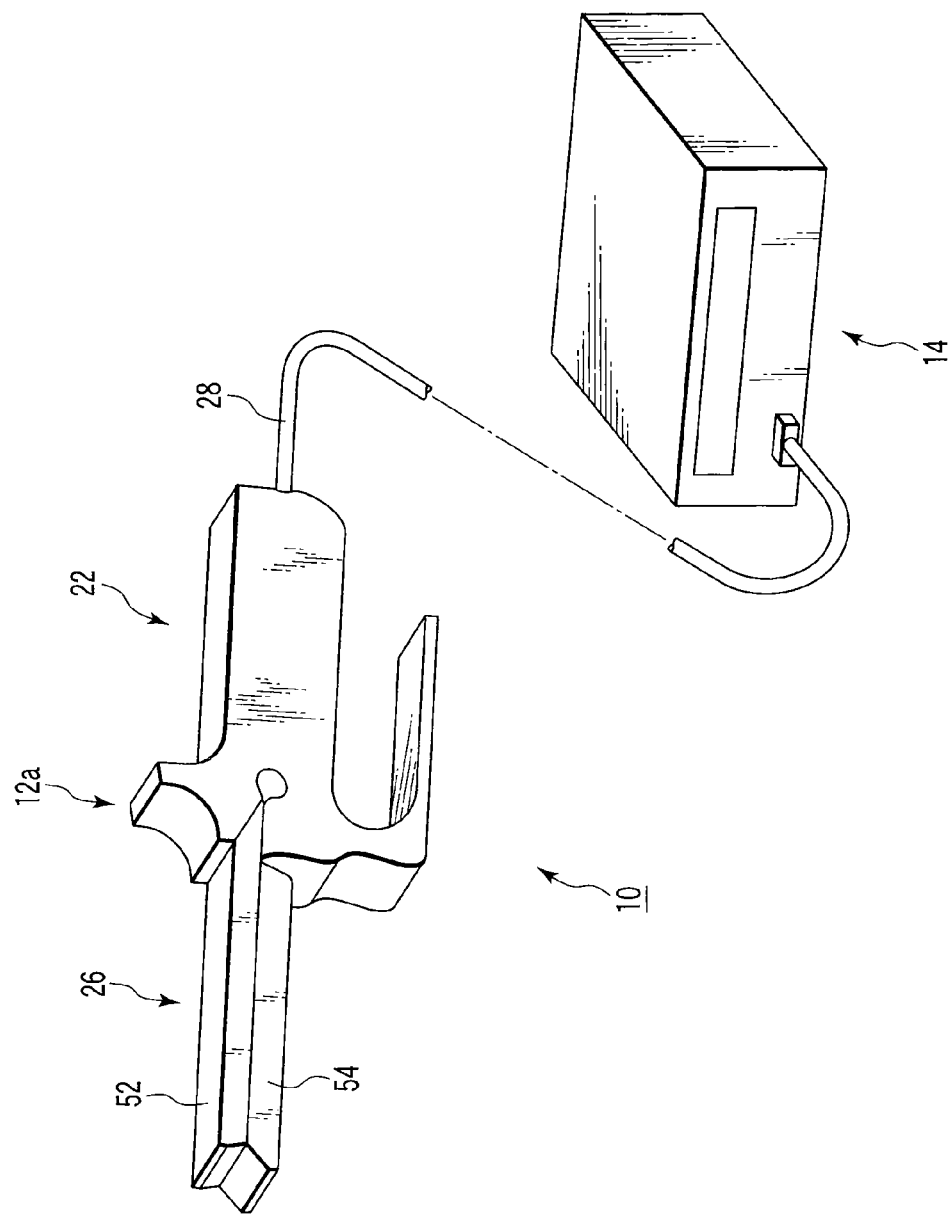
FIG. 4 is a schematic diagram showing a modification of a treatment system according to the first embodiment of the present invention.

In this embodiment, the linear electro-surgical device 12 for treating the living tissue in the abdominal cavity (in a body) through the abdominal wall has been described as an example. However, for example, as shown in FIG. 4, an open type linear electro-surgical device (a treatment device for curing) 12a may be used which extracts a treatment target tissue out of the body through the abdominal wall to treat the tissue.

The electro-surgical device 12a includes a handle 22 and a holding section 26. That is, unlike the electro-surgical device 12 for treating the tissue through the abdominal wall, the shaft 24 (see FIG. 1) is omitted. On the other hand, a member having a function similar to that of the shaft 24 is disposed in the handle 22. Therefore, the device can be used in the same manner as in the electro-surgical device 12 described above with reference to FIG. 1.

For example, when the open type linear electro-surgical device 12a is used in this manner, a fluid such as a vapor may be discharged away from a living tissue directly from main bodies 62, 66 of first and second holding portions 52, 54 through a first fluid discharge groove 84a. That is, it is preferable to dispose an opening for discharging the vapor, which communicates with the first fluid discharge groove 84a, in the main bodies 62, 66 of the first and second holding portions 52, 54. If the living tissue is thermally influenced by a fluid such as the vapor, the fluid may be discharged from the holding section 26 by use of the electro-surgical device 12a having the opening (not shown) for discharging the fluid selectively disposed so that the living tissue is not substantially affected. Therefore, even a case where a living tissue in the living tissue cavity is treated using the electro-surgical device 12 shown in FIG. 1 is allowable, depending on a positional relation between the holding section 26 and the living tissue. The also applies to a circular electro-surgical device 12c of a nineteenth embodiment described later (see FIG. 27).

It is to be noted that, as shown in examples of FIGS. 5A to 5D, structures of first and second holding portions 52, 54 may variously be modified.

FIG. 5A shows a state in which a width of an electrode arrangement portion 86 is formed to be smaller than that shown in FIG. 3C. That is, a first fluid discharge groove 84a is formed to be larger than that shown in FIG. 3C. Since the first fluid discharge groove 84a has such a shape, a fluid can easily lead on the first fluid discharge groove 84a during the treatment.

FIG. 5B shows a state in which a flexible resin material 94 having a thermal resistance is disposed at an edge portion 82a of a main body 62. Therefore, while the first holding portion 52 and the second holding portion 54 hold a living tissue, a close contact property between the edge portion 82a and an edge portion 82b of the main body 62 and a main body 66 and the living tissue can be improved.

FIG. 5C shows a state in which a concave portion 96a is formed further outside an edge portion 82a of the first holding portion 52, and a convex portion 96b is formed further outside an edge portion 82b of the second holding portion 54. The convex portion 96b disposed outside the edge portion 82b fits into the concave portion 96a disposed outside the edge portion 82b. In consequence, in a case where a living tissue is subjected to a high-frequency treatment, leakage of a fluid at a time when the tissue is held between the first holding portion 52 and the second holding portion 54 can efficiently be prevented.

FIG. 5D shows a state in which a convex portion 98a is formed at an edge portion 82a of the first holding portion 52, and a concave portion 98b is formed at an edge portion 82b of the second holding portion 54. The convex portion 98a fits into the concave portion 98b. In consequence, in a case where a living tissue is subjected to a high-frequency treatment, leakage of a fluid at a time when the tissue is held between the first holding portion 52 and the second holding portion 54 can further efficiently be prevented.

Second Embodiment

Next, a second embodiment will be described with reference to FIGS. 6A to 7D. This embodiment is a modification of the first embodiment, the same members as those described in the first embodiment are denoted with the same reference numerals, and detailed description thereof is omitted.

As shown in FIGS. 6A and 6C, outside the edge portion (the barrier portion) 82a of the first holding portion 52, a conduit arrangement portion 96 is formed which is provided with a conduit (a second channel) 98 which passes a cooling fluid such as a gas or a liquid (cooling water). The conduit 98 disposed at the conduit arrangement portion 96 is formed into, for example, a cylindrical shape. An outer peripheral surface of the conduit 98 is disposed so as to come into contact with a surface virtually extended from the contact surface of the edge portion 82a. That is, a part of the outer peripheral surface of the conduit 98 along the axial direction is substantially the same plane as that of the contact surface of the edge portion 82a.

Moreover, the conduit 98 is passed through, for example, the cylindrical member 42 of the shaft 24, or a concave portion is formed at an outer peripheral surface of the cylindrical member 42. In consequence, the conduit 98 is extended to, for example, the handle 22. The conduit 98 is extended from the handle 22, disposed along the cable 28, and connected with a pump (not shown). In consequence, a fluid such as the cooling water can be circulated through the conduit 98.

It is to be noted that the conduit 98 is formed of, for example, a metal material or the like having a high thermal conductivity. Therefore, when the fluid is passed through the conduit 98, a temperature of the fluid is transferred to the outer peripheral surface of the conduit 98. That is, the outer peripheral surface of the conduit 98 is cooled.

Next, a function of a treatment system 10 according to this embodiment will be described.

As described in the first embodiment, a living tissue of a treatment target is held between the first holding portion 52 and a second holding portion 54. At this time, a contact surface of the edge portion (the barrier portion) 82a comes into close contact with the living tissue, and the living tissue comes into contact with a first high-frequency electrode 56 and a second high-frequency electrode 58. Furthermore, the living tissue comes into close contact with a conduit 98 disposed outside the edge portion 82a and an edge portion 82b of the first holding portion 52 and the second holding portion 54.

In this state, a foot switch and a hand switch are operated. An energy source 14 supplies energy to the first high-frequency electrode 56 and the second high-frequency electrode 58, respectively. On the other hand, cooling water is supplied to the conduit 98. Moreover, the living tissue between the first high-frequency electrode 56 and the second high-frequency electrode 58 is heated. At this time, a fluid such as a vapor or a liquid is generated from a heated portion of the living tissue.

Here, as described in the first embodiment, a fluid such as the vapor or the liquid flows toward a second fluid discharge groove 84b of base portions 64, 68 of the first holding portion 52 and the second holding portion 54, which communicates with a first fluid discharge groove 84a.

The fluid leads on the cylindrical member 42 further from the second fluid discharge groove 84b of the base portions 64, 68 of the first holding portion 52 and the second holding portion 54. Moreover, the fluid is derived from the shaft 24 through a fluid discharge port 48a of the cylindrical member 42 and a fluid discharge port 48b of a sheath 44.

Moreover, when the living tissue of the treatment target is heated, thermal spread occurs from the living tissue of the treatment target to a peripheral living tissue. That is, heat in the living tissue is transferred through the living tissue. Therefore, even if the living tissue is brought into close contact with the edge portions 82a, 82b of the first and second holding portions 52, 54, the heat sometimes spreads over the edge portions 82a, 82b to the living tissue disposed outside the first and second holding portions 52, 54.

Here, the cooling water is supplied to the conduits 98 arranged outside the edge portions 82a, 82b, respectively. Therefore, the living tissue brought into close contact with an outer peripheral surface of the conduit 98 having a high thermal conductivity is cooled. In consequence, an influence of the heat which spreads from the living tissue of the treatment target between the first high-frequency electrode 56 and the second high-frequency electrode 58 to a surrounding living tissue is suppressed at a portion which comes into close contact with the conduit 98. That is, the spread of the heat directed from the living tissue of the treatment target to the surrounding tissue is suppressed, when cooling the living tissue around the living tissue of the treatment target.

Moreover, if there are gaps between the living tissue and the contact surfaces of the edge portions 82a, 82b, the fluid exits from the gaps between the living tissue and the edge portions 82a, 82b. In this case, the fluid touches the conduit 98. In consequence, the fluid is cooled. Even if, for example, the high-temperature fluid exits from a holding section 26 in this manner, the fluid touches the conduit 98 and is therefore cooled to prevent the living tissue around the living tissue grasped by the holding section 26 from being influenced.

As described above, according to this embodiment, the following effects are obtained.

As described in the first embodiment, the fluid generated from the living tissue of the treatment target can be prevented from leaking to a surrounding area of the living tissue held by the holding section 26. In consequence, it can be prevented that the peripheral tissue other than the target tissue is influenced by the fluid generated from the portion to which a high-frequency current has been conducted during the treatment of the living tissue. That is, the position influenced during the treatment of the living tissue can be limited to the living tissue to which the high-frequency current has been conducted between the first high-frequency electrode 56 and the second high-frequency electrode 58.

Moreover, as described above, the contact surfaces of the edge portions 82a, 82b are arranged as barrier portions so as to be present at positions higher than those of the surfaces of the first and second high-frequency electrodes 56, 58. In consequence, a close contact property between the living tissue and the edge portions 82a, 82b can be improved. Therefore, the fluid can more securely be introduced into the first fluid discharge groove 84a.

In a case where an electro-surgical device 12 applies the high-frequency current to the living tissue of the treatment target held by the holding section 26, the conduit 98 of the first holding portion 52 and the conduit 98 of the second holding portion 54 through which the fluid for cooling is passed, respectively, can be brought into close contact with the peripheral tissue of the living tissue of the treatment target. In consequence, the living tissue brought into close contact with the conduit 98 can be cooled. Therefore, an influence at a time when the thermal spread occurs from the living tissue of the treatment target to the peripheral living tissue can be suppressed at a portion which comes into contact with the conduit 98. In this case, it can more securely prevented that the peripheral tissue other than the target tissue is influenced by the heat spread from the living tissue of the treatment target to which the high-frequency current has been conducted during the treatment of the living tissue.

When the conduit 98 capable of passing the fluid for cooling is disposed outside the holding section 26 in this manner, a region where the thermal spread occurs can securely be restricted in the edge portions 82a, 82b of the first and second holding portions 52, 54.

Moreover, if a high-temperature fluid exits from the first and second holding portions 52, 54 through the gaps between the living tissue and the edge portions 82a, 82b, the fluid touches the conduit 98. In consequence, the fluid is cooled. Therefore, the living tissue around the living tissue held by the holding section 26 can be prevented from being influenced.

It is to be noted that, as shown in examples of FIGS. 7A to 7D, structures of first and second holding portions 52, 54 may variously be modified.

FIG. 7A shows a state in which a cross section of the conduit 98 disposed at a conduit arrangement portion 96 is formed into a substantially rectangular shape. Moreover, a side surface of the conduit 98 is disposed at substantially the same plane as that of a contact surface of an edge portion 82a of the first holding portion 52. Therefore, a contact area between a living tissue and the conduit 98 can further be broadened.

FIG. 7B shows a state in which a cylindrical conduit 98 is formed below a contact surface of an edge portion 82a.

FIG. 7C shows a state in which a first high-frequency electrode 56 comes into contact with a conduit 98, therefore the cylindrical conduit 98 has an insulating property, and the conduit 98 functions as a barrier portion. Therefore, since any space is not required for edge portions 82a, 82b, widths of the first holding portion 52 and the second holding portion 54 can be reduced. Alternatively, widths of the first high-frequency electrode 56 and a second high-frequency electrode 58 can be increased.

FIG. 7D shows a state in which a main body of the first holding portion 52 on a side away from the second holding portion 54 is covered with a heat sink (a heat radiation member) 108. The heat sink 108 is formed of, for example, a metal material having a high thermal conductivity. To increase a contact area with outside air or the like, an outer peripheral surface of the heat sink 108 is provided with a plurality of protrusions or fins denoted with reference numeral 108a. It is to be noted that edge portions 82a, 82b and a conduit 98 are omitted from a first fluid discharge groove 84a of the first holding portion 52. An end of the heat sink 108 also performs a function of a barrier portion (a contact surface of the edge portion).

Therefore, in a case where heat is transferred to a surrounding living tissue owing to thermal spread, if the living tissue touches the heat sink 108, the heat transferred through the living tissue is transferred to the heat sink 108. Since the heat sink 108 is formed so as to enlarge a contact area with the outside, heat exchange between the heat sink and the outside can be performed to efficiently emit the heat from the living tissue.

It is to be noted that in a case where the heat sink 108 is formed of a metal material, it is preferable to coat the heat sink with an insulating coating.

Third Embodiment

Next, a third embodiment will be described with reference to FIGS. 8A to 8C. This embodiment is a modification of the first embodiment, the same members as those described in the first embodiment are denoted with the same reference numerals, and detailed description thereof is omitted.

As shown in FIG. 8C, the first fluid discharge groove 84a (see FIGS. 3A to 3C) is removed from the edge portion 82a of the main body 62 of the first holding portion 52. Moreover, in the edge portion 82a of the main body 62 of the first holding portion 52, the electrode arrangement portion 86 as a seat to be provided with a first high-frequency electrode 56 is formed adjacent to the edge portion 82a. The electrode arrangement portion 86 is provided with a first fluid discharge groove 112a along an axial direction of the main body 62. As shown in FIGS. 8B and 8C, the first fluid discharge groove 112a is formed continuously to a second fluid discharge groove 112b of a base portion 64 of the first holding portion 52.

As shown in FIGS. 8B and 8C, a stepped portion is formed between the surface of the first high-frequency electrode 56 and a contact surface of the edge portion 82a. The contact surface of the edge portion 82a is disposed at a position higher than that of the surface of the first high-frequency electrode 56. This stepped portion is, for example, about 0.5 mm.

The first high-frequency electrode 56 is provided with circular holes 114 extended through a first high-frequency electrode 56 at predetermined intervals along the axial direction of the main body 62. The circular holes 114 communicate with the first fluid discharge groove 112a of the electrode arrangement portion 86. It is to be noted that here, the circular holes 114 have been described, but variously shaped holes such as an elliptic hole and a polygonal hole are allowable.

Next, a function of a treatment system 10 according to this embodiment will be described.

As described in the first embodiment, a living tissue of a treatment target is grasped between the first holding portion 52 and a second holding portion 54. At this time, the contact surface of the edge portion (a barrier portion) 82a comes into close contact with the living tissue, and the living tissue comes into contact with the first high-frequency electrode 56 and a second high-frequency electrode 58.

In this state, a foot switch and a hand switch are operated. An energy source 14 supplies energy to the first high-frequency electrode 56 and the second high-frequency electrode 58, respectively. Moreover, the living tissue held between the first high-frequency electrode 56 and the second high-frequency electrode 58 is heated.

As described above, when the living tissue of the treatment target is heated, a fluid such as a vapor or a liquid at a high temperature is generated from the heated portion of the living tissue.

Here, when the first high-frequency electrode 56 is fixed to the electrode arrangement portion 86 of the main body 62 of the first holding portion 52, the surface of the first high-frequency electrode 56 exposed on a second holding portion 54 side is present at a position slightly lower than that of the contact surface of the edge portion 82a of the first holding portion 52. Similarly, when the second high-frequency electrode 58 is fixed to the electrode arrangement portion 86 of a main body 66 of the second holding portion 54, the surface of the second high-frequency electrode 58 exposed on a first holding portion 52 side is present at a position slightly lower than that of a contact surface of an edge portion 82b of the second holding portion 54. Therefore, the edge portion 82a of the first holding portion 52 and the edge portion 82b of the second holding portion 54 perform functions of barrier portions (dams) in which the fluid generated from the living tissue is prevented from leaking to the outside.

In this case, the fluid generated from the living tissue leads on the first fluid discharge groove 112a through the circular holes 114 of the first high-frequency electrode 56 of the main body 62 of the first holding portion 52 and the circular holes 114 of the second high-frequency electrode 58 of the main body 66 of the second holding portion 54. Moreover, the fluid flows toward the second fluid discharge groove 112b of the base portion 64 and a base portion 68 of the first holding portion 52 and the second holding portion 54.

As described above, according to this embodiment, the following effects are obtained.

In a case where an electro-surgical device 12 applies a high-frequency current to the living tissue of the treatment target held by a holding section 26, the contact surface of the edge portion 82a of the first holding portion 52 and the contact surface of the edge portion 82b of the second holding portion 54 can be brought into close contact with the living tissue, respectively. Therefore, even if the fluid generated from the living tissue of the treatment target flows toward the edge portion 82a of the first holding portion 52 and the edge portion 82b of the second holding portion 54, the fluid can be introduced into the first fluid discharge groove 112a on an inner side of the circular holes 114 of the first and second high-frequency electrodes 56, 58.

In consequence, it can be prevented that the peripheral tissue other than the target tissue is influenced by the fluid generated from the portion to which the high-frequency current has been conducted during the treatment of the living tissue. That is, the position influenced during the treatment of the living tissue can be limited to the living tissue to which the high-frequency current has been conducted between the first high-frequency electrode 56 and the second high-frequency electrode 58.

It is to be noted that in this embodiment, it has been described that the fluid leads on the first fluid discharge groove 112a through the circular holes 114, but as described in the first embodiment, it is also preferable that the first fluid discharge groove 84a (see FIG. 3A) is further disposed between the electrode arrangement portion 86 and first high-frequency electrode 56 and the edge portions 82a, 82b. That is, it is also preferable that the main body 62 of the first holding portion 52 is provided with two fluid discharge grooves 84a, 112a. In this case, the fluid discharge groove 84a communicates with the other fluid discharge groove 112a at the electrode arrangement portion 86.

Fourth Embodiment

Next, a fourth embodiment will be described with reference to FIGS. 9A to 9C. This embodiment is a modification of the first to third embodiments, the same members as those described in the first to third embodiments are denoted with the same reference numerals, and detailed description thereof is omitted.

As shown in FIGS. 9A to 9C, a conduit 98 is disposed in the same manner as in the second embodiment (see FIGS. 6A to 6C). The other structure is similar to that of the third embodiment (see FIGS. 8A to 8C).

Next, a function of a treatment system 10 according to this embodiment will be described.

As described in the first embodiment, a living tissue of a treatment target is grasped between the first holding portion 52 and a second holding portion 54. At this time, the contact surface of the edge portion (a barrier portion) 82a comes into close contact with the living tissue, and the living tissue comes into contact with the first high-frequency electrode 56 and a second high-frequency electrode 58. Furthermore, the living tissue comes into close contact with a conduit 98 disposed outside the first holding portion 52 and the second holding portion 54.

In this state, a foot switch and a hand switch are operated. An energy source 14 supplies energy to the first high-frequency electrode 56 and the second high-frequency electrode 58, respectively. On the other hand, cooling water is supplied to the conduit 98. Moreover, the living tissue held between the first high-frequency electrode 56 and the second high-frequency electrode 58 is heated.

A function of discharging a fluid such as a vapor or a liquid is similar to that of the third embodiment. Therefore, description thereof is omitted.

Moreover, when the living tissue of the treatment target is heated, thermal spread occurs from the living tissue of the treatment target to a peripheral living tissue.

Here, the cooling water is supplied to the conduits 98 arranged outside the edge portions 82a, 82b, respectively. Therefore, the living tissue brought into close contact with an outer peripheral surface of the conduit 98 having a high thermal conductivity is cooled. Therefore, an influence of heat spread from the living tissue of the treatment target between the first high-frequency electrode 56 and the second high-frequency electrode 58 is suppressed at a portion brought into close contact with the conduit 98. That is, the living tissue around the living tissue of the treatment target is cooled to thereby suppress the spread of the heat directed from the living tissue of the treatment target to the surrounding tissue.

Moreover, if there are gaps between the living tissue and the edge portions 82a, 82b, a fluid such as the vapor or the liquid exits from the gaps between the living tissue and the edge portions 82a, 82b. In this case, the fluid touches the conduit 98. In consequence, the fluid is cooled.

As described above, according to this embodiment, the following effects are obtained.

In a case where an electro-surgical device 12 applies a high-frequency current to the living tissue of the treatment target held by a holding section 26, the contact surface of the edge portion 82a of the first holding portion 52 and a contact surface of the edge portion 82b of the second holding portion 54 can be brought into close contact with the living tissue, respectively. Therefore, even if the fluid generated from the living tissue of the treatment target flows toward the edge portion 82a of the first holding portion 52 and the edge portion 82b of the second holding portion 54, the fluid can be introduced into a first fluid discharge groove 112a on an inner side of circular holes 114 of the first and second high-frequency electrodes 56, 58.

In consequence, it can be prevented that the peripheral tissue other than the target tissue is influenced by the fluid generated from the portion to which the high-frequency current has been conducted during the treatment of the living tissue. That is, the position influenced during the treatment of the living tissue can be limited to the living tissue to which the high-frequency current has been conducted between the first high-frequency electrode 56 and the second high-frequency electrode 58.

Moreover, in a case where an electro-surgical device 12 applies a high-frequency current to the living tissue of the treatment target held by a holding section 26, the conduits 98 of the first holding portion 52 and the second holding portion 54 through which the fluid for cooling is passed, respectively, can be brought into close contact with the peripheral tissue of the living tissue of the treatment target. In consequence, the living tissue brought into close contact with the conduit 98 can be cooled. Therefore, an influence at a time when the thermal spread from the living tissue of the treatment target to the peripheral living tissue can be suppressed at a portion which comes into contact with the conduit 98. In this case, it can securely be prevented that the peripheral tissue other than the target tissue is influenced by the heat spread from the living tissue of the treatment target to which the high-frequency current has been conducted during the treatment of the living tissue.

Therefore, as described in the second embodiment, when the conduit 98 capable of passing the fluid for cooling is disposed outside the holding section 26, a region where the thermal spread occurs can securely be restricted to a region on inner sides of the edge portions 82a, 82b of the first and second holding portions 52, 54.

Moreover, in the same manner as in the second embodiment, even if the high-temperature fluid is to exit from the first and second holding portions 52, 54, the fluid touches the conduit 98, and can be cooled. In consequence, the living tissue around the living tissue held by the holding section 26 can be prevented from being affected.

Fifth Embodiment

Next, a fifth embodiment will be described with reference to FIGS. 10A to 10D. This embodiment is a modification of the first and third embodiments, the same members as those described in the first and third embodiments are denoted with the same reference numerals, and detailed description is omitted.

As shown in FIGS. 10B and 10C, a main body 62 of a first holding portion 52 on a side close to a second holding portion 54 is formed to be flat. As shown in FIGS. 10A to 10C, the main body 62 of the first holding portion 52 is provided with a plurality of electrode arrangement portions (concave portions) 122 formed in a discrete manner. Here, four rows of the electrode arrangement portions 122 are arranged in a zigzag form on the main body 62.

As shown in FIGS. 10A and 10D, these electrode arrangement portions 122 are provided with barrier portions 124. On an inner side of each barrier portion 124, a first high-frequency electrode 126 having a through hole 126a at the center of the electrode is disposed as an output portion or an energy emitting portion. The surfaces of the first high-frequency electrodes 126 on a side close to the second holding portion 54 are present at positions lower than those of the barrier portions 124. That is, the barrier portion 124 is present above the surface of the first high-frequency electrode 126, and there is a stepped portion between the barrier portion 124 and the first high-frequency electrode 126.

As shown in FIGS. 10B and 10C, the main body 62 is provided with a first fluid discharge groove 128a along an axial direction of the main body 62. The first fluid discharge groove 128a communicates with the through holes 126a of the first high-frequency electrodes 126, respectively. The first fluid discharge groove 128a is formed continuously to a second fluid discharge groove 128b of a base portion 64 of the first holding portion 52.

It is to be noted that since the second holding portion 54 has a structure similar to that of the first holding portion 52, barrier portions and high-frequency electrodes are denoted with reference numerals used in the first holding portion 52, and description thereof is omitted.

Next, a function of a treatment system 10 according to this embodiment will be described.

As described in the first embodiment, a living tissue of a treatment target is held between the first holding portion 52 and the second holding portion 54. At this time, the barrier portions 124 come into close contact with the living tissue. Moreover, the living tissue comes into contact with the first high-frequency electrode 126 and a second high-frequency electrode 126.

In this state, a foot switch and a hand switch are operated. An energy source 14 supplies energy to the first high-frequency electrode 126 and the second high-frequency electrode 126, respectively. Moreover, the living tissue between the first high-frequency electrode 126 and the second high-frequency electrode 126 is heated.

As described above, when the living tissue of the treatment target is heated, the living tissue between the first high-frequency electrode 126 and the second high-frequency electrode 126 is heated, and a fluid such as a vapor or a liquid is generated from the heated portion of the living tissue.

Here, when the first high-frequency electrode 126 is fixed to the barrier portion 124 of the main body 62 of the first holding portion 52, the surface of the first high-frequency electrode 126 exposed on a second holding portion 54 side is present at a position slightly lower than that of the barrier portion 124. This also applies to the second high-frequency electrode 126. Moreover, since the barrier portion 124 is brought into close contact with the living tissue, the fluid can be prevented from leaking to the outside. In this case, the fluid generated from the living tissue leads on the first fluid discharge groove 128a through the through hole 126a of the first high-frequency electrode 126 and the through hole 126a of the second high-frequency electrode 126. Moreover, the fluid flows toward the second fluid discharge grooves 128b of the base portions 64, 68 of the first and second holding portions 52, 54.

As described above, according to this embodiment, the following effects are obtained.

When an electro-surgical device 12 applies a high-frequency current to the living tissue of the treatment target grasped by the holding section 26, the barrier portions 124 of the first holding portion 52 and the barrier portions 124 of the second holding portion 54 can be brought into close contact with the living tissue, respectively. Therefore, even if the fluid generated from the living tissue of the treatment target flows toward the barrier portions 124 of the first holding portion 52 and the barrier portions 124 of the second holding portion 54, the fluid can be introduced into the first fluid discharge groove 128a on an inner side of the through hole 126a of the first high-frequency electrode 126.

In consequence, it can be prevented that the peripheral tissue other than the target tissue is influenced by the fluid generated from the portion to which a high-frequency current has been conducted during the treatment of the living tissue. That is, the position influenced during the treatment of the living tissue can be limited to the living tissue to which the high-frequency current has been conducted between the first high-frequency electrode 126 and the second high-frequency electrode 126.

Moreover, in the electro-surgical device 12 according to this embodiment, since the first holding portion 52 and the second holding portion 54 are provided with a plurality of high-frequency electrodes 126 in a discrete manner, a treatment target can be limited. That is, a treatment target region can be restricted in each barrier portion 124, and a living tissue of a surrounding portion of the barrier portion 124 keeps a normal state. Therefore, the treated living tissue can be cured earlier.

It is to be noted that in this embodiment, a state in which the barrier portions 124 and the first high-frequency electrodes 126 are arranged at random has been described, but it is preferable that these barrier portions 124 and the first high-frequency electrodes 126 are arranged so as to form a line.

Sixth Embodiment

Next, a sixth embodiment will be described with reference to FIGS. 11A to 11D. This embodiment is a modification of the first, second, fourth and fifth embodiments, the same members as those described in the first, second, fourth and fifth embodiments are denoted with the same reference numerals, and detailed description is omitted.

As shown in FIGS. 11A to 11C, a main body 62 of a first holding portion 52 is provided with a conduit arrangement portion 96 in which a conduit 98 having a high thermal conductivity is disposed. A cooling plate 146 is disposed on the conduit 98. That is, the main body 62 of the first holding portion 52 is provided with the cooling plate 146 to cover the conduit 98. In the cooling plate 146, two rows of circular electrode arrangement portions 122 are formed at a predetermined interval. The electrode arrangement portions 122 are provided with barrier portions 124. On an inner side of each barrier portion 124, a first high-frequency electrode 126 having a through hole 126a at the center of the electrode is disposed.

Next, a function of a treatment system 10 according to this embodiment will be described.

As described in the first embodiment, a living tissue of a treatment target is held between the first holding portion 52 and a second holding portion 54. At this time, the barrier portions 124 come into close contact with the living tissue. Moreover, the living tissue comes into contact with the first high-frequency electrode 126 and a second high-frequency electrode 126. Furthermore, the living tissue comes into close contact with the cooling plates 146 disposed outside the first holding portion 52 and the second holding portion 54.

In this state, a foot switch and a hand switch are operated. An energy source 14 supplies energy to the first high-frequency electrode 126 and the second high-frequency electrode 126, respectively. On the other hand, cooling water is supplied to the conduit 98. Moreover, the living tissue between the first high-frequency electrode 126 and the second high-frequency electrode 126 is heated.

A function of discharging a fluid such as a vapor or a liquid is similar to that of the fifth embodiment. Therefore, description of the function of discharging the fluid is omitted.

Moreover, when the living tissue of the treatment target is heated, thermal spread occurs from the living tissue of the treatment target to a peripheral living tissue.

At this time, according to a function similar to that described in the second embodiment, the spread of heat directed from the living tissue of the treatment target to the surrounding tissue is suppressed, when cooling the living tissue around the living tissue of the treatment target.

Here, the cooling water is supplied to the conduits 98 arranged outside the first and second holding portions 52, 54, respectively. Therefore, the living tissue is cooled via the cooling plate 146 brought into close contact with an outer peripheral surface of the conduit 98 having a high thermal conductivity. Therefore, an influence of the heat spread from the living tissue of the treatment target between the first high-frequency electrode 126 and the second high-frequency electrode 126 is suppressed at a portion brought into close contact with the cooling plate 146. That is, the spread of the heat from the living tissue of the treatment target is suppressed, when cooling the living tissue around the living tissue of the treatment target.

Moreover, if there is a gap between the living tissue and the barrier portion 124, a fluid such as the vapor or the liquid exits from the gap between the living tissue and the barrier portion 124. In this case, the fluid touches the cooling plate 146. In consequence, the fluid is cooled.

As described above, according to this embodiment, the following effects are obtained.

In a case where an electro-surgical device 12 applies a high-frequency current to the living tissue of the treatment target grasped by a holding section 26, the barrier portions 124 of the first holding portion 52 and the barrier portions 124 of the second holding portion 54 can be brought into close contact with the living tissue. Therefore, even if the fluid generated from the living tissue of the treatment target flows toward the barrier portions 124 of the first holding portion 52 and the barrier portions 124 of the second holding portion 54, the fluid can be introduced into a first fluid discharge groove 128a on inner sides of the through holes 126a of the first high-frequency electrodes 126.

In consequence, it can be prevented that the peripheral tissue other than the target tissue is influenced by the fluid generated from the portion to which the high-frequency current has been conducted during treatment of the living tissue. That is, the position influenced during the treatment of the living tissue can be limited to the living tissue to which the high-frequency current has been conducted between the first high-frequency electrode 126 and the second high-frequency electrode 126.

Moreover, in a case where the electro-surgical device 12 applies corresponding high-frequency current to the living tissue of the treatment target held by the holding section 26, the cooling plate 146 of the first holding portion 52 and the cooling plate 146 of the second holding portion 54, which are cooled, respectively, can be brought into close contact with the living tissue. In consequence, the living tissue brought into close contact with the cooling plate 146 can be cooled. Therefore, the influence at a time when the thermal spread occurs from the living tissue of the treatment target to the peripheral living tissue can be suppressed in the portion brought into contact with the cooling plate 146. In this case, it can more securely be prevented that the peripheral tissue other than the target tissue is influenced by the heat spread from the living tissue of the treatment target to which the high-frequency current has been conducted during the treatment of the living tissue.

Therefore, in a case where the cooling plate 146 whose surface can be cooled is disposed on the holding section 26, a region where the thermal spread occurs can securely be restricted in the first and second holding portions 52, 54.

Moreover, in the same manner as in the conduit 98 described in the second embodiment, if the high-temperature fluid is to exit from the first and second holding portions 52, 54, the fluid touches the cooling plate 146, and can be cooled. Therefore, the living tissue around the living tissue held by the holding section 26 can be prevented from being affected.

Seventh Embodiment

Next, a seventh embodiment will be described with reference to FIGS. 12A to 12D. This embodiment is a modification of the fifth embodiment, the same members as those described in the fifth embodiment are denoted with the same reference numerals, and detailed description thereof is omitted.

As shown in FIGS. 12B and 12C, a main body 62 of a first holding portion 52 on a side close to a second holding portion 54 is formed to be flat. As shown in FIGS. 12A and 12C, the main body 62 of the first holding portion 52 is provided with a plurality of electrode arrangement portions (concave portions) 132 formed in a discrete manner. Each electrode arrangement portion 132 is formed to be rectangular. Here, as shown in FIG. 12A, four rows of the electrode arrangement portions 132 are formed in a zigzag form on the main body 62 of the first holding portion 52.

As shown in FIGS. 12A to 12D, these electrode arrangement portions 132 are provided with rectangular barrier portions 134. On an inner side of each barrier portion 134, a first high-frequency electrode 136 having a through hole 136a is disposed as an output portion or an energy emitting portion. The through hole 136a is formed at a position adjacent to, for example, the barrier portion 134. In this case, the through hole 136a is formed at an end of the first high-frequency electrode 136. The surfaces of the first high-frequency electrodes 136 on a side close to the second holding portion 54 are present at positions lower than those of the barrier portions 134. That is, the barrier portion 134 is present above the surface of the first high-frequency electrode 136, and there is a stepped portion between the barrier portion 134 and the first high-frequency electrode 136.

As shown in FIGS. 12B and 12C, each through hole 136a communicates with a first fluid discharge groove 128a formed in the main body 62. The first fluid discharge groove 128a communicates with the through holes 136a of the first high-frequency electrodes 136, respectively. The first fluid discharge groove 128a is formed continuously to a second fluid discharge groove 128b of a base portion 64 of the first holding portion 52.

That is, in this embodiment, the circular electrode arrangement portion 122 described in the fifth embodiment (see FIGS. 10A to 10C) is replaced with the rectangular electrode arrangement portion 132. The circular barrier portion 124 is replaced with the rectangular barrier portion 134, the circular first high-frequency electrode 126 is replaced with the rectangular first high-frequency electrode 136, and the other structure is the same. Therefore, descriptions of functions and effects of this embodiment are omitted.

Eighth Embodiment

Next, an eighth embodiment will be described with reference to FIGS. 13A to 13D. This embodiment is a modification of the first, second, fourth, sixth and seventh embodiments, the same members as those described in the first, second, fourth, sixth and seventh embodiments are denoted with the same reference numerals, and detailed description thereof is omitted.

As shown in FIG. 13A, a main body 62 of a first holding portion 52 is provided with two rows of rectangular electrode arrangement portions 132 formed at predetermined intervals. Furthermore, a conduit 98 and a first high-frequency electrode 136 are arranged in the same manner as in the sixth embodiment (see FIGS. 11A to 11C).

In this embodiment, the circular electrode arrangement portion 122 described in the sixth embodiment is replaced with the rectangular electrode arrangement portion 132. The circular barrier portion 124 is replaced with the rectangular barrier portion 134, the circular first high-frequency electrode 126 is replaced with the rectangular first high-frequency electrode 136, and the other structure is the same. Therefore, descriptions of functions and effects of this embodiment are omitted.

Ninth Embodiment

Next, a ninth embodiment will be described with reference to FIGS. 14A to 14C. This embodiment is a modification of the sixth embodiment, the same members as those described in the sixth embodiment are denoted with the same reference numerals, and detailed description thereof is omitted.

As shown in FIGS. 14A and 14B, a main body 62 of a first holding portion 52 is provided with a lid portion 142 on a side away from a second holding portion 54. A plurality of pin-like first high-frequency electrodes 144 are fixed to the lid portion 142 as output portions or energy emitting portions. The main body 62 is provided with a flat cooling plate (a heat radiation member) 146 on a side close to the second holding portion 54. The cooling plate 146 is provided with a plurality of circular holes 146a arranged at zigzag vertex positions. From each circular hole 146a, a barrier portion 148 disposed integrally with the main body 62 is protruded. Each barrier portion 148 is formed into a hollow cylindrical shape. That is, each barrier portion 148 is provided with a through hole 148a formed along a central axis of the barrier portion.

when the main body 62 is provided with the lid portion 142, each first high-frequency electrode 144 having a pin shape is disposed in the through hole 148a of the barrier portion 148. Here, among the first high-frequency electrodes 144, an end of the first high-frequency electrode close to the second holding portion 54 is present at a position lower than that of the barrier portion 148 close to the second holding portion 54.

A space between the barrier portion 148 and the first high-frequency electrode 144 is a fluid discharge groove (a fluid passage) 152. The fluid discharge groove 152 communicates between the side close to the second holding portion 54 and the side away from the second holding portion 54, and is opened on the side away from the second holding portion 54.

Furthermore, a conduit arrangement portion 154 is formed on a side surface of the main body 62 on a backside of the cooling plate 146. The conduit arrangement portion 154 is provided with a conduit 156 which passes a fluid such as a gas for cooling or a liquid.

It is to be noted that since the second holding portion 54 has a structure similar to that of the first holding portion 52, barrier portions and high-frequency electrodes are denoted with reference numerals used in the first holding portion 52, and description thereof is omitted.

Next, a function of a treatment system 10 according to this embodiment will be described.

As described in the first embodiment, a living tissue of a treatment target is held between the first holding portion 52 and the second holding portion 54. At this time, the barrier portions 148 come into close contact with the living tissue. The living tissue comes into contact with the first high-frequency electrode 144 and a second high-frequency electrode 144. Furthermore, the living tissue comes into close contact with the cooling plates 146 disposed at the main body 62 and a main body 66 of the first holding portion 52 and the second holding portion 54.

In this state, a foot switch and a hand switch are operated. An energy source 14 supplies energy to the first high-frequency electrode 144 and the second high-frequency electrode 144, respectively. On the other hand, cooling water is supplied to the conduit 156.

Between the first high-frequency electrode 144 and the second high-frequency electrode 144, a high-frequency current is conducted via the living tissue. In consequence, the living tissue between the first high-frequency electrode 144 and the second high-frequency electrode 144 is heated.

When the living tissue of the treatment target is heated in this manner, a fluid such as a vapor or a liquid is generated from the heated portion of the living tissue.

Here, when each first high-frequency electrode 144 is disposed on an inner side of the barrier portion 148 of the main body 62 of the first holding portion 52, an end of the first high-frequency electrode 144 exposed on a second holding portion 54 side close to the second holding portion 54 is present at a position slightly lower than that of the barrier portion 148. The second high-frequency electrode 144 is similarly present at a position slightly lower than that of the barrier portion 148. Therefore, the barrier portions 148 of the first holding portion 52 and the barrier portions 148 of the second holding portion 54 allow the fluid generated from the living tissue to lead on the fluid discharge grooves 152 through the through holes 148a. In this case, the fluid generated from the living tissue is discharged from the fluid discharge grooves 152 of the lid portions 142 disposed on the main bodies 62, 66 of the first holding portion 52 and the second holding portion 54, respectively.

Moreover, when the living tissue of the treatment target is heated, thermal spread occurs from the living tissue of the treatment target to a peripheral living tissue.

Here, the cooling water is supplied to the conduits 156 arranged outside the first and second holding portions 52, 54, respectively. Therefore, the living tissue is cooled via the cooling plate 146 brought into close contact with an outer peripheral surface of the conduit 156 having a high thermal conductivity. Therefore, an influence of heat spread from the living tissue of the treatment target between the first high-frequency electrode 144 and the second high-frequency electrode 144 is suppressed at a portion brought into close contact with the cooling plate 146. That is, the spread of the heat from the living tissue of the treatment target is suppressed, when cooling the living tissue around the living tissue of the treatment target.

Moreover, if there are gaps between the living tissue and the barrier portions 148, the fluid exits from the gaps between the living tissue and the barrier portions 148. In this case, the fluid touches the cooling plate 146. In consequence, the fluid is cooled.

As described above, according to this embodiment, the following effects are obtained.

When the electro-surgical device 12 applies the high-frequency current to the living tissue of the treatment target grasped by the holding section 26, the barrier portions 148 of the first holding portion 52 and the barrier portions 148 of the second holding portion 54 can be brought into close contact with the living tissue, respectively. Therefore, even if the fluid generated from the living tissue of the treatment target flows toward the barrier portions 148 of the first holding portion 52 and the barrier portions 148 of the second holding portion 54, the fluid can be introduced into the first fluid discharge grooves 152 through the through holes 148a between the first high-frequency electrodes 144 and the barrier portions 148.

In consequence, it can be prevented that the peripheral tissue other than the target tissue is influenced by the fluid generated from the portion to which the high-frequency current has been conducted during the treatment of the living tissue. That is, the position influenced during the treatment of the living tissue can be limited to the living tissue to which the high-frequency current has been conducted between the first high-frequency electrode 144 and the second high-frequency electrode 144.

Moreover, in a case where an electro-surgical device 12 applies the high-frequency current to the living tissue of the treatment target held by a holding section 26, the cooling plates 146 of the first holding portion 52 and the second holding portion 54 which are cooled, respectively, can be brought into close contact with the living tissue. In consequence, the living tissue brought into close contact with the cooling plates 146 can be cooled. Therefore, an influence at a time when the thermal spread directed from the living tissue of the treatment target to the peripheral living tissue can be suppressed at a portion which comes into contact with the cooling plate 146. In this case, it can be prevented that the peripheral tissue other than the target tissue is influenced by the heat spread from the living tissue of the treatment target to which the high-frequency current has been conducted during treatment of the living tissue.

Therefore, in a case where the cooling plate 146 having the surface which can be cooled is disposed at the holding section 26, a region where the thermal spread occurs can securely be restricted in the first and second holding portions 52, 54.

Moreover, in the same manner as in the conduit 98 described in the second embodiment, even if the high-temperature fluid is to exit from the first and second holding portions 52, 54, the fluid touches the cooling plate 146 and can therefore be cooled. In consequence, the living tissue around the living tissue held by the holding section 26 can be prevented from being affected.

Furthermore, in the electro-surgical device 12 according to this embodiment, the first holding portion 52 and the second holding portion 54 are provided with the plurality of high-frequency electrodes 144 in the discrete manner. Therefore, the treatment target can be limited.

Therefore, it can be prevented that the peripheral tissue other than the target tissue is influenced by the fluid generated from the portion to which the high-frequency current has been conducted during the treatment of the living tissue. That is, since a treatment region can be limited to the inside of each barrier portion 148 and the living tissue of a portion around the barrier portion 148 keeps a normal state, this can contribute to earlier cure.

It is to be noted that as shown in FIG. 14C, the barrier portion 148 may be formed as a part of the cooling plate 146 instead of a part of the main body 62.

Tenth Embodiment

Next, a tenth embodiment will be described with reference to FIGS. 15A and 15B. This embodiment is a modification of the ninth embodiment, the same members as those described in the ninth embodiment are denoted with the same reference numerals, and detailed description thereof is omitted.

Figures 15A, 15B:
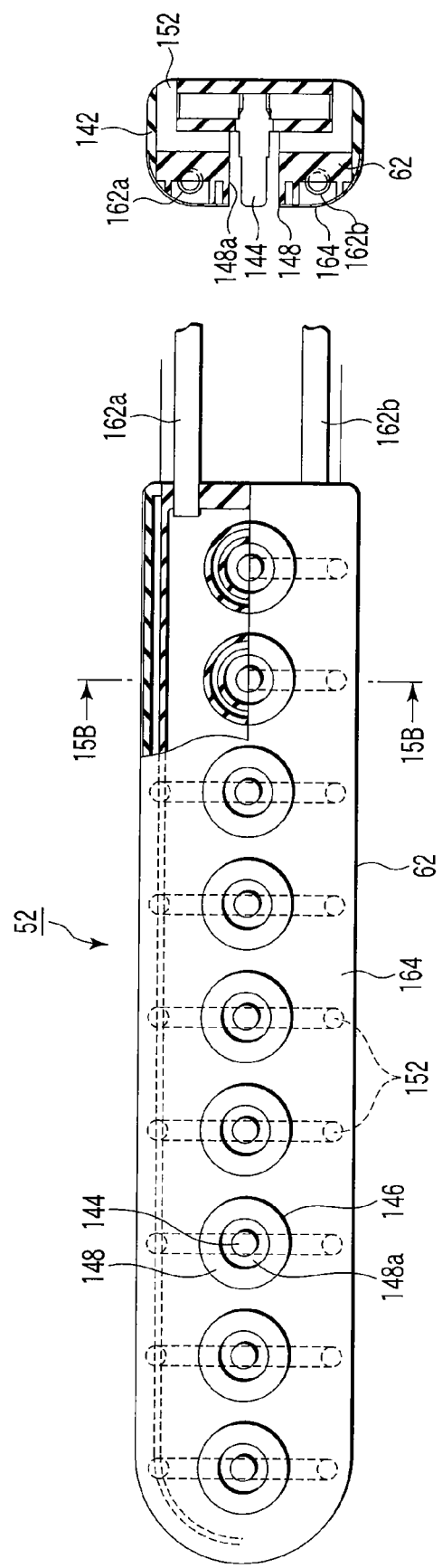
FIG. 15A is a schematic plan view showing a first holding portion on a side close to a second holding portion in a holding section of an electro-surgical device according to a tenth embodiment.
FIG. 15B is a schematic longitudinal sectional view cut along the 15B-15B line of FIG. 15A, showing the first holding portion of the holding section of the electro-surgical device according to the tenth embodiment.

As shown in FIG. 15A, a main body 62 of a first holding portion 52 is fixed to one end of a conduit 162a for inflow, which allows a fluid such as a gas or a liquid to lead on the main body. The main body 62 of the first holding portion 52 is fixed to one end of a conduit 162b for outflow, from which a fluid such as the gas or the liquid is discharged. The main body 62 is provided with a flexible sheet-like member (a heat radiation member) 164 on a side close to a second holding portion 54. The sheet-like member 164 is formed of, for example, a silicone material or the like. A space between the inside of the sheet-like member 164 and the main body 62 is filled with a fluid (e.g., cooling water) for cooling, and is disposed in a watertight manner.

First high-frequency electrodes 144 are arranged at predetermined intervals along a longitudinal direction of the main body 62. An end of the first high-frequency electrode 144 close to the second holding portion 54 is present at a position lower than that of each barrier portion 148 close to the second holding portion 54.

It is to be noted that since the second holding portion 54 has a structure similar to that of the first holding portion 52, barrier portions and high-frequency electrodes are denoted with reference numerals used in the first holding portion 52, and description thereof is omitted.

Next, a function of a treatment system 10 according to this embodiment will be described.

As described in the first embodiment, a living tissue of a treatment target is held between the first holding portion 52 and the second holding portion 54. At this time, the barrier portions 148 come into close contact with the living tissue, the living tissue comes into contact with the first high-frequency electrode 144 and a second high-frequency electrode 144. Furthermore, the living tissue comes into close contact with the sheet-like members 164 arranged on the main body 62 and a main body 66 of the first holding portion 52 and the second holding portion 54. Since the sheet-like member 164 is formed of a flexible material, the member is deformed in accordance with a shape of the living tissue to come into close contact with the living tissue.

In this state, a foot switch and a hand switch are operated. An energy source 14 supplies energy to the first high-frequency electrode 144 and the second high-frequency electrode 144, respectively. On the other hand, cooling water is supplied through the conduit 162a. In consequence, a space between the main body 62 and the sheet-like member 164 is filled with the cooling water.

Between the first high-frequency electrode 144 and the second high-frequency electrode 144, a high-frequency current is conducted via the living tissue. Therefore, the living tissue between the first high-frequency electrode 144 and the second high-frequency electrode 144 is heated.

When the living tissue of the treatment target is heated, a fluid such as the vapor or the liquid is generated from the heated portion of the living tissue.

Here, when the first high-frequency electrodes 144 are arranged in the barrier portions 148 of the main body 62 of the first holding portion 52, an end of the first high-frequency electrode 144 exposed on a second holding portion 54 side is present at a position slightly lower than that of the barrier portion 148. There is a similar relation between the second high-frequency electrode 144 and the barrier portion 148. Therefore, the fluid is discharged from the fluid discharge grooves 152 through the through holes 148a.

Moreover, when the living tissue of the treatment target is heated, thermal spread occurs from the living tissue of the treatment target to a peripheral living tissue.

Here, the cooling water is supplied from the conduit 162a disposed outside the first and second holding portions 52, 54, respectively, and drained from the conduit 162b. Therefore, a gap between the main body 62 and the sheet-like member 164 is filled with the cooling water from the conduit 162a. Therefore, the living tissue brought into close contact with an outer peripheral surface of the sheet-like member 164 is cooled. In this case, an influence of the heat which spreads from the living tissue of the treatment target between the first high-frequency electrode 144 and the second high-frequency electrode 144 is suppressed at a portion which comes into close contact with the sheet-like member 164. That is, the spread of the heat directed from the living tissue of the treatment target is suppressed, when cooling the living tissue around the living tissue of the treatment target.

Moreover, if there are gaps between the living tissue and the barrier portions 148, the fluid exits from the gaps between the living tissue and the barrier portions 148. In this case, the fluid touches the sheet-like member 164. In consequence, the fluid is cooled.

As described above, according to this embodiment, the following effects are obtained.

When an electro-surgical device 12 applies the high-frequency current to the living tissue of the treatment target grasped by a holding section 26, the barrier portions 148 of the first holding portion 52 and the barrier portions 148 of the second holding portion 54 can be brought into close contact with the living tissue, respectively. Therefore, the fluid generated from the living tissue of the treatment target can be introduced into the first fluid discharge grooves 152 through the through holes 148a between the first high-frequency electrodes 144 and the barrier portions 148.

In consequence, it can be prevented that the peripheral tissue other than the target tissue is influenced by the fluid generated from the portion to which the high-frequency current has been conducted during the treatment of the living tissue. That is, the position influenced during the treatment of the living tissue can be limited to the living tissue to which the high-frequency current has been conducted between the first high-frequency electrode 144 and the second high-frequency electrode 144.

Moreover, in a case where an electro-surgical device 12 applies a high-frequency current to the living tissue of the treatment target held by a holding section 26, the sheet-like member 164 of the first holding portion 52 and the sheet-like member 164 of the second holding portion 54 which are cooled, respectively, can be brought into close contact with the living tissue. In consequence, the living tissue brought into close contact with the sheet-like members 164 can be cooled. Therefore, an influence at a time when the thermal spread directed from the living tissue of the treatment target to the peripheral living tissue can be suppressed at a portion which comes into contact with the sheet-like member 164. In this case, it can more securely be prevented that the peripheral tissue other than the target tissue is influenced by the heat spread from the living tissue of the treatment target to which the high-frequency current has been conducted during the treatment of the living tissue.

Therefore, when the sheet-like member 164 whose surface can be cooled is disposed on the holding section 26, a region where the thermal spread occurs can securely be restricted in the first and second holding portions 52, 54. Furthermore, since the sheet-like member 164 is formed of a flexible material, a close contact property with respect to the living tissue can be improved. Therefore, the living tissue can more efficiently be cooled.

Moreover, in the same manner as in the first embodiment, even if the high-temperature fluid is to exit from the first and second holding portions 52, 54, the fluid touches the sheet-like member 164, and can be cooled. In consequence, the living tissue around the living tissue held by the holding section 26 can be prevented from being affected.

Eleventh Embodiment

Next, an eleventh embodiment will be described with reference to FIGS. 16A to 16C. This embodiment is a modification of the first embodiment, the same members as those described in the first embodiment are denoted with the same reference numerals, and detailed description thereof is omitted.

As shown in FIGS. 16A to 16C, a main body 62 of a first holding portion 52 is provided with first high-frequency electrodes 166 having convex portions 166a. On the other hand, as shown in FIGS. 16B and 16C, a main body 66 of a second holding portion 54 is provided with second high-frequency electrodes 168 having concave portions 168a. The surface of the second high-frequency electrode 168 is provided with an elastic member 170 having an insulating property. The elastic member 170 is disposed on an inner peripheral surface of the concave portion 168a as well as the surface of the second high-frequency electrode 168.

Fluid passing holes (fluid passages) 166b, 168b are formed at the convex portions 166a of the first high-frequency electrodes 166 and the concave portions 168a of the second high-frequency electrodes 168, respectively. These fluid passing holes 166b, 168b communicate with a first fluid discharge groove 128a.

It is to be noted that as shown in FIG. 16C, in a state in which the first holding portion 52 and the second holding portion 54 are closed, a gap S is formed between a flat portion of the first high-frequency electrode 166 and the insulating elastic member 170. A gap S is formed between the convex portion 166a of the first high-frequency electrode 166 and the concave portion 168a of the second high-frequency electrode 168.

Next, a function of a treatment system 10 according to this embodiment will be described.

As described in the first embodiment, a living tissue of a treatment target is held between the first holding portion 52 and the second holding portion 54. At this time, the convex portions 166a of the first high-frequency electrodes 166 arranged on the main body 62 of the first holding portion 52 come into close contact with the living tissue. Moreover, the convex portions come into contact with bottom portions of the concave portions 168a of the second high-frequency electrodes 168 arranged on the main body 66 of the second holding portion 54. That is, the living tissue is disposed in the gap S between the convex portion 166a of the first high-frequency electrode 166 and the concave portion 168a of the second high-frequency electrode 168. Here, the elastic member 170 disposed on the surface of the second high-frequency electrode 168 brings the living tissue between the first holding portion 52 and the second holding portion 54 into close contact with the members.

In this state, a foot switch and a hand switch are operated. An energy source 14 supplies energy to the first high-frequency electrode 166 and the second high-frequency electrode 168, respectively.

Between the first high-frequency electrode 166 and the second high-frequency electrode 168, a high-frequency current is conducted via the living tissue of the treatment target. In consequence, the living tissue between the first high-frequency electrode 166 and the second high-frequency electrode 168 is heated.

When the living tissue of the treatment target is heated in this manner, a fluid such as a vapor or a liquid is generated from the heated portion of the living tissue. Here, the living tissue disposed between the first high-frequency electrode 166 and the second high-frequency electrode 168 comes into close contact with the elastic member 170. Therefore, these elastic members 170 of the second holding portions 54 perform functions of barrier portions (dams) in which the fluid generated from the living tissue is prevented from leaking to the outside.

In this case, the fluid generated from the living tissue leads on the fluid passing hole 168b of the concave portion 168a of the second high-frequency electrode 168 in the second holding portion 54. Moreover, the fluid flows toward a second fluid discharge groove 128b of a base portion 68 of the second holding portion 54 via the first fluid discharge groove 128a.

As described above, according to this embodiment, the following effects are obtained.

When an electro-surgical device 12 applies the high-frequency current to the living tissue of the treatment target grasped by a holding section 26, the convex portions 166a of the first high-frequency electrodes 166 of the first holding portion 52 and the bottom portions of the concave portions 168a of the second high-frequency electrodes 168 of the second holding portion 54 can be brought into close contact with the living tissue, respectively. Therefore, the fluid generated from the living tissue of the treatment target can be introduced into the base portion 68 of the second holding portion 54 through the fluid passing hole 168b.

In consequence, it can be prevented that the peripheral tissue other than the target tissue is influenced by the fluid generated from the portion to which the high-frequency current has been conducted during the treatment of the living tissue. That is, the position influenced during the treatment of the living tissue can be limited to the living tissue to which the high-frequency current has been conducted between the first high-frequency electrode 166 and the second high-frequency electrode 168.

It is to be noted that in this embodiment, it has been described that the fluid passing holes 166b, 168b are arranged in the first high-frequency electrode 166 and the second high-frequency electrode 168, but it is also preferable that the holes are arranged, for example, in the only first high-frequency electrodes 166 having the convex portions 166a or the only second high-frequency electrodes 168 having the concave portions 168a.

Twelfth Embodiment

Next, a twelfth embodiment will be described with reference to FIGS. 17A to 17C. This embodiment is a modification of the second and eleventh embodiments, the same members as those described in the second and eleventh embodiments are denoted with the same reference numerals, and detailed description thereof is omitted.

As shown in FIGS. 17A to 17C, a main body 62 and a base portion 64 of the first holding portion 52 are provided with a conduit arrangement portion 96. The conduit arrangement portion 96 is provided with a conduit 98 having a high thermal conductivity. The conduit 98 is brought into contact with a cooling plate 146. The cooling plate 146 is disposed on the surfaces of the main body 62 and the base portion 64 of the first holding portion 52 on a side close to the second holding portion 54. Furthermore, the cooling plate 146 is provided with a circular hole 166c in which a convex portion 166a of a first high-frequency electrode 166 is disposed.

The main body 66 and the base portion 68 of the second holding portion 54 are also provided with a conduit arrangement portion 96. The conduit arrangement portion 96 is provided with a conduit 98. The conduit 98 is brought into contact with a cooling plate 146. The cooling plate 146 is disposed on the surfaces of the main body 66 and the base portion 68 of the second holding portion 54 on a side close to the first holding portion 52. Furthermore, the cooling plate 146 is provided with a circular hole 168c to expose an electrode of a bottom portion of a concave portion 168a of a second high-frequency electrode 168. It is to be noted that the cooling plate 146 is disposed on an inner peripheral surface of the concave portion 168a as well as the surface of the second high-frequency electrode 168.

Next, a function of a treatment system 10 according to this embodiment will be described.

As described in the first embodiment, a living tissue of a treatment target is held between the first holding portion 52 and the second holding portion 54. At this time, the convex portion 166a of the first high-frequency electrode 166 disposed at the main body 62 of the first holding portion 52 comes into close contact with the living tissue, and also comes into contact with the bottom portion of the concave portion 168a of the second high-frequency electrode 168 disposed on the main body 66 of the second holding portion 54. That is, the living tissue is disposed in the gap S between the convex portion 166a of the first high-frequency electrode 166 and the concave portion 168a of the second high-frequency electrode 168. Here, the living tissue between the first holding portion 52 and the second holding portion 54 comes into close contact with the holding portions via the cooling plates 146 disposed on the surfaces of the first and second high-frequency electrodes 166, 168, respectively.

In this state, a foot switch and a hand switch are operated. An energy source 14 supplies energy to the first high-frequency electrode 166 and the second high-frequency electrode 168, respectively.

Between the first high-frequency electrode 166 and the second high-frequency electrode 168, a high-frequency current is conducted via the living tissue. In consequence, the living tissue between the first high-frequency electrode 166 and the second high-frequency electrode 168 is heated.

When the living tissue of the treatment target is heated in this manner, a fluid such as a vapor or a liquid is generated from the heated portion of the living tissue. Here, the living tissue disposed between the first high-frequency electrode 166 and the second high-frequency electrode 168 comes into close contact with the cooling plates 146, respectively. Therefore, the cooling plates 146 of the first holding portion 52 and the second holding portion 54 perform functions of barrier portions (dams) in which the fluid generated from the living tissue is prevented from leaking to the outside.

In this case, the fluid generated from the living tissue leads on a fluid channel 166b of the convex portion 166a of the first high-frequency electrode 166 of the first holding portion 52, and leads on a fluid channel 168b of the concave portion 168a of the second high-frequency electrode 168 of the second holding portion 54. Moreover, these fluids flow toward second fluid discharge grooves 128b of the base portion 64 of the first holding portion 52 and the base portion 68 of the second holding portion 54 via first fluid discharge grooves 128a.

Moreover, when the living tissue of the treatment target is heated, thermal spread occurs from the living tissue of the treatment target to a peripheral living tissue.

Here, cooling water is supplied to the conduits 98 arranged outside the first and second holding portions 52, 54, respectively. Therefore, the living tissue is cooled via the cooling plates 146 brought into close contact with an outer peripheral surface of the conduit 98 having a high thermal conductivity. Therefore, an influence of heat spread from the living tissue of the treatment target between the first high-frequency electrode 166 and the second high-frequency electrode 168 is suppressed at portions brought into close contact with the cooling plates 146. That is, the living tissue around the living tissue of the treatment target is cooled to thereby suppress the spread of the heat from the living tissue of the treatment target.

Moreover, if there are gaps between the living tissue and the cooling plates 146, a fluid such as the vapor or the liquid exits from the gaps between the living tissue and the cooling plates 146. In this case, the fluid touches the cooling plates 146. In consequence, the fluid is cooled.

As described above, according to this embodiment, the following effects are obtained.

In a case where an electro-surgical device 12 applies a high-frequency current to the living tissue of the treatment target grasped by a holding section 26, the cooling plate 146 of the first holding portion 52 and the cooling plate 146 of the second holding portion 54 which are cooled, respectively, can be brought into close contact with the living tissue. Therefore, even if the fluid generated from the living tissue of the treatment target flows toward the cooling plates 146 of the first holding portion 52 and the second holding portion 54, the cooling plate 146 disposed at the concave portion 166b of the main body 66 of the second holding portion 54 functions as a barrier portion. In consequence, the fluid can be introduced into the first fluid discharge groove 128a through the through hole 166a of the first high-frequency electrode 166 and/or into the first fluid discharge groove 128a through the through hole 168a of the second high-frequency electrode 168.

Therefore, it can be prevented that the peripheral tissue other than the target tissue is influenced by the fluid generated from the portion to which the high-frequency current has been conducted during the treatment of the living tissue. That is, the position influenced during the treatment of the living tissue can be limited to the living tissue to which the high-frequency current has been conducted between the first high-frequency electrode 166 and the second high-frequency electrode 168.

Moreover, when the electro-surgical device 12 applies the high-frequency current to the living tissue of the treatment target held by the holding section 26, the cooling plate 146 of the first holding portion 52 and the cooling plate 146 of the second holding portion 54 which are cooled, respectively, can be brought into close contact with the living tissue. In consequence, the living tissue brought into close contact with the cooling plates 146 can be cooled. Therefore, an influence at a time when the thermal spread occurs from the living tissue of the treatment target to the peripheral living tissue can be suppressed at portions which come into contact with the cooling plates 146. In this case, it can more securely be prevented that the peripheral tissue other than the target tissue is influenced by the heat spread from the living tissue of the treatment target to which the high-frequency current has been conducted during the treatment of the living tissue.

Therefore, in a case where the cooling plates 146 whose surfaces can be cooled are disposed on the holding section 26, a region where the thermal spread occurs can securely be restricted in the first and second holding portions 52, 54.

Moreover, in the same manner as in the conduit 98 described in the second embodiment, even if the high-temperature fluid is to exit from the first and second holding portions 52, 54, the fluid touches the cooling plate 146, and can be cooled. In consequence, the living tissue around the living tissue held by the holding section 26 can be prevented from being affected.

Thirteenth Embodiment

Next, a thirteenth embodiment will be described with reference to FIGS. 18 to 20C. This embodiment is a modification of the first to twelfth embodiments, the same members as those described in the first to twelfth embodiments are denoted with the same reference numerals, and detailed description is omitted.

As shown in FIG. 18, a handle 22 of an electro-surgical device (a treatment device for curing) 12b according to this embodiment is provided with a cutter driving knob 34 disposed along a holding section opening/closing knob 32.

As shown in FIGS. 19A and 19B, a driving rod 172 is movably disposed along an axial direction of a cylindrical member 42 in the cylindrical member of a shaft 24. A distal end of the driving rod 172 is provided with a thin-plate-like cutter 174. Therefore, when a cutter driving knob 34 is operated, the cutter (an auxiliary treatment device) 174 moves via the driving rod 172.

As shown in FIGS. 19A and 19B, a distal end of the cutter 174 is provided with a blade 174a, and the distal end of the driving rod 172 is fixed to a proximal end of the cutter 174. A longitudinal groove 174b is formed between the distal end and the proximal end of the cutter 174. Engagement portions 174c which engage with a movement regulation pin 176 are formed on one end of the longitudinal groove 174b, the other end and between one end and the other end. In the longitudinal groove 174b, the movement regulation pin 176 extending in a direction crossing the axial direction of the shaft 24 at right angles is fixed to the cylindrical member 42 of the shaft 24. Therefore, the longitudinal groove 174b of the cutter 174 moves along the movement regulation pin 176. In this case, the cutter 174 linearly moves. At this time, the cutter 174 is disposed along cutter guide grooves (fluid discharge grooves) 182a, 182b, 184a and 184b of a first holding portion 52 and a second holding portion 54.

As shown in FIGS. 20A to 20C, the first fluid discharge groove 84a (see FIGS. 3A to 3C) described in the first embodiment is removed from an edge portion 82a of a main body 62 of the first holding portion 52, and an electrode arrangement portion 86 as a seat on which a first high-frequency electrode 56 is disposed is formed adjacent to the edge portion.

The first cutter guide groove 182a which passes the cutter 174 is formed in the first high-frequency electrode 56 and the electrode arrangement portion 86 of the main body 62 of the first holding portion 52. A base portion 64 of the first holding portion 52 is provided with the second cutter guide groove 182b formed continuously to the first cutter guide groove 182a. This second cutter guide groove 182b is formed along the axial direction of the shaft 24.

Therefore, the cutter 174 is movable along the cutter guide grooves 182a, 182b in the first holding portion 52. Similarly, the cutter 174 is movable along the cutter guide grooves 184a, 184b in the second holding portion 54.

Since another structure is similar to that of the first holding portion 52 described in the first embodiment, description thereof is omitted.

Next, a function of a treatment system 10 according to this embodiment will be described.

As described in the first embodiment, a living tissue of a treatment target is held between the first holding portion 52 and the second holding portion 54. At this time, a contact surface of the edge portion 82a comes into close contact with the living tissue. Moreover, the living tissue comes into contact with the first high-frequency electrode 56 and a second high-frequency electrode 58.

In this state, a foot switch and a hand switch are operated. An energy source 14 supplies energy to the first high-frequency electrode 56 and the second high-frequency electrode 58, respectively.

Between the first high-frequency electrode 56 and the second high-frequency electrode 58, a high-frequency current is conducted via the living tissue of the treatment target. Therefore, the living tissue between the first high-frequency electrode 56 and the second high-frequency electrode 58 is heated.

When the living tissue of the treatment target is heated in this manner, a fluid such as a vapor or a liquid is generated from the heated portion of the living tissue.

Here, instead of the first fluid discharge groove 84a described in the first embodiment, the fluid generated from the living tissue of the treatment target leads on the fluid discharge grooves which are the first cutter guide grooves 182a, 184a of the main body 62 and a main body 66 of the first holding portion 52 and the second holding portion 54, respectively. Moreover, the fluid flows toward the second cutter guide grooves 182b, 184b of the base portion 64 and a base portion 68 of the first holding portion 52 and the second holding portion 54.

The fluid further leads on the cylindrical member 42 from the second cutter guide grooves 182b, 184b of the base portions 64, 68 of the first holding portion 52 and the second holding portion 54. Moreover, the fluid is derived from the shaft 24 through a fluid discharge port 48a of the cylindrical member 42 and a fluid discharge port 48b of a sheath 44.

Moreover, when the cutter driving knob 34 of the handle 22 is operated, the cutter 174 moves toward distal ends of the first holding portion 52 and the second holding portion 54. Since the distal end of the cutter 174 is provided with the blade 174a, the treated living tissue is cut.

As described above, according to this embodiment, the following effects are obtained in addition to the effect described in the first embodiment.

The fluid generated at a time when an electro-surgical device 12 applies a high-frequency current to the living tissue grasped by a holding section 26 can be introduced into the first cutter guide grooves (fluid passages) 182a, 184a. That is, the cutter guide grooves 182a, 182b, 184a and 184b may be used as the fluid discharge grooves.

Moreover, the cutter 174 and the cutter guide groove 182 may appropriately be used in the first holding portion 52 and the second holding portion 54 described in the above second to sixth embodiments.

Fourteenth Embodiment

Next, a fourteenth embodiment will be described with reference to FIGS. 21A to 22D. This embodiment is a modification of the second and thirteenth embodiments, the same members as those described in the second and thirteenth embodiments are denoted with the same reference numerals, and detailed description is omitted.

As shown in FIG. 21A, unlike the thirteenth embodiment, a conduit 98 is disposed in the same manner as in the second embodiment (see FIGS. 6A to 6C). Another structure is similar to that of the thirteenth embodiment. Therefore, descriptions of functions and effects of this embodiment are omitted.

It is to be noted that as shown in examples of FIGS. 22A to 22D, structures of first and second holding portions 52, 54 may variously be modified. They correspond to FIGS. 7A to 7D of the second embodiment except that a first fluid discharge groove 84a is removed and a cutter guide groove 182a is disposed.

FIG. 22A shows a state in which a cross section of a conduit 98 disposed at a conduit arrangement portion 96 is formed into a substantially rectangular shape. Moreover, a side surface of the conduit 98 is disposed at substantially the same plane as that of a contact surface of an edge portion 82a of the first holding portion 52. Therefore, a contact area between a living tissue and the conduit 98 can further be broadened.

FIG. 22B shows a state in which a cylindrical conduit 98 is formed below a contact surface of an edge portion 82a.

FIG. 22C shows a state in which a first high-frequency electrode 56 comes into contact with a conduit 98, therefore the cylindrical conduit 98 has an insulating property, and the conduit 98 functions as a barrier portion. Therefore, since any space for edge portions 82a, 82b does not have to be disposed, widths of the first holding portion 52 and the second holding portion 54 can be reduced. Alternatively, widths of the first high-frequency electrode 56 and a second high-frequency electrode 58 can be increased.

FIG. 22D shows a state in which a main body of the first holding portion 52 on a side away from the second holding portion 54 is covered with a heat sink 108. The heat sink 108 is formed of, for example, a metal material having a high thermal conductivity. To increase a contact area with outside air or the like, an outer peripheral surface of the heat sink 108 is provided with a plurality of protrusions or fins denoted with reference numeral 108a. It is to be noted that edge portions 82a, 82b and a conduit 98 are omitted from a first fluid discharge groove 84a of the first holding portion 52. An end of the heat sink 108 also performs a function of a barrier portion (a contact surface of the edge portion).

Fifteenth Embodiment

Next, a fifteenth embodiment will be described with reference to FIGS. 23A to 23D. This embodiment is a modification of the fifth, ninth and thirteenth embodiments, the same members as those described in the fifth, ninth and thirteenth embodiments are denoted with the same reference numerals, and detailed description is omitted.

As shown in FIGS. 23A to 23C, a barrier portion 148 of the ninth embodiment and a first high-frequency electrode 126 of the fifth embodiment are applied to the thirteenth embodiment. Therefore, descriptions of functions and effects of this embodiment are omitted.

Sixteenth Embodiment

Next, a sixteenth embodiment will be described with reference to FIGS. 24A and 24B. This embodiment is a modification of the fifth and thirteenth embodiments, the same members as those described in the fifth and thirteenth embodiments are denoted with the same reference numerals, and detailed description is omitted.

As shown in FIG. 24A, an electrode arrangement hole 132, a barrier portion 134 and a first high-frequency electrode 136 of the fifth embodiment is applied to the thirteenth embodiment. Therefore, descriptions of functions and effects of this embodiment are omitted.

It is to be noted that in the thirteenth to sixteenth embodiments, it has been described that an electro-surgical device 12b having a cutter 174 shown in FIG. 18 is used, but a cutter 174 may similarly be disposed in an electro-surgical device 12a shown in FIG. 4 to similarly perform a treatment.

Seventeenth Embodiment

Next, a seventeenth embodiment will be described with reference to FIGS. 25A to 25C. This embodiment is a modification of the first embodiment, but here a case where a living tissue is treated using laser energy instead of high-frequency energy will be described. Therefore, although not shown, an energy source 14 (see FIG. 1) emits laser light into a fiber 198 of an energy treatment device (a laser treatment device) 12 described later.

As shown in FIGS. 25A to 25C, an electrode arrangement portion 86 is omitted from a main body 62 of a first holding portion 52. Moreover, a first high-frequency electrode 56 is also omitted. Instead of the electrode arrangement portion 86, a heat transfer plate arrangement portion 192 is disposed. The heat transfer plate arrangement portion 192 is formed as a seat on which a transfer plate 194 is disposed as an output portion or an energy emitting portion. The heat transfer plate arrangement portion 192 is recessed from an edge portion 82a of the main body 62.

The transfer plate 194 is formed into a substantially plate shape formed as a flat surface on a side which faces a second holding portion 54, and fixed to the heat transfer plate arrangement portion 192.

A concave groove 194a is formed in the transfer plate 194. The concave groove 194a of the transfer plate 194 is provided with a diffuser 196 as an output portion or an energy emitting portion. The fiber 198 is passed through the diffuser 196. Therefore, when the laser light incidents the fiber 198, the laser light diffuses outwards from the diffuser 196. When the transfer plate is irradiated with energy due to the laser light, the energy is converted into thermal energy and transferred.

Next, a function of a treatment system 10 according to this embodiment will be described.

As described in the first embodiment, a living tissue of a treatment target is held between the first holding portion 52 and the second holding portion 54. At this time, the living tissue of the treatment target comes into close contact with the transfer plate 194 and the diffuser 196. A peripheral tissue of the living tissue of the treatment target comes into contact with the edge portions 82a of the first holding portion 52 and an edge portion 82b of the second holding portion 54.

In this state, a foot switch and a hand switch are operated. The energy source 14 emits the laser light into the fibers 198, respectively.

Therefore, the laser light is diffused from the diffuser 196, and the energy due to the laser light is converted into thermal energy to transfer heat to the transfer plate 194. Moreover, the living tissue between the transfer plates 194 of the first holding portion 52 and the second holding portion 54 is heated.

As described above, when the living tissue of the treatment target is heated, a fluid such as a vapor or a liquid is generated from the heated portion of the living tissue.

In this case, the fluid generated from the living tissue leads on first fluid discharge grooves 84a of the main body 62 and a main body 66 of the first holding portion 52 and the second holding portion 54. Moreover, the fluid flows toward second fluid discharge grooves 84b of base portions 64, 68 of the first holding portion 52 and the second holding portion 54.

As described above, according to this embodiment, the following effects are obtained.

In a case where the energy treatment device (the laser treatment device) 12 using the laser light applies heat to the living tissue of the treatment target grasped by a holding section 26, the edge portion 82a of the first holding portion 52 and the edge portion 82b of the second holding portion 54 can be brought into close contact with the living tissues, respectively. Therefore, even if the fluid generated from the living tissue of the treatment target flows toward the edge portion 82a of the first holding portion 52 and the edge portion 82b of the second holding portion 54, the edge portions 82a, 82b come into close contact with the living tissue, and the fluid can be introduced into the first fluid discharge groove 84a. That is, the fluid generated at a time when the laser treatment device to generate heat from the heat transfer plate 194 applies the thermal energy to the living tissue held by the holding section 26 can be applied to inner side surfaces of the edge portions 82a, 82b of the first holding portion 52 and the second holding portion 54, and introduced into the first fluid discharge groove 84a.

In consequence, it can be prevented that the peripheral tissue other than the target tissue is influenced by the fluid generated from the portion to which the heat has been applied during the treatment of the living tissue. That is, the position influenced during the treatment of the living tissue can be limited to the living tissue held between the first holding portion 52 and the second holding portion 54.

It is to be noted that in this embodiment, the treatment of the living tissue by use of the laser light energy has been described, but the tissue may be treated using ultrasonic energy. In this case, an ultrasonic probe (not shown) may be used instead of the fiber 198 shown in FIGS. 25A to 25C, and a vibration plate (not shown) may be used instead of the transfer plate 194 to similarly perform an ultrasonic treatment. Furthermore, a high-frequency current may be input into the ultrasonic probe. Therefore, in this case, the ultrasonic treatment and a high-frequency treatment can be switched.

Eighteenth Embodiment

Next, an eighteenth embodiment will be described with reference to FIGS. 26A to 26C. This embodiment is a modification of the seventeenth embodiment, the same members as those described in the seventeenth embodiment are denoted with the same reference numerals, and detailed description is omitted.

As shown in FIGS. 26A to 26C, according to this embodiment, in addition to a structure described in the seventeenth embodiment, first and second holding portions 52, 54 are provided with conduit arrangement portions 96 in which conduits 98 are arranged. Moreover, the conduit arrangement portion 96 is provided with the conduit 98. The conduit 98 is also used as a barrier portion. That is, edge portions 82a, 82b are removed.

Next, a function of a treatment system 10 according to this embodiment will be described.

As described in the first embodiment, a living tissue of a treatment target is held between the first holding portion 52 and the second holding portion 54. At this time, the living tissue of the treatment target comes into close contact with a transfer plate 194 and a diffuser 196. Furthermore, the living tissue comes into close contact with the conduits 98 disposed outside the first holding portion 52 and the second holding portion 54.

In this state, a foot switch and a hand switch are operated. The energy source 14 emits laser light into fibers 198, respectively. On the other hand, cooling water is supplied to the conduit 98.

Therefore, the laser light is diffused from the diffuser 196, and the energy due to the laser light is converted into thermal energy to transfer heat to the transfer plate 194. Moreover, the living tissue between the transfer plates 194 of the first holding portion 52 and the second holding portion 54 is heated.

As described above, when the living tissue of the treatment target is heated, a fluid such as a vapor or a liquid is generated from the heated portion of the living tissue.

In this case, the fluid generated from the living tissue leads on first fluid discharge grooves 84a of main bodies 62, 66 of the first holding portion 52 and the second holding portion 54. Moreover, the fluid flows toward second fluid discharge grooves 84b of base portions 64, 68 of the first holding portion 52 and the second holding portion 54.

Moreover, when a living tissue of a treatment target is heated, thermal spread occurs from the living tissue of the treatment target to a peripheral living tissue.

Here, the cooling water is supplied to the conduits 98 arranged outside the first and second holding portions 52, 54, respectively. Therefore, the living tissue brought into close contact with an outer peripheral surface of the conduit 98 having a high thermal conductivity is cooled. Therefore, an influence of heat spread from the living tissue of the treatment target between the transfer plate 194 of the first holding portion 52 and the transfer plate 194 of the second holding portion 54 is suppressed at portions brought into close contact with the conduits 98. That is, the living tissue around the living tissue of the treatment target is cooled to thereby suppress the spread of the heat directed from the living tissue of the treatment target to the surrounding tissue.

Moreover, if there are gaps between the living tissue and the conduits (barrier portions) 98, the fluid exits from the gaps between the living tissue and the conduits 98. In this case, the fluid touches the conduits 98. In consequence, the fluid is cooled.

As described above, according to this embodiment, the following effects are obtained.

When an energy treatment device (a laser treatment device) 12 using laser light applies heat to the living tissue of the treatment target grasped by a holding section 26, the conduit 98 of the first holding portion 52 and the conduit 98 of the second holding portion 54 can be brought into close contact with the living tissue, respectively. Therefore, even if the fluid generated from the living tissue of the treatment target flows toward the conduit 98 of the first holding portion 52 and the conduit 98 of the second holding portion 54, the fluid can be introduced into the first fluid discharge groove 84a, because the conduits 98 are brought into close contact with the living tissue. That is, the fluid generated at a time when the energy treatment device to generate the heat from the transfer plates 194 applies thermal energy to the living tissue held by the holding section 26 can be applied to inner side surfaces of the conduits 98 of the first holding portion 52 and the second holding portion 54, and introduced into the first fluid discharge grooves 84a.

In consequence, it can be prevented that the peripheral tissue other than the target tissue is influenced by the fluid generated from the portion to which the heat has been applied during the treatment of the living tissue. That is, the position influenced during the treatment of the living tissue can be limited to the living tissue held between the first holding portion 52 and the second holding portion 54.

Moreover, in a case where the laser treatment device 12 applies the heat to the living tissue of the treatment target held by the holding section 26, the conduit 98 of the first holding portion 52 and the conduit 98 of the second holding portion 54 through which the fluid for cooling is passed, respectively, can be brought into close contact with the living tissue. In consequence, when the thermal spread occurs from the living tissue of the treatment target to a peripheral tissue, the living tissue brought into close contact with the conduits 98 can be cooled. Therefore, an influence of the heat spread from the living tissue of the treatment target to the peripheral living tissue can be suppressed at portions which come into contact with the conduits 98. In this case, it can securely be prevented that the peripheral tissue other than the target tissue is influenced by the heat spread from the living tissue of the treatment target to which the heat has been applied during the treatment of the living tissue.

Therefore, when the conduit 98 capable of passing the fluid for cooling is disposed outside the holding section 26, a region where the thermal spread occurs can securely be restricted in the first and second holding portions 52, 54 arranged inwardly from the conduits 98.

Moreover, in the same manner as in the first embodiment, even if the high-temperature fluid is to exit from the first and second holding portions 52, 54, the fluid touches the conduit 98, and can be cooled. In consequence, the living tissue around the living tissue held by the holding section 26 can be prevented from being affected.

In addition, in the first to eighteenth embodiments, it has been described that the same member is used in the first holding portion 52 and the second holding portion 54, but different members may be used. For example, structures described in the different embodiments may appropriately be combined.

Moreover, a shape of the treatment device, a shape of the holding section, and shapes and arrangement of a high-frequency electrode, a heater element, the diffuser and the like are not limited to those of the embodiments, and may variously be modified.

Nineteenth Embodiment

Next, a nineteenth embodiment will be described with reference to FIGS. 27 to 30. Here, as an example of an energy treatment device, a circular type bipolar electro-surgical device (a treatment device for curing) 12c will be described which performs a treatment, for example, through an abdominal wall or outside the abdominal wall.

Figure 27:
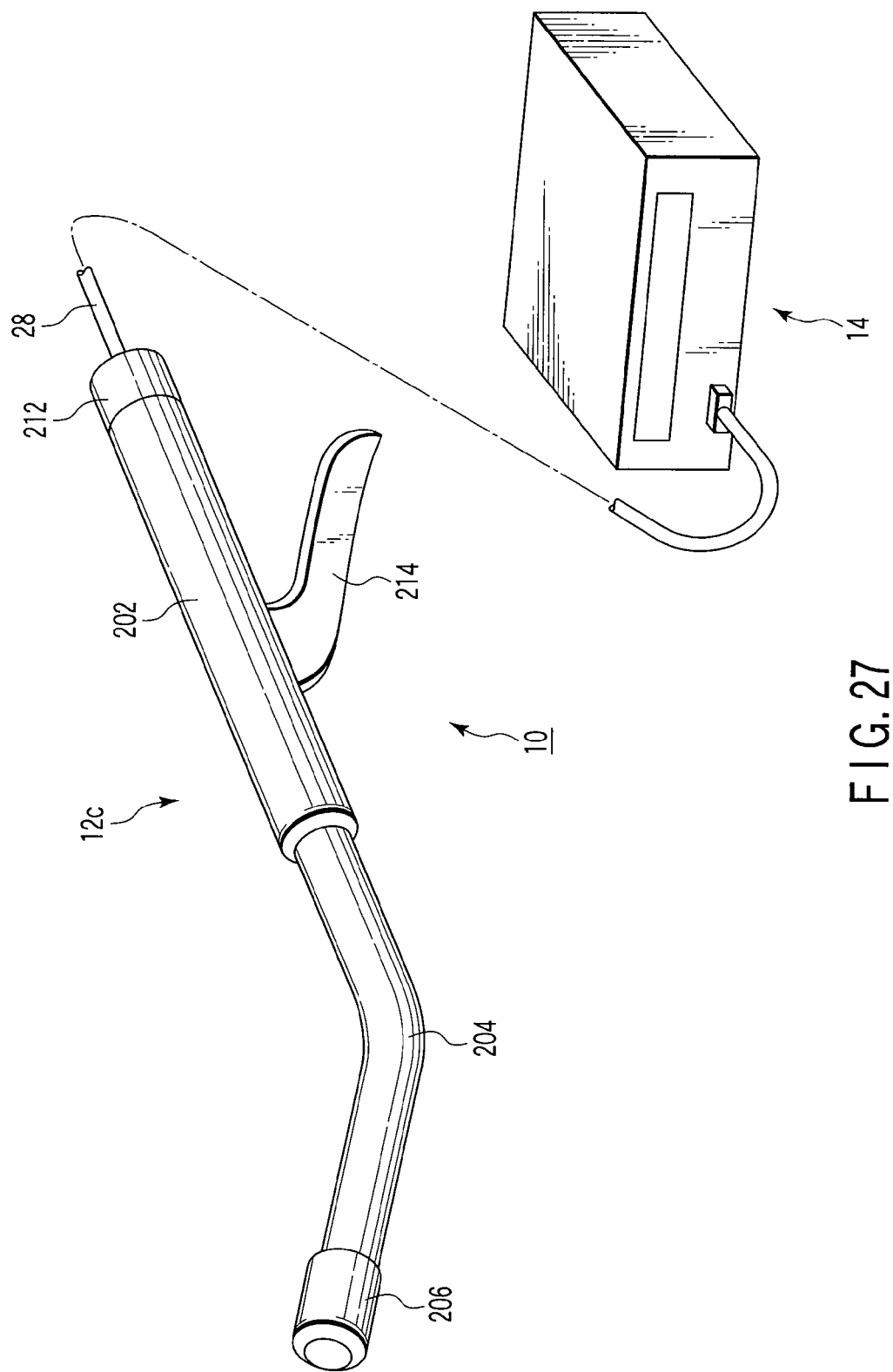
FIG. 27 is a schematic diagram showing a treatment system according to a nineteenth embodiment of the present invention.

As shown in FIG. 27, the electro-surgical device 12c includes a handle 202, a shaft 204 and an openable/closable holding section 206. The handle 202 is connected with an energy source 14 via a cable 28.

The handle 202 is provided with a holding section opening/closing knob 212 and a cutter driving lever 214. The holding section opening/closing knob 212 is rotatable with respect to the handle 202. When the holding section opening/closing knob 212 is rotated, for example, clockwise with respect to the handle 202, a detachable side holding portion 224 of the holding section 206 described later comes away from a main body side holding portion 222 (see FIG. 28A). When the knob is rotated counterclockwise, the detachable side holding portion 224 comes close to the main body side holding portion 222 (see FIG. 28B).

The shaft 204 is formed into a cylindrical shape. This shaft 204 is appropriately curved in consideration of an insertion property into a living tissue. Needless to say, the shaft 204 may linearly be formed.

Figure 28A:
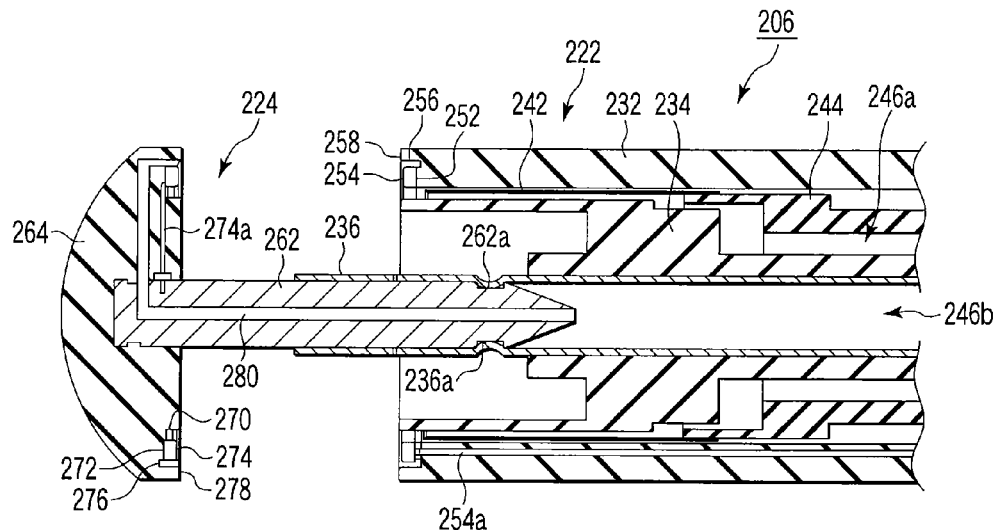
FIG. 28A is a schematic longitudinal sectional view showing a state in which a main body side holding portion engages with a detachable side holding portion and the detachable side holding portion is disposed away from the main body side holding portion of an electro-surgical device according to the nineteenth embodiment.
Figure 28B:
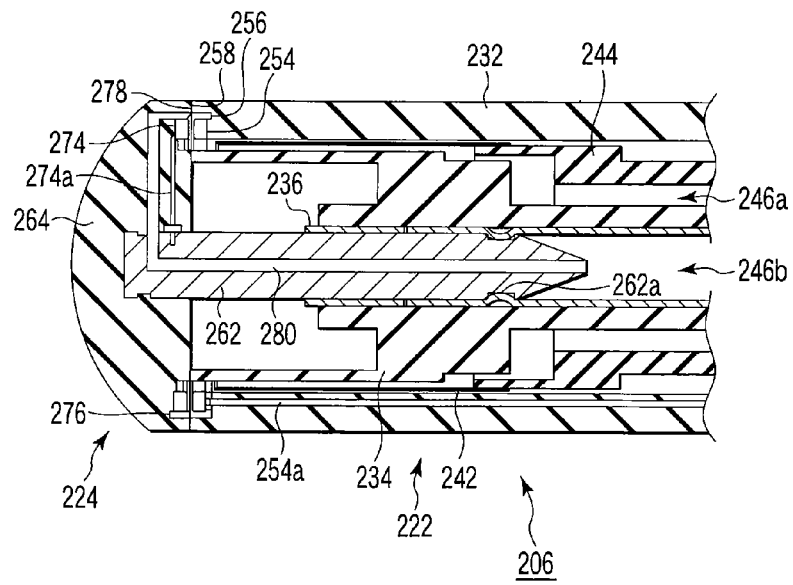
FIG. 28B is a schematic longitudinal sectional view showing a state in which the main body side holding portion engages with the detachable side holding portion and the detachable side holding portion is disposed close to the main body side holding portion of the electro-surgical device according to the nineteenth embodiment.
Figure 29:
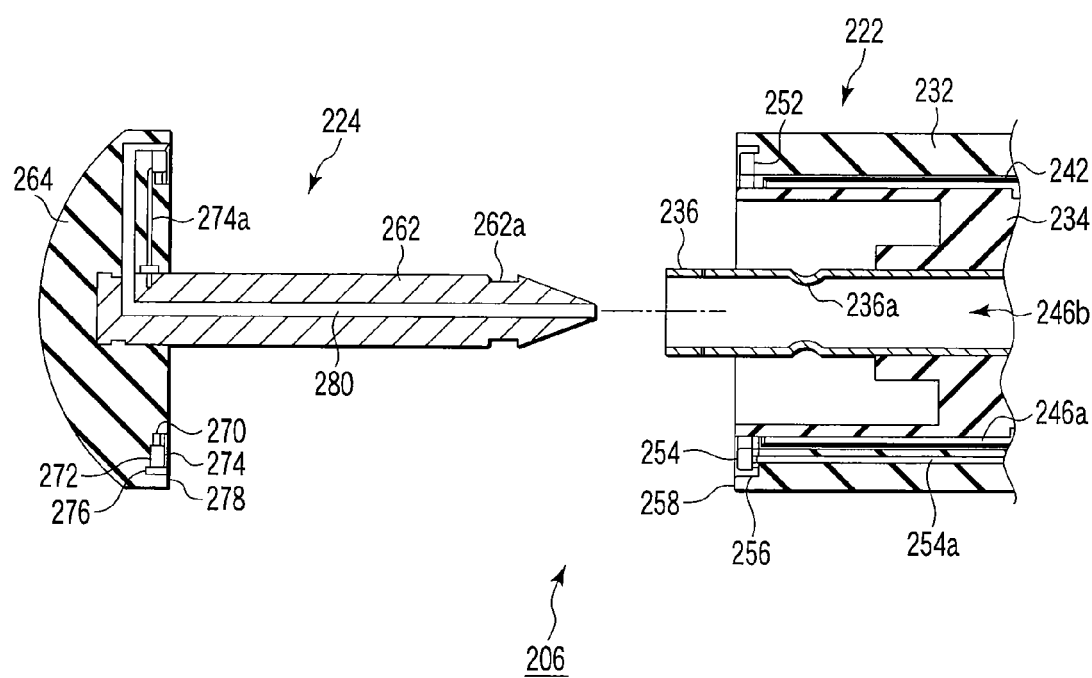
FIG. 29 is a schematic longitudinal sectional view showing the state in which the main body side holding portion and the detachable side holding portion are separated from each other of the electro-surgical device according to the nineteenth embodiment.

A distal end of the shaft 204 is provided with the holding section 206. As shown in FIGS. 28A to 29, the holding section 206 includes the main body side holding portion (a first holding portion) 222 formed at the distal end of the shaft 204, and the detachable side holding portion (a second holding portion) 224 detachably attached to the main body side holding portion 222.

The main body side holding portion 222 includes a cylindrical member 232, a frame 234 and an electric conductive pipe 236. The cylindrical member 232 and the frame 234 have an insulating property. The cylindrical member 232 is connected with the distal end of the shaft 204. The frame 234 is fixed to the cylindrical member 232.

A central axis of the frame 234 is opened. The opened central axis of the frame 234 is provided with the electric conductive pipe 236 which is movable in a predetermined region along the central axis of the frame 234. When the holding section opening/closing knob 212 is rotated, as shown in FIGS. 28A and 28B, the electric conductive pipe 236 is movable in a predetermined region owing to, for example, a function of a ball screw (not shown). The electric conductive pipe 236 is provided with a protrusion 236a which protrudes inwards in a diametric direction so that a connecting portion 262a of an electric conductive shaft 262 described later disengageably engages with the protrusion.

As shown in FIGS. 28A and 28B, a space is formed between the cylindrical member 232 and the frame 234. A cylindrical cutter 242 is disposed in the space between the cylindrical member 232 and the frame 234. A proximal end of the cutter 242 is connected with a distal end of a pusher 244 for the cutter disposed in the shaft 204. The cutter 242 is fixed to an outer peripheral surface of the pusher 244 for the cutter. Although not shown, a proximal end of the pusher 244 for the cutter is connected with the cutter driving lever 214 of the handle 202. Therefore, when the cutter driving lever 214 of the handle 202 is operated, the cutter 242 moves via the pusher 244 for the cutter.

A first fluid flow path (a fluid passage) 246a is formed between the pusher 244 for the cutter and the frame 234. Moreover, the shaft 204 or the handle 202 is provided with a fluid discharge port (not shown) from which the fluid passed through the first fluid flow path 246a is discharged to the outside.

As shown in FIGS. 28A to 30, a distal end of the cylindrical member 232 is provided with an annular electrode arrangement portion 252. A first high-frequency electrode 254 is disposed as an output portion or an energy emitting portion at the electrode arrangement portion 252. A distal end of a first conducting line 254a is fixed to the first high-frequency electrode 254. The first conducting line 254a is connected to the cable 28 via the main body side holding portion 222, the shaft 204 and the handle 202.

An annular vapor discharge groove 256 is formed outside the first high-frequency electrode 254. The fluid discharge groove 256 is connected with the first fluid flow path 246a. Outside the fluid discharge groove 256, an edge portion 258 is formed at a position higher than that of the surface of the first high-frequency electrode 254. That is, the edge portion 258 of the main body side holding portion 222 is disposed closer to a head portion 264 of the detachable side holding portion 224 described later than to the surface of the first high-frequency electrode 254.

On the other hand, the detachable side holding portion 224 includes the electric conductive shaft 262 having the connecting portion 262a, and the head portion 264. The electric conductive shaft 262 has a circular section, one end of the shaft is formed to be tapered, and the other end of the shaft is fixed to the head portion 264. The connecting portion 262a is formed into a concave groove shape so as to be engageable with the protrusion 236a of the electric conductive pipe 236. An outer surface of a portion other than the connecting portion 262a of the electric conductive shaft 262 is insulated with a coating or the like.

An annular cutter receiving portion 270 is disposed at the head portion 264. An annular electrode arrangement portion 272 is formed outside the cutter receiving portion 270. The electrode arrangement portion 272 is provided with a second high-frequency electrode 274 as an output portion or an energy emitting portion. One end of a second conducting line 274a is fixed to the second high-frequency electrode 274. The other end of the second conducting line 274a is electrically connected to the electric conductive shaft 262. An annular fluid discharge groove 276 is formed outside the second high-frequency electrode 274. Outside the fluid discharge groove 276, a contact surface of an edge portion 278 is formed at a position higher than that of the second high-frequency electrode 274. That is, the contact surface of the edge portion 278 of the detachable side holding portion 224 is disposed closer to the main body side holding portion 222 than to the surface of the second high-frequency electrode 274.

Furthermore, the fluid discharge groove 276 is connected with the head portion 264 and a fluid discharge path 280 of the electric conductive shaft 262. The fluid discharge path 280 communicates with a second fluid flow path (a fluid passage) 246b of the electric conductive pipe 236. The shaft 204 or the handle 202 is provided with a fluid discharge port (not shown) from which the fluid passed through the second fluid flow path 246b is discharged.

It is to be noted that the electric conductive pipe 236 is connected with the cable 28 via the shaft 204 and the handle 202. Therefore, when the connecting portion 262a of the electric conductive shaft 262 of the detachable side holding portion 224 is engaged with the protrusion 236a of the electric conductive pipe 236, the second high-frequency electrode 274 is electrically connected with the electric conductive pipe 236.

Next, a function of a treatment system 10 according to this embodiment will be described.

As shown in FIG. 29, in a state in which the main body side holding portion 222 is closed with respect to the detachable side holding portion 224, the holding section 206 and the shaft 204 of the electro-surgical device 12c are inserted into an abdominal cavity through, for example, an abdominal wall. The main body side holding portion 222 and the detachable side holding portion 224 of the electro-surgical device 12c is opposed to the living tissue to be treated.

The holding section opening/closing knob 212 of the handle 202 is operated in order to hold the living tissue to be treated between the main body side holding portion 222 and the detachable side holding portion 224. At this time, the knob is rotated, for example, clockwise with respect to the handle 202. In this case, as shown in FIG. 28A, the electric conductive pipe 236 is moved toward a distal end with respect to the frame 234 of the shaft 204. Therefore, the main body side holding portion 222 and the detachable side holding portion 224 are opened, and the detachable side holding portion 224 can be detached from the main body side holding portion 222.

Moreover, the living tissue to be treated is disposed between the first high-frequency electrode 254 of the main body side holding portion 222 and the second high-frequency electrode 274 of the detachable side holding portion 224. The electric conductive shaft 262 of the detachable side holding portion 224 is inserted into the electric conductive pipe 236 of the main body side holding portion 222. In this state, the holding section opening/closing knob 212 of the handle 202 is rotated, for example, counterclockwise. Therefore, the detachable side holding portion 224 closes with respect to the main body side holding portion 222. In this manner, the living tissue of the treatment target is held between the main body side holding portion 222 and the detachable side holding portion 224.

In this state, a foot switch and a hand switch are operated. The energy source 14 supplies energy to the first high-frequency electrode 254 and the second high-frequency electrode 274 via the cable 28, respectively. Between the first high-frequency electrode 254 and the second high-frequency electrode 274, a high-frequency current is conducted via the living tissue of the treatment target. In consequence, the living tissue between the first high-frequency electrode 254 and the second high-frequency electrode 274 is heated.

At this time, a fluid such as a vapor or a liquid is generated from the heated portion of the living tissue. Here, while the first high-frequency electrode 254 is fixed to the main body side holding portion 222, the surface of the first high-frequency electrode 254 exposed on a detachable side holding portion 224 side is present at a position slightly lower than that of the edge portion 258 of the main body side holding portion 222. Similarly, while the second high-frequency electrode 274 is fixed to the detachable side holding portion 224, the surface of the second high-frequency electrode 274 exposed on a main body side holding portion 222 side is present at a position slightly lower than that of the edge portion 278 of the second holding portion 54. Therefore, the edge portion 82a of the main body side holding portion 222 and the detachable side holding portion 224 perform a function of a barrier portion (a dam) in which the fluid generated from the living tissue owing to the electric conduction between the first high-frequency electrode 254 and the second high-frequency electrode 274 is introduced into the fluid discharge grooves 256, 276 and the leakage of the fluid to the outside is prevented.

In this case, in a state in which the main body side holding portion 222 and the detachable side holding portion 224 are closed, when the edge portion 258 of the main body side holding portion 222 abuts on the edge portion 278 of the detachable side holding portion 224, the fluid generated from the living tissue leads on the fluid discharge grooves 256, 276, respectively.

Moreover, the fluid which has led on the fluid discharge groove 256 is passed toward a handle 202 side through the first fluid flow path 246a provided with the cutter 174 and the pusher 244 for the cutter, and discharged from the electro-surgical device 12c.

On the other hand, the fluid which has led on the fluid discharge groove 276 is passed toward the handle 202 side through the fluid discharge path 280 and the second fluid flow path 246b, and discharged from the electro-surgical device 12c.

As described above, according to this embodiment, the following effects are obtained.

When the electro-surgical device 12c applies the high-frequency current to the living tissue of the treatment target grasped by the holding section 206, the edge portion 258 of the main body side holding portion 222 and the edge portion 278 of the detachable side holding portion 224 can be brought into close contact with the living tissue, respectively. Therefore, even if the fluid generated from the living tissue of the treatment target flows toward the edge portion 258 of the main body side holding portion 222 and the edge portion 278 of the detachable side holding portion 224, the edge portions 258, 278 are brought into close contact with the living tissue. Therefore, the fluid can be allowed to hit inner side surfaces of the edge portions 258, 278, and introduced into the fluid discharge grooves 256, 276, respectively.

In this case, the fluid generated from the living tissue of the treatment target can be discharged from the electro-surgical device 12c through the first fluid flow path 246a formed between the first high-frequency electrode 254 and the edge portion 258 of the main body side holding portion 222 and between the frame 234 and the pusher 244 for the cutter, the shaft 204, the handle 202 and the fluid discharge port.

Furthermore, the fluid generated from the living tissue of the treatment target can be discharged from the electro-surgical device 12c through the fluid discharge groove 276 formed between the second high-frequency electrode 274 and the edge portion 278 of the detachable side holding portion 224, the fluid discharge path 280, the second fluid flow path 246b, the shaft 204, the handle 202 and the fluid discharge port.

Therefore, the fluid can be prevented from leaking to a surrounding area of the living tissue held by the holding section 206.

In consequence, it can be prevented that the peripheral tissue other than the target tissue is influenced by the fluid generated from the portion to which the high-frequency current has been conducted during the treatment of the living tissue. That is, the position influenced during the treatment of the living tissue can be limited to the living tissue to which the high-frequency current has been conducted between the first high-frequency electrode 254 and the second high-frequency electrode 274.

Twentieth Embodiment

Next, a twentieth embodiment will be described with reference to FIG. 31. This embodiment is a modification of the nineteenth embodiment, the same members as those described in the nineteenth embodiment are denoted with the same reference numerals, and detailed description thereof is omitted.

Figure 31:
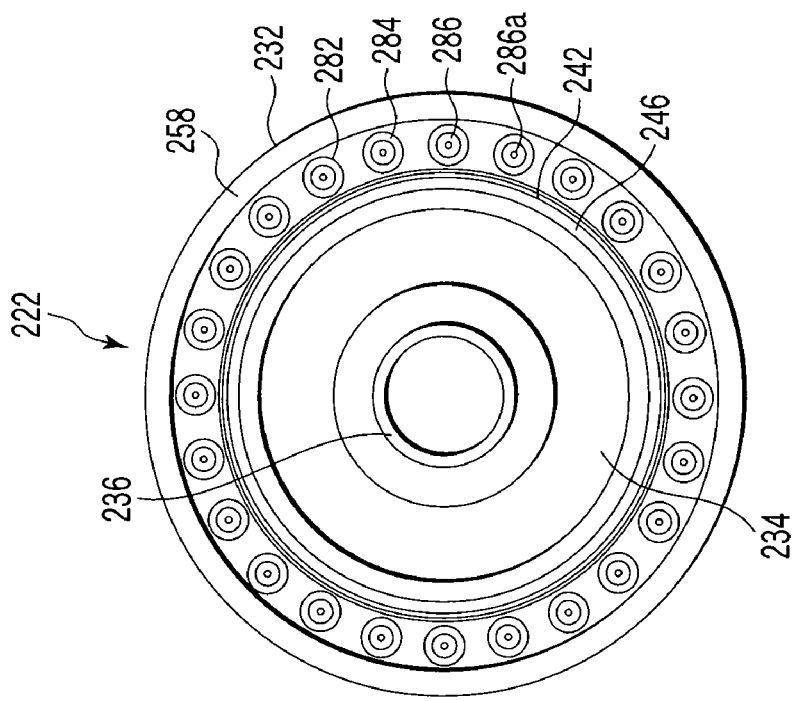
FIG. 31 is a schematic plan view showing a main body side holding portion of an electro-surgical device according to a twentieth embodiment.

In a main body side holding portion 222 of an electro-surgical device 12c shown in FIG. 31, electrode arrangement portions (concave portions) 282 are formed at predetermined intervals along a circumference. Barrier portions 284 are disposed in these electrode arrangement portions 282. The barrier portions 284 are slightly protruded toward a detachable side holding portion 224 with respect to the main body side holding portion 222. First high-frequency electrodes 286 having central through holes 286a are arranged in the barrier portions 284. The first high-frequency electrodes 286 on a side close to the detachable side holding portion 224 are present at positions lower than those of the barrier portions 284. That is, there are stepped portions between the barrier portions 284 and the first high-frequency electrodes 286.

Furthermore, although not shown, these through holes 286a are connected with a first vapor flow path 246a. Therefore, the fluid is discharged from the electro-surgical device 12c through the through holes 286a and the first fluid flow path 246a.

On the other hand, although electrode arrangement portions, barrier portions and second high-frequency electrodes having through holes of the detachable side holding portion 224 are not shown, they are similarly formed. Furthermore, the through holes of the second high-frequency electrodes are connected with a fluid discharge path 280 of a electric conductive shaft 262 and a second fluid flow path 246b of a electric conductive pipe 236. In consequence, the fluid on a detachable side holding portion 224 side is discharged from the electro-surgical device 12c through the through holes of the second high-frequency electrodes, the fluid discharge path 280 and the second fluid flow path 246b.

As described above, according to this embodiment, the following effects are obtained.

The fluid generated from a living tissue of a treatment target can be discharged from the electro-surgical device 12c through the through holes 286a of the first high-frequency electrodes 286, the first fluid flow path 246a formed between a frame 234 and a pusher 244 for the cutter, a shaft 204, a handle 202 and a fluid discharge port.

Furthermore, the fluid generated from the living tissue of the treatment target can be discharged from the electro-surgical device 12c through the through holes of the second high-frequency electrodes, the fluid discharge path 280, the second fluid flow path 246b, the shaft 204, the handle 202 and the fluid discharge port.

Therefore, the fluid can be prevented from leaking to a surrounding area of the living tissue held by a holding section 206.

In consequence, it can be prevented that the peripheral tissue other than the target tissue is influenced by the fluid generated from the portion to which a high-frequency current has been conducted during treatment of the living tissue. That is, the position influenced during the treatment of the living tissue can be limited to the living tissue to which the high-frequency current has been conducted between the first high-frequency electrode 254 and the second high-frequency electrode 274.

Figure 30:
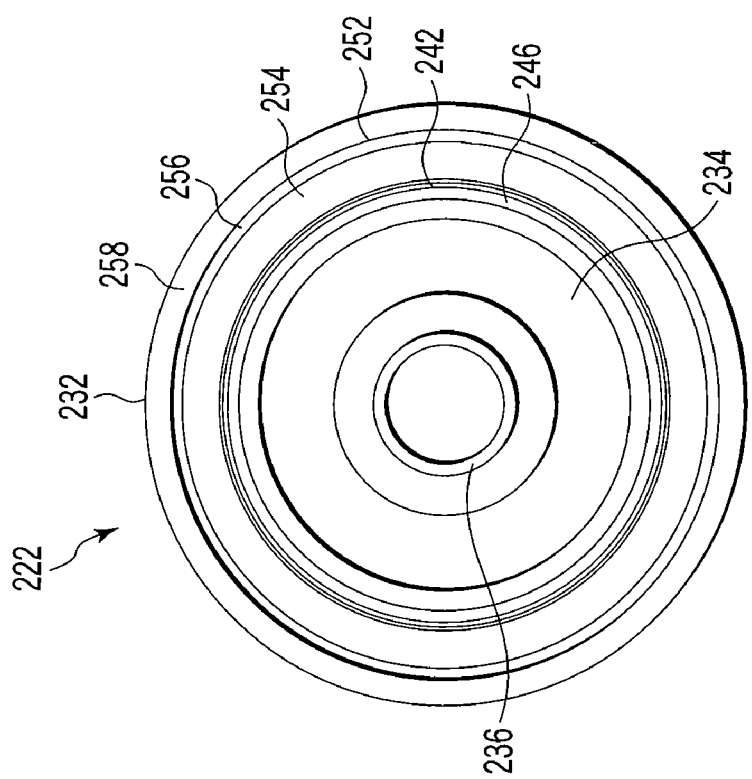
FIG. 30 is a schematic plan view showing the main body side holding portion of the electro-surgical device according to the nineteenth embodiment.

It is to be noted that in the nineteenth and twentieth embodiments, use of the high-frequency electrodes shown in FIGS. 30 and 31 has been described, but shapes and arrangements of the electrodes can variously be changed to, for example, configurations described in the first to tenth embodiments.

Twenty-First Embodiment

Next, a twenty-first embodiment will be described with reference to FIGS. 32A and 32B. This embodiment is a modification of the nineteenth and twentieth embodiments, the same members as those described in the nineteenth and twentieth embodiments are denoted with the same reference numerals, and detailed description thereof is omitted.

Here, a first high-frequency electrode 254 described in the nineteenth embodiment is used in description.

Figure 32A:
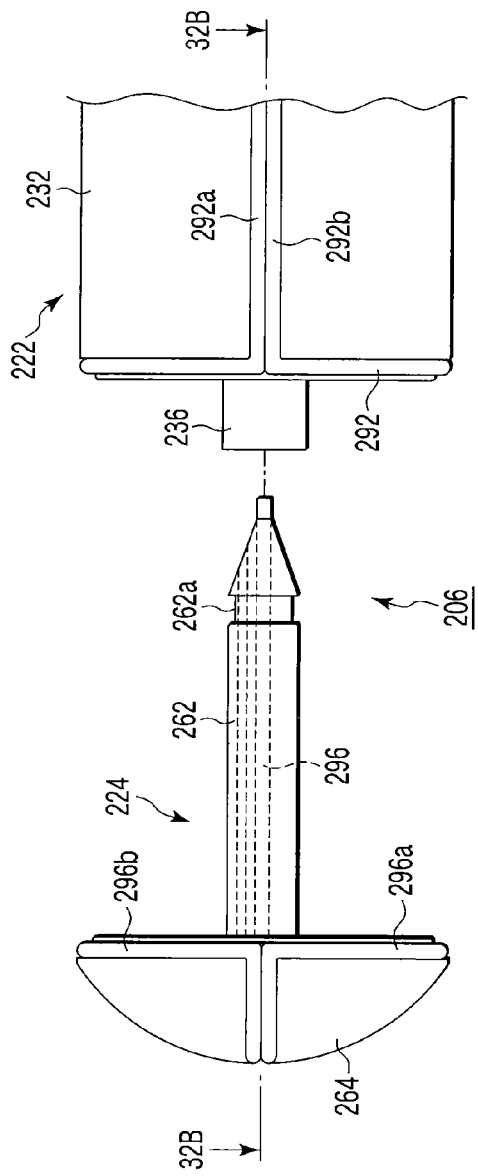
FIG. 32A is a schematic diagram showing a state in which a main body side holding portion and a detachable side holding portion are separated from each other of an electro-surgical device according to a twenty-first embodiment.
Figure 32B:
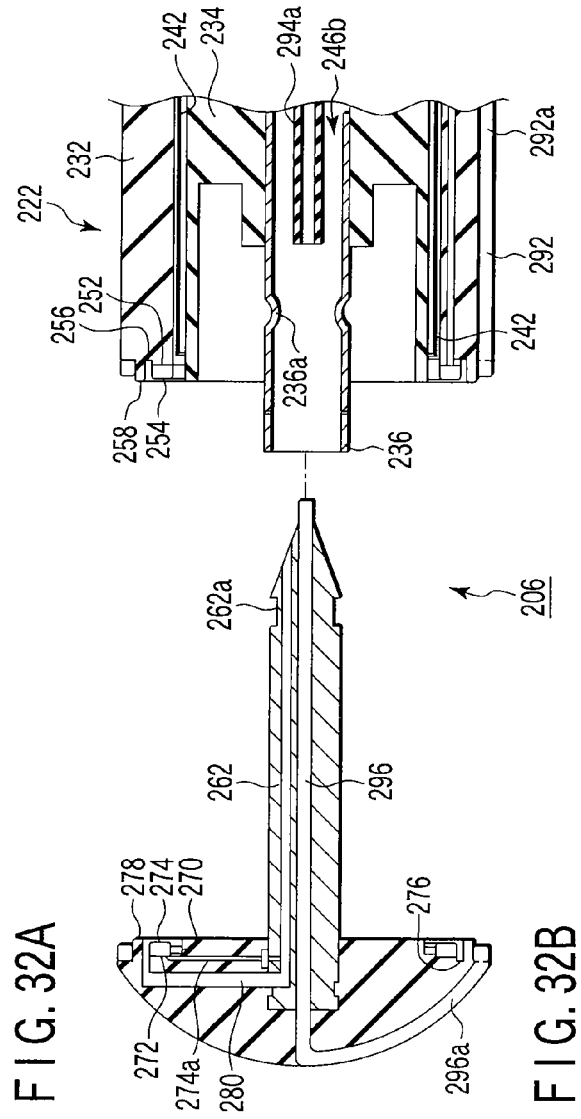
FIG. 32B is a schematic longitudinal sectional view showing a state in which the main body side holding portion and the detachable side holding portion are separated from each other of the electro-surgical device according to the twenty-first embodiment.

As shown in FIG. 32A, a first conduit 292 is formed outside a shaft 204 and a holding section 206. The first conduit 292 is turned once around an outer peripheral surface of a tip edge portion of a main body side holding portion 222, and extended from the main body side holding portion 222 to a proximal end of the shaft 204. It is to be noted that the first conduit 292 has a side denoted with reference numeral 292a for fluid supply and a side denoted with reference numeral 292b for fluid drain. Therefore, a fluid such as a gas or cooling water can be supplied or drained with respect to the first conduit 292. That is, a fluid such as the cooling water can be circulated through the first conduit 292.

Moreover, a fluid supply pipe 294a which supplies a fluid such as the cooling water is disposed in a electric conductive pipe 236. A fluid drainage pipe 294b is disposed adjacent to the fluid supply pipe 294a.

An electric conductive shaft 262 is provided with a second conduit 296 connected with the fluid supply pipe 294a and the fluid drainage pipe 294b. Two ends of the second conduit 296 protrude from a lower end of the electric conductive shaft 262. It is to be noted that the second conduit 296 has a side denoted with reference numeral 296a for fluid supply and a side denoted with reference numeral 296b for fluid drain. The second conduit 296 extends from the lower end of the electric conductive shaft 262 to a vertex of the head portion 264. The second conduit is turned once around an outer edge portion of the head portion 264 from the vertex of the head portion, again passed through the electric conductive shaft 262, and inserted into the lower end of the electric conductive shaft 262.

Moreover, an end of the second conduit 296 for fluid supply is connected with the fluid supply pipe 294a, and an end of the second conduit 296 for fluid drain is connected with the fluid drainage pipe. Therefore, when the fluid supply pipe 294a and the fluid drainage pipe 294b are connected with the second conduit 296 and the cooling water or the like is passed through the fluid supply pipe 294a, the cooling water can be drained from the fluid drainage pipe 294b through the second conduit 296. That is, a fluid such as the cooling water can be circulated through the second conduit 296.

Next, a function of a treatment system 10 according to this embodiment will be described.

A living tissue of a treatment target is held between the main body side holding portion 222 and a detachable side holding portion 224. At this time, the living tissue of the treatment target comes into contact with the first high-frequency electrode 254 and a second high-frequency electrode 274. A peripheral tissue of the living tissue of the treatment target comes into close contact with edge portions 258, 278 of the main body side holding portion 222 and the detachable side holding portion 224 and the first and second conduits 292, 296.

In this state, a foot switch and a hand switch are operated. An energy source 14 supplies energy to the first high-frequency electrode 254 and the second high-frequency electrode 274 via a cable 28, respectively. Moreover, cooling water is circulated through the first and second conduits 292, 296. In consequence, the living tissue between the first high-frequency electrode 254 and the second high-frequency electrode 274 is heated.

At this time, the fluid is generated from the heated portion of the living tissue. The fluid generated from the living tissue leads on fluid discharge grooves 256, 276 via through holes 254a, 274a of the electrodes 254, 274, respectively.

Moreover, the fluid which has led on the fluid discharge groove 256 is passed toward a handle 202 side through a first fluid flow path 246a provided with a cutter 174 and a pusher 244 for the cutter, and discharged from an electro-surgical device 12c. On the other hand, the fluid which has led on the fluid discharge groove 276 is passed toward the handle 202 side through a fluid discharge path 280 and a second fluid flow path 246b, and discharged from the electro-surgical device 12c.

When the living tissue of the treatment target is heated by heat conduction between the first high-frequency electrode 254 and the second high-frequency electrode 274, thermal spread occurs from the living tissue of the treatment target to a peripheral living tissue. This phenomenon occurs in the living tissue. Therefore, even if the living tissue is brought into close contact with the edge portions 258, 278, the heat spreads outwards over the edge portions 258, 278. At this time, the fluid for cooling is passed through the first and second conduits 292, 296 arranged outside the edge portions 258, 278. Therefore, a portion of the living tissue brought into close contact with the first and second conduits 292, 296 having a high thermal conductivity is cooled. Therefore, an influence of the heat spread from a space between the first high-frequency electrode 254 and the second high-frequency electrode 274 is suppressed at a portion brought into close contact with the first and second conduits 292, 296.

As described above, according to this embodiment, the following effects are obtained.

The description of the nineteenth embodiment applies to this embodiment.

Since the fluids for cooling are passed through the first and second conduits 292, 296 arranged outside the edge portions 258, 278, respectively, during the treatment, the living tissue brought into close contact with the first and second conduits 292, 296 can be cooled. Therefore, the influence of the heat spread from the living tissue of the treatment target to the peripheral living tissue can be suppressed at portions which come into contact with the first and second conduits 292, 296. Therefore, it can be prevented that the peripheral tissue other than the target tissue is influenced by the heat spread from the portion to which the high-frequency current has been conducted during the treatment of the living tissue.

Therefore, the fluid is prevented from leaking from the holding section 206. Moreover, the thermal spread can be inhibited to prevent the peripheral tissue of the treatment target from being influenced by the treatment. That is, the position influenced during the treatment of the living tissue can be limited to the living tissue disposed inwardly from the edge portions 258, 278.

It is to be noted that, although not shown, cooling plates which come into contact with the first conduit 292 and the second conduit 296 may be arranged as described in the sixth embodiment. In consequence, the living tissue disposed outside the main body side holding portion 222 and the detachable side holding portion 224 can more securely be prevented from being thermally influenced.

Furthermore, in the first to twenty-first embodiments described above, the use of the high-frequency electrodes has mainly been described. Instead of the high-frequency electrodes, an ultrasonic vibrator may be used. In this case, when, for example, a flat-plate-like, annular or spotted ultrasonic vibrator is ultrasonically vibrated, the living tissue brought into contact with the surface of the ultrasonic vibrator can be subjected to an ultrasonic treatment.

Moreover, a heater element (not shown) may be disposed on the surface of the main body 62 of the first holding portion 52 close to the second holding portion 54 to similarly perform the treatment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device which applies energy to a living tissue, comprising:
   first and second holding portions which are configured to relatively move with respect to each other and which include a holding surface to hold the living tissue, respectively;
   an output portion disposed on the holding surface of at least one of the first holding portion and the second holding portion, configured to come into contact with the living tissue when the living tissue is held by the first and second holding portions, and to apply the energy from an energy source to the living tissue as an object to be treated, the output portion configured to generate a fluid including a gas and a body liquid having a temperature higher than a normal temperature and a pressure higher than a normal pressure, from the living tissue, by the energy supplied from the energy source;
   an edge portion configured and disposed to arrange the output portion, disposed on the holding surface on an inner side of the edge portion, to come into contact with the living tissue when the living tissue is held by the first and second holding portions;
   a gutter having a surface which is lower than a surface on which the output portion is configured to come into contact with the living tissue and which gutter surface does not directly come into contact with the living tissue, with a closed space being formed between the surface of the gutter and the living tissue when the living tissue is held by the first and second holding portions, the gutter being filled with the fluid including the gas and the body liquid having the high pressure from the living tissue; and an opening disposed on the holding portion on which the output portion is disposed, of the first and second holding portions, the opening communicating with the gutter, and configured to urge the fluid including the gas and the body liquid having the high pressure in the gutter to be discharged to a position remote from a welding surface of the living tissue, while the living tissue is in contact with the edge portion, wherein the gutter is formed on the output portion.

2. The treatment device according to claim 1, wherein the output portion is a high-frequency electrode.

3. The treatment device according to claim 1, wherein the output portion itself is configured to generate heat.

4. A treatment device which applies energy to a living tissue, comprising:

first and second holding portions which are configured to relatively move with respect to each other and which include a holding surface to hold the living tissue, respectively;

an output portion disposed on the holding surface of at least one of the first holding portion and the second holding portion, configured to come into contact with the living tissue when the living tissue is held by the first and second holding portions, and to apply the energy from an energy source to the living tissue as an object to be treated, the output portion configured to generate a fluid including a gas and a body liquid having a temperature higher than a normal temperature and a pressure higher than a normal pressure, from the living tissue, by the energy supplied from the energy source;

an edge portion configured and disposed to arrange the output portion, disposed on the holding surface on an inner side of the edge portion, to come into contact with the living tissue when the living tissue is held by the first and second holding portions;

a gutter having a surface which is lower than a surface on which the output portion is configured to come into contact with the living tissue and which gutter surface does not directly come into contact with the living tissue, with a closed space being formed between the surface of the gutter and the living tissue when the living tissue is held by the first and second holding portions, the gutter being filled with the fluid including the gas and the body liquid having the high pressure from the living tissue;

an opening disposed on the holding portion on which the output portion is disposed, of the first and second holding portions, the opening communicating with the gutter, and configured to urge the fluid including the gas and the body liquid having the high pressure in the gutter to be discharged to a position remote from a welding surface of the living tissue, while the living tissue is in contact with the edge portion;

an auxiliary treatment device which is disposed on at least one of the first and second holding portions and which is configured to auxiliarily treat the living tissue held by the first and second holding portions, and a guide groove which is disposed on the output portion and which is configured to guide the auxiliary treatment device, wherein the guide groove communicates with the opening.

5. A treatment device which applies energy to a living tissue, comprising:

first and second holding portions which are configured to relatively move with respect to each other and which include a holding surface to hold the living tissue, respectively;

an output portion disposed on the holding surface of at least one of the first holding portion and the second holding portion, configured to come into contact with the living tissue when the living tissue is held by the first and second holding portions, and to apply the energy from an energy source to the living tissue as an object to be treated, the output portion configured to generate a fluid including a gas and a body liquid having a temperature higher than a normal temperature and a pressure higher than a normal pressure, from the living tissue, by the energy supplied from the energy source;

an edge portion configured and disposed to arrange the output portion, disposed on the holding surface on an inner side of the edge portion, to come into contact with the living tissue when the living tissue is held by the first and second holding portions;

a gutter having a surface which is lower than a surface on which the output portion is configured to come into contact with the living tissue and which gutter surface does not directly come into contact with the living tissue, with a closed space being formed between the surface of the gutter and the living tissue when the living tissue is held by the first and second holding portions, the gutter being filled with the fluid including the gas and the body liquid having the high pressure from the living tissue;

an opening disposed on the holding portion on which the output portion is disposed, of the first and second holding portions, the opening communicating with the gutter, and configured to urge the fluid including the gas and the body liquid having the high pressure in the gutter to be discharged to a position remote from a welding surface of the living tissue, while the living tissue is in contact with the edge portion;

an auxiliary treatment device which is disposed on the first holding portion and which is adapted to auxiliarily treat the living tissue held by the first and second holding portions, and a guide groove which is disposed on the periphery of the output portion and which is configured to guide the auxiliary treatment device, wherein the guide groove communicates with the opening.

6. A treatment device which applies energy to a living tissue, comprising:

first and second holding portions which are configured to relatively move with respect to each other and which include a holding surface to hold the living tissue, respectively;

an output portion disposed on the holding surface of at least one of the first holding portion and the second holding portion, configured to come into contact with the living tissue when the living tissue is held by the first and second holding portions, and to apply the energy from an energy source to the living tissue as an object to be treated, the output portion configured to generate a fluid including a gas and a body liquid having a temperature higher than a normal temperature and a pressure higher than a normal pressure, from the living tissue, by the energy supplied from the energy source;

an edge portion configured and disposed to arrange the output portion, disposed on the holding surface on an inner side of the edge portion, to come into contact with the living tissue when the living tissue is held by the first and second holding portions;

a gutter having a surface which is lower than a surface on which the output portion is configured to come into contact with the living tissue and which gutter surface does not directly come into contact with the living tissue, with a closed space being formed between the surface of the gutter and the living tissue when the living tissue is held by the first and second holding portions, the gutter being filled with the fluid including the gas and the body liquid having the high pressure from the living tissue; and an opening disposed on the holding portion on which the output portion is disposed, of the first and second holding portions, the opening communicating with the gutter, and configured to urge the fluid including the gas and the body liquid having the high pressure in the gutter to be discharged to a position remote from a welding surface of the living tissue, while the living tissue is in contact with the edge portion, wherein the first holding portion includes a cylindrical member, and a conducting pipe which is disposed in the cylindrical member and which is configured to be relatively moved with respect to the cylindrical member, the second holding portion includes a head portion provided with the output portion, and a conducting shaft which is configured to connect the head portion to the conducting pipe, the gutter is disposed at the head portion, and the opening communicates with the gutter disposed on the head portion and communicates with the conducting shaft and the conducting pipe.

7. A treatment device configured to apply energy to a living tissue, comprising:

first and second holding portions which relatively move with respect to each other and which include a holding surface configured to hold the living tissue, respectively;

an output portion disposed on at least one of holding surfaces of the first holding portion and the second holding portion, and configured to receive energy from an energy source and welding to the living tissue, the output portion configured to generate a fluid including a gas and a body liquid having a temperature higher than a normal temperature and a pressure higher than a normal pressure, from the living tissue by the energy supplied from the energy source, when the living body is welded by the first and second holding portions;

an edge portion disposed and configured to arrange the output portion disposed on the holding surface on an inner side of the edge portion, to come into contact with the living tissue when the living tissue is held by the first and second holding portions;

a groove disposed to surround the output portion between the edge portion and the output portion, on the holding surface of at least one of the first and second holding portions, and formed integrally with the holding portion to form a surface lower than a surface which is configured to be in contact with the living tissue of the output portion, the groove being filled with the fluid including the gas and the body liquid having the high pressure from the living tissue; and an opening disposed on the holding portion on which the output portion is disposed, of the first and second holding portions, the opening communicating with the groove, and configured to urge the fluid including the gas and the body liquid having the high pressure in the groove to be discharged to a position remote from the welding surface of the living tissue, when the living tissue is in contact with the edge portion.

8. The treatment device according to claim 7, wherein the output portion is surrounded with the groove.

9. The treatment device according to claim 7, wherein the output portion includes a plurality of energy emitting portions configured to emit the energy supplied from the energy source.

10. The treatment device according to claim 7, wherein the edge portion is formed in an approximately U-shape, and the groove is formed in an approximately U-shape, on an outer periphery of the output portion.

11. The treatment device according to claim 7, wherein the output portion comprises a guide groove which communicates with the groove, and the output portion is formed in an approximately U shape.

12. The treatment device according to claim 11, wherein a cutter for cutting the living tissue is configured for being arranged on the guide groove.

13. The treatment device according to claim 7, wherein the edge portion is shaped in a circle, the output portion is formed concentrically and annularly inside the edge portion, and the groove is formed concentrically and annularly inside the edge portion, along the output portion.

14. The treatment device according to claim 7, wherein the edge portion is shaped in a circle, the output portion is formed on a concentric circle inside the edge portion, and the groove is formed on an outer periphery of the output portion.

15. The treatment device according to claim 7, wherein the output portion is aligned with the holding surface of at least one of the first and second holding portions, and the groove is formed along the output portion.

16. A treatment device configured to apply energy to a living tissue, comprising:

first and second holding portions which relatively move with respect to each other; and which include a holding surface configured to hold the living tissue, respectively;

output portions disposed on the holding surface of at least one of the first and second holding portions and spaced apart with a predetermined interval, each of the output portions configured to generate a fluid including a gas and a body liquid having a temperature higher than a normal temperature and a pressure higher than a normal pressure, from the living tissue by energy supplied from an energy source;

a groove disposed to surround each of the output portions disposed on the holding surface of at least one of the first and second holding portions, the groove having a surface lower than a surface on which the output portion is configured to come into contact with the living tissue and being filled with the fluid including the gas and the body liquid having the high pressure from the living tissue; and an opening communicating with the groove, the opening being located at a position remote from the holding surface and configured to naturally extract the fluid including the gas and the body liquid having the high pressure in the groove, to a direction remote from the surface which welds to the living tissue.

17. The treatment device according to claim 16, wherein the plurality of the output portions respectively have annular-shape.

18. A medical treatment method for a living tissue by use of energy, comprising:

holding the living tissue between holding surfaces of at least two holding portions;
operating the holding portions to be separate;
adding energy from output portions on the holding surfaces of the holding portions to the living tissue;
filling a groove surrounding the output portions with a fluid including a gas and a liquid having a temperature higher than a normal temperature and a pressure higher than a normal pressure from the living tissue upon applying the energy from the output portions; and
naturally discharging from the groove the fluid including the gas and the liquid having the high pressure between the two holding portions, toward an opening portion formed remote from the holding surfaces, by the high pressure.

19. The medical treatment method according to claim 18, further comprising cooling the fluid generated from the living tissue.

* * * * *